(12) United States Patent
Dalton et al.

(10) Patent No.: US 7,344,700 B2
(45) Date of Patent: Mar. 18, 2008

(54) RADIOLABELED SELECTIVE ANDROGEN RECEPTOR MODULATORS AND THEIR USE IN PROSTATE CANCER IMAGING AND THERAPY

(75) Inventors: James T. Dalton, Upper Arlington, OH (US); Duane D. Miller, Germantown, TN (US); Leonid I. Kirkovsky, Lexington, MA (US); Arnab Mukherjee, Ann Arbor, MI (US)

(73) Assignee: University of Tennessee Research Corporation, Knoxville, TN (US)

( * ) Notice: Subject to any disclaimer, the term of this patent is extended or adjusted under 35 U.S.C. 154(b) by 0 days.

(21) Appl. No.: 10/371,210

(22) Filed: Feb. 24, 2003

(65) Prior Publication Data

US 2004/0052727 A1    Mar. 18, 2004

Related U.S. Application Data

(60) Provisional application No. 60/420,287, filed on Oct. 23, 2002, provisional application No. 60/420,247, filed on Oct. 23, 2002, provisional application No. 60/360,108, filed on Feb. 28, 2002.

(51) Int. Cl.
  *A61K 51/00*    (2006.01)
(52) U.S. Cl. .................. 424/1.45; 424/1.11; 424/1.65
(58) Field of Classification Search .............. 424/1.65, 424/1.11, 1.81, 1.85, 1.89, 1.45; 564/1, 123, 564/161, 163, 168, 153, 157, 158; 514/508, 514/518, 511, 522, 616, 617, 618, 619; 558/620, 558/412, 17, 413, 44
See application file for complete search history.

(56) References Cited

U.S. PATENT DOCUMENTS

| | | | |
|---|---|---|---|
| 3,875,229 | A | 4/1975 | Gold |
| 4,139,638 | A | 2/1979 | Neri et al. |
| 4,191,775 | A | 3/1980 | Glen |
| 4,239,776 | A | 12/1980 | Glen et al. |
| 4,282,218 | A | 8/1981 | Glen et al. |
| 4,386,080 | A | 5/1983 | Crossley et al. |
| 4,465,507 | A | 8/1984 | Konno et al. |
| 4,636,505 | A | 1/1987 | Tucker |
| 4,880,839 | A | 11/1989 | Tucker |
| 5,162,504 | A | 11/1992 | Horoszewicz |
| 5,609,849 | A | 3/1997 | Kung |
| 5,656,651 | A | 8/1997 | Sovak et al. |
| 5,914,444 | A | 6/1999 | Reinert et al. |
| 6,019,957 | A | 2/2000 | Miller et al. |
| 6,037,325 | A | 3/2000 | Gyorkos et al. |
| 6,071,957 | A | 6/2000 | Miller et al. |
| 6,090,374 | A | 7/2000 | Habeck et al. |
| 6,160,011 | A | 12/2000 | Miller et al. |
| 6,238,649 | B1 | 5/2001 | Habeck et al. |
| 6,281,339 | B1 | 8/2001 | Lehmann et al. |
| 6,441,001 | B1 | 8/2002 | Watson et al. |
| 6,482,861 | B2 | 11/2002 | Miller et al. |
| 6,492,554 | B2 | 12/2002 | Dalton et al. |
| 6,545,174 | B2 | 4/2003 | Habeck et al. |
| 6,569,896 | B2 | 5/2003 | Dalton et al. |

FOREIGN PATENT DOCUMENTS

| | | |
|---|---|---|
| EP | 0 040 932 | 12/1981 |
| EP | 0 100 172 | 2/1984 |
| EP | 000 2892 | 2/1985 |
| EP | 0 253 503 | 1/1988 |
| GB | 1360001 | 3/1970 |
| JP | 52-128329 | 10/1977 |
| JP | 54-63047 | 12/1980 |
| WO | WO95/19770 | 7/1995 |
| WO | WO98 05962 | 2/1998 |
| WO | WO98/53826 | 12/1998 |
| WO | WO98/55153 | 12/1998 |
| WO | WO 01 27622 | 4/2001 |
| WO | WO 01 28990 | 4/2001 |
| WO | WO 01 34563 | 5/2001 |
| WO | WO 02 00617 | 1/2002 |
| WO | WO 02/016310 | 2/2002 |
| WO | WO 03 011302 | 2/2003 |

OTHER PUBLICATIONS

U.S. Appl. No. 10/298,229, filed Nov. 28, 2002, Miller et al.
U.S. Appl. No. 10/270,232, filed Oct. 15, 2002, Dalton et al.
U.S. Appl. No. 10/277,108, filed Oct. 23, 2002, Dalton et al.
U.S. Appl. No. 10/270,233, filed Oct. 15, 2002, Dalton et al.
U.S. Appl. No. 10/270,732, filed Oct. 15, 2002, Dalton et al.
U.S. Appl. No. 10/371,213, filed Feb. 24, 2003, Dalton et al.
U.S. Appl. No. 10/371,155, filed Feb. 24, 2003, Dalton et al.
U.S. Appl. No. 10/371,209, filed Feb. 24, 2003, Dalton et al.
U.S. Appl. No. 10/371,211, filed Feb. 24, 2003, Dalton et al.

(Continued)

*Primary Examiner*—Dameron L. Jones
(74) *Attorney, Agent, or Firm*—Pearl Cohen Zedek Latzer, LLP; Mark S. Cohen

(57) ABSTRACT

Provided is a class of radiolabeled androgen receptor targeting agents (ARTA), useful for prostate cancer imaging and in treating or preventing prostate cancer. The agents define a new-subclass of radiolabeled compounds, which are selective androgen receptor modulators (SARM), which demonstrate antiandrogenic activity of a nonsteroidal ligand for the androgen receptor, and/or which bind irreversibly to the androgen receptor. The present invention further provides methods for a) imaging of cancer in a subject, b) imaging an androgen receptor-containing tissue in a subject, c) in-vivo imaging in a subject, d) treating a subject suffering from prostate cancer, e) delaying the progression of prostate cancer in a subject suffering from prostate cancer, f) preventing the recurrence of prostate cancer in a subject suffering from prostate cancer, and g) treating the recurrence of prostate cancer in a subject suffering from prostate cancer, which comprise using the radiolabeled compounds of the present invention. The present invention further provides a method of producing the radiolabeled SARM compounds, and precursor compounds useful in the preparation of the radiolabeled SARM compounds.

15 Claims, No Drawings

OTHER PUBLICATIONS

U.S. Appl. No. 10/359,270, filed Feb. 6, 2003, Steiner et al.
U.S. Appl. No. 10/310,150, filed Dec. 5, 2002, Steiner et al.
Eliason et al., "High Throuphut Fluorescence Polarization-Based Screening Assays for the Identification of Novel Nuclear Receptor Ligands," Abstracts of Papers, 223rd ACS National Meeting, Orlando, FL, United States, (2002), Apr. 7, 2002.
Howard Tucker and Glynne J. Chesterson, J. Med Chem. 1988, 31, pp. 885-887, "Resolution of the Nonsteroidal Antiandrogen—4'-Cyano-3-[(4-fluorophenyl)sulfonyl]-2-hydroxy-2-methyl-3'-(trifluoromethyl)-propionanilide and the Determination of the Absolute Configuration of the Active Enantiomer".
D. McKillop, et al., "Enantioselective metabolism and pharmacokinetics of Casodex in the male rat", Xenobiotica, 1995, vol. 25, No. 6, 623-634.
Leonid Kirkovsky, et al., "[$^{125}$I]-Radionated Bicalutamide Analogs as Potential Imaging Agents for Prostate Cancer", Poster Presentation MEDI 155, 214th ACS National Meeting, Las Vegas, NV, Sep. 7-11, 1997, Department of Pharmaceutical Sciences, University of Tennessee, Memphis, TN 38163.
David T. Baird and Anna F. Glasier, "Hormonal Contraception—Drug Therapy", The New England Journal of Medicine , May 27, 1993, pp. 1543-1549.
F.C. W. Wu, "Male Contraception: Current Status and Future Prospects", Clinical Endocrinology, (1988), 29, pp. 443-465.
Carl Djerassi and S.P. Leibo, "A new look at male contraception", Nature, 1994 vol. 370, pp. 11-12.
World Health Organisation Task Force on Methods for the Regulation of Male Fertility, "Contraceptive efficacy of testosterone-induced azoospermia in normal men", The Lancet, vol. 336, Oct. 20, 1990, pp. 955-959and 1517-1518.
C. G. Francisco, et al., "Long-acting contraceptive agents: testosterone esters of unsaturated acids", Steroids, Jan. 1990, vol. 55, Butterworths.
John M. Hoberman and Charles E. Yesalis, "The History of Synthetic Testosterone", Scientific American, Feb. 1995, pp. 76-81.
Leonid Kirkovsky, et al., "Approaches to Irreversible non-steroidal chiral antiandrogens", Department of Pharmaceutical Sciences, University of Tennessee, 47th Southeast/51st Southwest Joint Regional Meeting of the American Chemical Society, Memphis, TN, Nov. 29-Dec. 1, 1995.
David J. Handelsman, "Bridging the gender gap in contraception: another hurdle cleared" The Medical Journal of Australia, vol. 154, Feb. 18, 1996, pp. 230-233.
Edwards JP, Higuchi RI, Winn DT, Pooley CLF, Caferro TR, Hamann LG, Zhi L, Marschke KB, Goldman ME, and Jones TK. Nonsteroidal androgen receptor agonists based on 4-(trifluoromethyl)-2H-pyrano[3,2-g]quinolin-2-one. Bioorg. Med. Chem. Lett., 9: 1003, 1999.
Zhi L, Tegley CM, Marschke KB, and Jones TK. Switching androgen receptor antagonists to agonists by modifying C-ring substituents on piperidino[3,2-g]quinolone. Bioorg. Med. Chem. Lett., 9: 1009, 1999.

Higuchi RI, Edwards JP, Caferro TR, Ringgenberg JD, Kong JW, Hamann LG, Arienti KL, Marschke KB, Davis RL, Farmer LJ, and Jones TK. 4-Alkyl- and 3,4-diaklyl-1,2,3,4-tetrahydro-8-pyridono[5,6-g]quinolines: potent, nonsteroidal androgen receptor agonists. Bioorg. Med. Chem. Lett., 9:1335,1999.
Hamann LG, Mani NS, Davis RL, Wang XN, Marschke KB, and Jones TK. Discovery of a potent, orally active nonsteroidal androgen receptor agonist: 4-ethyl-1,2,3,4-tetrahydro-6-(trifluoromethyl)-8-pyridono[5,6-g]-quinoline (LG121071). J. Med. Chem., 42: 210, 1999.
Rosen J, Day A, Jones TK, Jones ET, Nadzan AM, and Stein RB. Intracellular receptors and signal transducers and activators of transcription superfamilies: novel targets for small-molecule drug discovery. J. Med. Chem., 38: 4855, 1995.
Dalton JT, Mukherjee A, Zhu Z, Kirkovsky L, and Miller DD. Discovery of Nonsteroidal Androgens. Biochem. Biophys. Res. Commun.,244(1):1-4, 1998.
Edwards JP, West SJ, Pooley CLF, Marschke KB, Farmer LJ, and Jones TK. New nonsteroidal androgen receptor modulators based on 4-(trifluoromethyl)-2-(1H)-Pyrololidino[3,2-g]quinolone. Bioorg. Med. Chem. Lett., 8: 745, 1998.
Berger et al., "Concepts and limitations in the application of radiolabeled antiandrogens, estrogens, or androgens as isotropic scanning agents for the prostate", Invest. Urol, (1975), 1391, 10-16.
Yin, et al (2003) "Pharmacology, Pharmacokinetics and Metabolism of Acetothiolutamide, a Novel Nonsteroidal Agonist for the Androgen Receptor." The Journal of Pharmacology and Experimental Therapeutics. vol. 3, 1323-1333.
Yin, et al (2002) "Pharmacodynamics of Selective Androgen Receptor Modulators." The Journal of Pharmacology and Experimental Therapeutics. vol. 304, 1334-1340.
Yang, et al (2006) "Preclinical Pharmacology of a Nonsteroidal Ligand for Androgen Receptor-Mediated Imaging of Prostate Cancer." The Journal of Pharmacology and Experimental Therapeutics. vol. 317, 402-408.
Nair, et al (2005) "Synthesis of irreversibly bicalutamide analogs for imaging studies." Tetrahedron Letters, vol. 46 4821-4823.
Nair, et al (2004) "Synthesis of novel iodo derived bicalutamide analogs." Tetrahedron Letters, vol. 45 9475-9477.
Mukherjee, et al (1999) "Affinity Labeling of the Angrogen Receptor with Nonsteroidal Chemoaffinity Ligands." Biochemical Pharmacology vol. 58, 1259-1267.
Kirkovsky, et al (2000) "Chiral Nonsteroidal Affinity Ligands for the Androgen Receptor. 1. Bicalutamide Analogues Bearing Electrophilic Groups in the B Aromatic Ring." J. Med. Chem. vol. 43, 581-590.
He, et al (2002) "Novel nonsteroidal ligands with high binding affinity and potent functional activity for the androgen receptor." Eur. J. Med Chem. 619-634.
Yin, et al (2003) "Key Structural Features of Nonsteroidal Ligands of Binding and Activation of the Androgen Receptor." Molecular Pharmacology 211-223.

RADIOLABELED SELECTIVE ANDROGEN RECEPTOR MODULATORS AND THEIR USE IN PROSTATE CANCER IMAGING AND THERAPY

CROSS REFERENCE TO RELATED APPLICATIONS

This Application claims priority of U.S. Ser. No. 60/360,108 filed Feb. 28, 2002, U.S. Ser. No. 60/420,287 filed Oct. 23, 2002, and U.S. Ser. No. 60/420,247 filed Oct. 23, 2002, the contents of which are hereby incorporated by reference.

FIELD OF INVENTION

The present invention relates to radiolabeled selective androgen receptor modulator (SARM) compounds and their use in imaging and prevention/therapy of prostate cancer. The present invention further relates to methods for 1) imaging of cancer in a subject, 2) imaging an androgen receptor-containing tissue in a subject, 3) in-vivo imaging in a subject, 4) treating a subject-suffering from prostate cancer, 5) delaying the progression of prostate cancer in a subject suffering from prostate cancer, 6) preventing the recurrence of prostate cancer in a subject suffering from prostate cancer, and 7) treating the recurrence of prostate cancer in a subject suffering from prostate cancer, which comprise using the radiolabeled compounds of the present invention.

BACKGROUND OF THE INVENTION

The androgen receptor ("AR") is a ligand-activated transcriptional regulatory protein that mediates induction of male sexual development and function through its activity with endogenous androgens. Androgens are generally known as the male sex hormones. The androgenic hormones are steroids, which are produced in the body by the testes and the cortex of the adrenal gland or synthesized in the laboratory. Androgenic steroids play an important role in many physiologic processes, including the development and maintenance of male sexual characteristics such as muscle and bone mass, prostate growth, spermatogenesis, and male hair pattern (Matsumoto, *Endocrinol. Met. Clin. N. Am.* (1994) 23:857–75). The endogenous steroidal androgens include testosterone and dihydrotestosterone ("DHT"). Testosterone is the principal steroid secreted by the testes and is the primary circulating androgen found in the plasma of males. Testosterone is converted to DHT by the enzyme 5 alpha-reductase in many peripheral tissues. DHT is thus thought to serve as the intracellular mediator for most androgen actions (Zhou, et al., *Molec. Endocrinol.* (1995), 9:208–18). Other steroidal androgens include esters of testosterone, such as the cypionate, propionate, phenylpropionate, cyclopentylpropionate, isocarporate, enanthate, and decanoate esters, and other synthetic androgens such as 7-Methyl-Nortestosterone ("MENT") and its acetate ester (Sundaram et al., "7 Alpha-Methyl-Nortestosterone (MENT): The Optimal Androgen For Male Contraception," *Ann. Med.*, (1993) 25: 199–205 ("Sundaram")). Because the AR is involved in male sexual development and function, the AR is a likely target for effecting male contraception or other forms of hormone replacement therapy.

Steroidal ligands, which bind the AR and act as androgens (e.g. testosterone enanthate) or as antiandrogens (e.g. cyproterone acetate), have been known for many years and are used clinically (Wu 1988). Although nonsteroidal antiandrogens are in clinical use for hormone-dependent prostate cancer, nonsteroidal androgens have not been reported.

Prostate cancer is the most frequently diagnosed non-skin cancer in American men, accounting for approximately 27% of all cancer cases (Boring, *Cancer Statistics* (1993), 43:7–26). Treatment for prostate cancer depends on the stage at which the cancer is found, and on the age and health status of the patient. As with other malignancies, accurate staging of prostate cancer is absolutely critical in selecting the most appropriate form of therapy. Clinically localized disease is potentially curable with standard surgery and/or radiation therapy. However, no curative therapies exist for advanced disease. Existing diagnostic tests such as magnetic resonance imaging ("MRI"), computed tomographic scans ("CT"), and ultrasound ("US") lack both the specificity and sensitivity to substitute for exploratory surgery in staging malignant disease. Because of inadequate diagnostic studies, patients with what is presumed to be surgically curable prostate cancer must submit to surgical staging to determine the presence or absence of lymph node metastases. Almost half of the men initially diagnosed with local disease are found to have tumors which have advanced to the periprostatic area or beyond at the time of surgery (Carter et al., In: "A Multidisciplinary Analysis of Controversies in the Management of Prostate Cancer," Coffey et al., eds., pp. 1–7, Plenum, New York). Thus, nearly one-third of all men diagnosed with prostate cancer (i.e., about 80,000 men per year) undergo surgery from which they are unlikely to benefit. Thus, non-invasive, more selective, and more accurate imaging tools for prostate cancer are needed.

Knowledge of the presence, location, and extent of disease aids in selecting which patients are likely to benefit from radical surgery, radiotherapy, or androgen ablation. Single photon emission computed tomography ("SPECT") is a form of chemical imaging in which emissions from radiopharmaceuticals, labeled with gamma-emitting radionuclides (e.g. $^{99m}$Tc, $^{67}$Ga, $^{111}$In, or $^{123}$I) are used to create cross-sectional CT images of radioactivity distribution in vivo. Imaging of this type is typically done with non-specific compounds (e.g. albumin or chelating agents like DTPA) complexed with the radionuclide. This, and similar methods, thus have the potential to improve the ability of CT and MRI to detect lymph nodes as well as bony and other visceral metastases. However, these methods are not selective. Radioimmunoscintigraphy using monoclonal antibodies ("MoAbs"), which recognize prostate-specific proteins, including PSA and prostatic acid phosphatase ("PAP"), was developed as a means to specifically image the tumor, as opposed to the underlying host tissues. This approach has met with some success for these purposes (Dillman et al., "Radioimmunodetection of Cancer With The Use of Indium-111-Labeled Monoclonal Antibodies," *Natl. Cancer Inst. Monogr.*, (1987), 3, 33; Vihko et al., "Immunoscintigraphic Evaluation of Lymph Node Involvement in Prostate Carcinoma," Prostate (1987), 11, 51). Prostascint is an IgG1 murine monoclonal antibody conjugated to the $^{111}$In chelator GYK-DTPA to form the immunoconjugate $^{111}$In capromab pendetide. This antibody conjugate is reported to have a high degree of binding to all prostate cancers and mild binding to benign prostatic hypertrophic and normal prostate tissue. Preliminary data showed that this MoAb was able to detect disease foci of 5 mm or greater with a negative predictive value of 83% and positive predictive value of 50%, suggesting that radioimaging is a promising technique for prognostication of prostate cancer (Babaian et al., "Radioimmunoscintigraphy of Pelvic Lymph Nodes With 111-Indium-Labeled Monoclonal Antibody CYT-356," *J. Urol.*, (1994), 152, 1952). However, a major concern is that patients may develop human antimurine antibody ("HAMA") responses as a result of the murine origin of the antibody, resulting in adverse reactions and precluding the use of subsequent antibody imaging (Babaian et al., "Radioimmunological Imaging of Metastatic Prostate Cancer With $^{111}$-Indium-Labeled Monoclonal Antibody PAY276," *J. Urol.*, (1987), 137, 439).

Chemical imaging represents a viable alternative to immunological methods. In this instance, the increase in imaging specificity is gained as the result of the preferential distribution of a radiochemical into an anatomical region of interest. Wolf recently defined pharmacokinetic imaging as the measurement of the rate of change of a radiochemical in an anatomic space, or chemical imaging with the added dimension of time (Wolf, "Imaging Can Be Much More Than Pretty Pictures," *Pharmaceut. Res.*, (1995), 12:1821–22). This technique can be powerful, because it allows one to obtain noninvasive measurements of the pharmacokinetics and pharmacodynamics of a radiolabeled compound at the target tissue site (Presant et al., "Association of Intratumoral Pharmacokinetics of Fluorouracil With Clinical Response," The Lancet, (1994) 343:1184–87; Dowell et al., "Pharmacokinetic Parameters of Cisplatin Can Be Estimated in Human Tumors by Noninvasive Measurements of the Biodistribution and Targeting of $^{195m}$Pt cisplatin," *Proc. Am. Assoc. Cancer Res.*, (1995); 36:360). Receptor-mediated chemical imaging has been used for the imaging of other endocrine tumors. $^{111}$In pentetreotide (Octreoscan®) is used clinically for the imaging of somatostatin receptors present in neuroendocrine tumors. It has also been shown that 16.alpha.-[$^{18}$F] fluoroestradiol and 21-[$^{18}$F]fluoro-16.alpha.-ethyl-19-norprogesterone can be used with positron emission tomography ("PET") to provide clear images of both estrogen and progesterone receptor-positive breast tumors (Mintun et al., "Positron Tomographic Imaging of Estrogen Receptors in Human Breast Tumors," *Radiology*, (1988), 169:45; McGuire et al., "Positron Tomographic Assessment of 16.alpha.-[$^{18}$F]-Fluoroestradiol Uptake in Metastatic Breast Carcinoma," *J. Nucl. Med.*, (1991), 32:1526; Pomper et al., "21-[$^{18}$F]fluoro-16.alpha.-ethyl-19-norprogesterone: Synthesis and Target Tissue Selective Uptake of a Progestin Receptor Based Radiotracer for Positron Emission Tomography," *J. Med. Chem.*, (1988), 31:1360; Dehdashti et al., "Assessment of 21-[$^{18}$F] fluoro-16.alpha.-ethyl-19-norprogesterone as a Positron-Emitting Radiopharmaceutical for Detection of Progestin Receptors in Human Breast Carcinomas," *J. Nucl. Med.*, (1991), 32:1532). A variety of steroidal androgens incorporating photon-emitting and positron-emitting radionuclides have been synthesized and evaluated for their potential in imaging AR-positive tumors of the prostate (Carlson et al., "A Comparative Study of the Selectivity and Efficiency of Target Tissue Uptake of Five Tritium-labeled Androgens in the Rat," *J. Steroid Biochem.*, (1990), 36:549 ("Carlson"); Brandes et al., "Fluorinated Androgens and Progestins: Molecular Probes for Androgen and Progesterone Receptors with Potential Use in Positron Emission Tomography," *Molec. Pharmacol.*, (1987), 32:391 ("Brandes"); Liu et al., "20-[$^{18}$F] fluoro-mibolerone, A Positron-Emitting Radiotracer For Androgen Receptors: Synthesis and Tissue Distribution Studies," *J. Nucl. Med.*, (991), 32:81 ("Liu 1991"); Choe et al., "Synthesis of 11.beta.-[$^{18}$F] fluoro-5.alpha.-dihydrotestosterone and 11.beta.[$^{18}$F] fluoro-19-nor-5.alpha.-dihydrotestosterone: Preparation Via Haloflu-orination-Reduction, Receptor Binding, and Tissue Distribution," *J. Med. Chem.*, (1995), 38:816 ("Choe"); Liu et al., "Synthesis of High Affinity Fluorine-Substituted Ligands for the Androgen Receptor. Potential Agents for Imaging Prostatic Cancer By Positron Emission Tomography," *J. Med. Chem.*, (1992), 35:2113 ("Liu 1992"); Hoyte et al., "7.alpha.-methyl-17.alpha.-(E-2'-[$^{125}$I]iodovinyl)-19-nortestosterone: A New Radioligand for the Detection of Androgen Receptor," *Steroids* (1993) 58:13 ("Hoyte"); Ali et al., "Synthesis of 17.alpha., 20E/Z)iodovinyl testosterone and 19-nortestosterone Derivatives as Potential Radioligands for Androgen and Progesterone Receptors," *J. Steroid Biochem. Mol. Biol.*, (1994), 49:15 ("Ali")). However, the majority of these compounds were not useful for AR-mediated imaging due to rapid metabolic cleavage of the radiolabel, low AR binding affinity, or inadequate specific activity. Carlson and Katzenellenbogen examined the target tissue selectivity of tritiated testosterone, dihydrotestosterone, 19-nortestosterone, mibolerone (MEB), and methyltrienolone (R1881) in rats, concluding that compounds with AR binding affinities comparable to or greater than that of testosterone would be required to provide adequate target tissue uptake and target-to-nontarget contrast for successful in vivo imaging of androgen target tissues (Carlson). MIB and R 1881 demonstrated encouraging selectivity and target tissue uptake in animal models, most likely due to their slower in vivo metabolic clearance as compared to the other androgens (Carlson; Brandes; Liu 1992; Choe; Liu 1991). Bonasera ("Preclinical Evaluation of fluorine-18-labeled Androgen Receptor Ligands in Baboons," *J. Nucl. Med.*, (1996), 37:1009–15 (1996)) studied $^{18}$F-labeled steroids using PET in baboons and is now studying 16beta-[$^{18}$F] fluoro-5.alpha.-dihydrotestosterone in men with metastatic prostate cancer.

Based on previous reports, the most important properties of radiolabeled androgens with respect to AR imaging appear to be: (i) the selectivity and affinity for AR binding; and (ii) the rate of in vivo metabolism (Carlson; Brandes; Liu 1992; Choe; Liu 1991; Hoyte; Ali). Androgenic steroids, like other steroids, are known to bind with other steroid receptors (Carlson; Dunn et al., "Transport of Steroid Hormones: Binding of 21 Endogenous Steroids to Both Testosterone-binding Globulin and Corticosteroid-binding Globulin in Human Plasma," *J. Clin. Endrocrinol.*, (1981) 53:58 ("Dunn")). Binding of steroidal AR-imaging agents to progesterone and/or glucocorticoid receptors in the body contributes to their poor target site specificity for imaging. Radioactivity levels that remain in the blood or in non-target tissues are affected by the extent to which the agent binds to high affinity, non-target proteins (Carlson; Choe; Ali). Further, the natural androgens (i.e., testosterone and dihydrotestosterone) are extensively bound to sex hormone-binding globulin ("SHBG"), a high affinity, low capacity binding plasma protein (Dunn). Not surprisingly, many of the synthetic androgens also bind to SHBG with high affinity (Carlson; Brandes; Liu 1991; Liu 1992; Choe; Hoyte; Ali). These high affinity SHBG sites compete with the AR for specific binding of the radiolabeled ligand, and have precluded the use of a number of steroidal AR ligands for imaging. The metabolic fate and pharmacokinetics of AR-imaging agents are also important factors determining their usefulness for in vivo imaging (Carlson). Studies with estrogen and progestin imaging agents showed that in vivo target-to-nontarget uptake ratios correlated with the ratio of specific to non-specific binding in vitro (vanBrocklin et al., "16.beta.-([$^{18}$F]fluoro)estrogens: Systematic Investigation of a New Series of Fluorine-18-Labeled Estrogens as Potential Imaging Agents for Estrogen-Receptor-Positive Breast Tumors," *J. Med. Chem.*, (1993), 35:1619). However, it was recently found that this relationship did not hold for a series of androgen analogs (Choe). In the series of compounds therein, the compound with highest relative binding affinity ("RBA") and lowest non-specific binding had a-poor target-to-nontarget tissue uptake ratio, while the compound with the lowest RBA demonstrated the highest target-to-nontarget tissue ratio in vivo. As a whole, these data strongly suggest that in vivo metabolism is a major factor in determining the distribution profile in vivo (Carlson; Brandes; Choe; Ali).

In addition to their use in medical imaging, radiolabeled Androgen Receptor ligands (AR ligands) labeled with radionuclides (e.g. $^{90}Y$, $^{177}Lu$, $^{149}Pm$, $^{153}Sm$, $^{166}Ho$, $^{131}I$, $^{32}P$, $^{211}At$ $^{47}Sc$, $^{109}Pd$, $^{105}Rh$, $^{186/188}Re$, $^{99}Tc$ and $^{67}Cu$) may be used in therapy. In this case, the radionuclide (i.e., radioisotope) serves as the radiation source. The choice of the appropriate isotope for radiotherapy requires consideration of a variety of factors, such as tumor uptake and retention, blood clearance, rate of radiation delivery, half-life and specific activity of the radionuclide, and the economics of producing the radiopharmaceutical containing the radionuclide. The therapeutic AR ligand is designed to deliver the requisite amount of radiation dose to the tumor cells and to achieve a cytotoxic effect while avoiding side effects to normal tissue.

There is a need in the art to develop new non-steroidal compounds which bind the androgen receptor with high affinity and which are useful in imaging prostate cancer and in treating or preventing prostate cancer.

SUMMARY OF THE INVENTION

In one embodiment, this invention provides a class of radiolabeled androgen receptor targeting agents (ARTA). The agents define a new subclass of radiolabeled compounds, which are selective androgen receptor modulators (SARM) useful for prostate cancer imaging and in treating or preventing prostate cancer. The present invention further provides methods for a) imaging of cancer in a subject, b) imaging an androgen receptor-containing tissue in a subject, c) in-vivo imaging in a subject, d) treating a subject suffering from prostate cancer, e) delaying the progression of prostate cancer in a subject suffering from prostate cancer, f) preventing the recurrence of prostate cancer in a subject suffering from prostate cancer, and g) treating the recurrence of prostate cancer in a subject suffering from prostate cancer, which comprise using the radiolabeled compounds of the present invention.

In one embodiment, the present invention provides a radiolabeled selective androgen receptor modulator (SARM) compound represented by the structure of formula I:

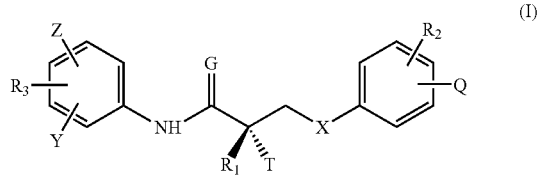

(I)

wherein X is a radioactive or nonradioactive O, S, SO$_2$, CH$_2$, NH, NR, Se, PR, or NO, or X is a bond;
  G is a radioactive or nonradioactive O or S;
  T is a radioactive or nonradioactive OH, OR, —NH-COCH$_3$, or NHCOR;

Z is a radioactive or a nonradioactive NO$_2$, CN, COR, COOH, or CONHR;
Y is a radioactive or a nonradioactive CF$_3$, F, Br, Cl, I, CN, or SnR$_3$;
Q is a radioactive or a nonradioactive alkyl, halogen, CF$_3$, CN, CR$_3$, SnR$_3$, NR$_2$, NHCOCH$_3$, NHCOCF$_3$, NHCOR, NHCONHR, NHCOOR, OCONHR, CONHR, NHCSCH$_3$, NHCSCF$_3$, NHCSR, NHSO$_2$CH$_3$, NHSO$_2$R, OR, COR, OCOR, OSO$_2$R, SO$_2$R, SR, SCN, NCS, OCN, NCO; or Q together with the benzene ring to which it is attached is a fused ring system represented by structure A, B or C:

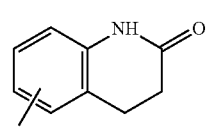

A

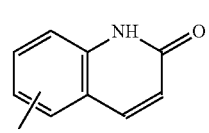

B

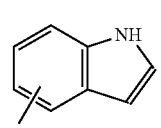

C

R is a radioactive or a nonradioactive alkyl, haloalkyl, dihaloalkyl, trihaloalkyl, CH$_2$F, CHF$_2$, CF$_3$, CF$_2$CF$_3$, aryl, phenyl, halogen, alkenyl or OH; and
R$_1$ is a radioactive or nonradioactive CH$_3$, CH$_2$F, CHF$_2$, CF$_3$, CH$_2$CH$_3$, or CF$_2$CF$_3$;
R$_2$ is a radioactive or a nonradioactive F, Cl, Br, I, OH, CN, NO$_2$, NHCOCH$_3$, NHCOCF$_3$, NHCOR, alkyl, arylalkyl, OR, NH$_2$, NHR, NR$_2$, SR; and
R$_3$ is a radioactive or a nonradioactive F, Cl, Br, I, CN, NO$_2$, COR, COOH, CONHR, CF$_3$, SnR$_3$;

wherein at least one of X, T, Z, Y, Q, R, R$_1$, R$_2$ or R$_3$ is radioactive.

In another embodiment, the present invention provides an analog, derivative, isomer, metabolite, pharmaceutically acceptable salt, pharmaceutical product, hydrate or N-oxide of the compound of formula I, or any combination thereof.

In one embodiment, the present invention provides a radiolabeled compound of formula I wherein G is O. In one embodiment, the present invention provides a radiolabeled compound of formula I wherein X is O. In one embodiment, the present invention provides a radiolabeled compound of formula I wherein T is OH. In one embodiment, the present invention provides a radiolabeled compound of formula I wherein R$_1$ is CH$_3$. In another embodiment, Z the present invention provides a radiolabeled compound of formula I wherein is NO$_2$. In another embodiment, the present invention provides a radiolabeled compound of formula I wherein Z is CN. In another embodiment, the present invention provides a radiolabeled compound of formula I wherein Y is CF$_3$. In another embodiment, the present invention provides a radiolabeled compound of formula I wherein Q is NHCOCH$_3$. In another embodiment, the present invention provides a radiolabeled compound of formula I wherein Q is F. In another embodiment, the present invention provides a radiolabeled compound of formula I wherein Q is NCS. In another embodiment, the present invention provides a radiolabeled compound of formula I wherein $R_2$ is a radioactive halogen. In another embodiment, the present invention provides a radiolabeled compound of formula I wherein $R_3$ is a radioactive halogen.

In one embodiment, the SARM compound of formula I is an androgen receptor ligand. In another embodiment, the SARM compound is an androgen receptor antagonist. In another embodiment, the SARM compound binds irreversibly to an androgen receptor. In another embodiment, the SARM compound is an alkylating agent. In another embodiment, the SARM compound is an androgen receptor antagonist which binds irreversibly to an androgen receptor.

In one embodiment, the present invention provides a radiolabeled selective androgen receptor modulator (SARM) compound represented by the structure of formula II:

$$RI\text{-}(Ch)_n\text{-}(Li)_m\text{-}(SARM) \qquad II$$

wherein
- RI is a radioisotope;
- Ch is a metal chelator;
- Li is a linker moiety;
- m is 0 or 1;
- n is 0 or 1; and
- SARM is a selective androgen receptor modulator compound represented by the structure of any of formulas III–VI:

Formula III:

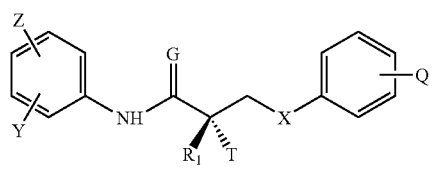

wherein G is O or S;
X is a bond, O, S, $SO_2$, $CH_2$, NH, NR, Se, PR, or NO;
T is OH, OR, —$NHCOCH_3$, or NHCOR
Z is $NO_2$, CN, COOH, COR, NHCOR or CONHR;
Y is $CF_3$, F, I, Br, Cl, CN, $CR_3$ or $SnR_3$;
Q is alkyl, halogen, $CF_3$, CN, $CR_3$, $SnR_3$, $NR_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OR, COR, OCOR, $OSO_2R$, $SO_2R$, SR, SCN, NCS, OCN, NCO; or Q together with the benzene ring to which it is attached is a fused ring system represented by structure A, B or C:

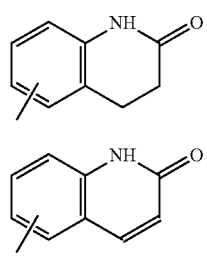

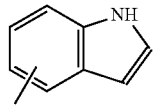

R is alkyl, haloalkyl, dihaloalkyl, trihaloalkyl, $CH_2F$, $CHF_2$, $CF_3$, $CF_2CF_3$, aryl, phenyl, halogen, alkenyl or OH; and $R_1$ is $CH_3$, $CH_2F$, $CHF_2$, $CF_3$, $CH_2CH_3$, or $CF_2CF_3$;

or its analog, isomer, metabolite, derivative, pharmaceutically acceptable salt, pharmaceutical product, N-oxide, hydrate or any combination thereof;

Formula IV:

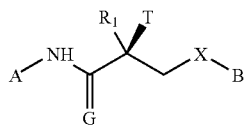

wherein X is a bond, O, $CH_2$, NH, Se, PR, NO or NR;
G is O or S;
$R_1$ is $CH_3$, $CH_2F$, $CHF_2$, $CF_3$, $CH_2CH_3$, or $CF_2CF_3$;
T is OH, OR, —$NHCOCH_3$, or NHCOR;
R is alkyl, haloalkyl, dihaloalkyl, trihaloalkyl, $CH_2F$, $CHF_2$, $CF_3$, $CF_2CF_3$, aryl, phenyl, halogen, alkenyl or OH;
A is a ring selected from:

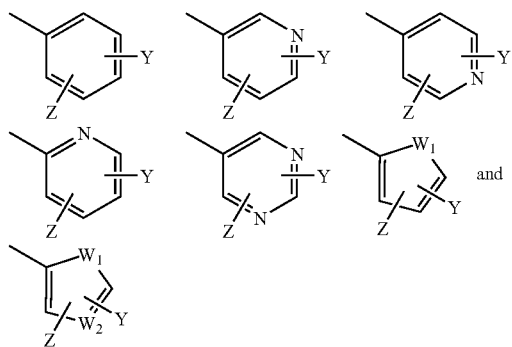

B is a ring selected from:

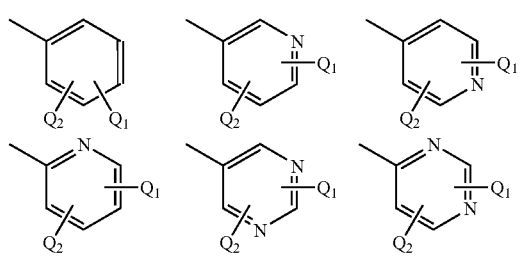

-continued wherein A and B cannot simultaneously be a benzene ring;

Z is $NO_2$, CN, COOH, COR, NHCOR or CONHR;

Y is $CF_3$, F, I, Br, Cl, CN, $CR_3$ or $SnR_3$;

$Q_1$ and $Q_2$ are independently of each other a hydrogen, alkyl, halogen, $CF_3$, CN, $CR_3$, $SnR_3$, $NR_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OR, COR, OCOR, $OSO_2R$, $SO_2R$, SR, SCN, NCS, OCN, NCO, $Q_3$ and $Q_4$ are independently of each other a hydrogen, alkyl, halogen, $CF_3$, CN, $CR_3$, $SnR_3$, $NR_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OR, COR, OCOR, $OSO_2R$, $SO_2R$ SR, SCN, NCS, OCN, or NCO;

$W_1$ is O, NH, NR, NO or S; and $W_2$ is N or NO;

or its analog, isomer, metabolite, derivative, pharmaceutically acceptable salt, pharmaceutical product, N-oxide, hydrate or any combination thereof;

Formula V:

V wherein X is a bond, O, S, $SO_2$, $CH_2$, NH, NR, Se, PR, or NO;

G is O or S;

T is OH, OR, —$NHCOCH_3$, or NHCOR;

R is alkyl, haloalkyl, dihaloalkyl, trihaloalkyl, $CH_2F$, $CHF_2$, $CF_3$, $CF_2CF_3$, aryl, phenyl, halogen, alkenyl or OH;

$R_1$ is $CH_3$, $CH_2F$, $CHF_2$, $CF_3$, $CH_2CH_3$, or $CF_2CF_3$;

$R_2$ is F, Cl, Br, I, $CH_3$, $CF_3$, OH, CN, $NO_2$, $NHCOCH_3$, $NHCOCF_3$, NHCOR, alkyl, arylalkyl, OR, $NH_2$, NHR, $NR_2$, SR;

$R_3$ is F, Cl, Br, I, CN, $NO_2$, COR, COOH, CONHR, $CF_3$, $SnR_3$, or $R_3$ together with the benzene ring to which it is attached forms a fused ring system represented by the structure:

Z is $NO_2$, CN, COR, COOH, or CONHR;

Y is $CF_3$ F, Br, Cl, I, CN, or $SnR_3$;

Q is H, alkyl, halogen, $CF_3$, CN, $CR_3$, $SnR_3$, $NR_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OH, OR, COR, OCOR, $OSO_2R$, $SO_2R$, SR, SCN, NCS, OCN, NCO; or Q together with the benzene ring to which it is attached is a fused ring system represented by structure A, B or C:

A

B

C n is an integer of 1–4; and m is an integer of 1–3;

or its analog, isomer, metabolite, derivative, pharmaceutically acceptable salt, pharmaceutical product, N-oxide, hydrate or any combination thereof; or Formula VI:

VI wherein X is a bond, O, S, $SO_2$, $CH_2$, NH, NR, Se, PR, or NO;

Z is $NO_2$, CN, COR, COOH, or CONHR;

Y is $CF_3$, F, Br, Cl, I, CN, or $SnR_3$;

Q is $NR_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OR, COR, OCOR, $OSO_2R$, $SO_2R$ SR, SCN, NCS,

OCN, NCO; or Q together with the benzene ring to which it is attached is a fused ring system represented by structure A, B or C:

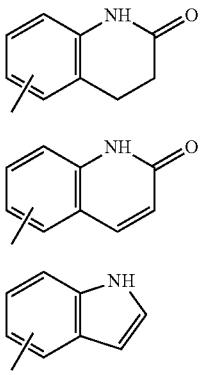

and R is alkyl, haloalkyl, dihaloalkyl, trihaloalkyl, CH$_2$F, CHF$_2$, CF$_3$, CF$_2$CF$_3$, aryl, phenyl, halogen, alkenyl or OH;

or its analog, isomer, metabolite, derivative, pharmaceutically acceptable salt, pharmaceutical product, N-oxide, hydrate or any combination thereof.

In another embodiment, the present invention provides a radiolabeled compound of formula II, which contains an analog, isomer, metabolite, derivative, pharmaceutically acceptable salt, pharmaceutical product, N-oxide, hydrate or any combination thereof of the SARM compound of any of formulas III–VI.

In one embodiment, the SARM compound is represented by the structure of formula III. In another embodiment, the SARM compound is represented by the structure of formula III wherein G is O. In another embodiment, the SARM compound is represented by the structure of formula III wherein X is O. In another embodiment, the SARM compound is represented by the structure of formula III wherein T is OH. In another embodiment, the SARM compound is represented by the structure of formula III wherein R$_1$ is CH$_3$. In another embodiment, the SARM compound is represented by the structure of formula III wherein Z is NO$_2$. In another embodiment, the SARM compound is represented by the structure of formula III wherein Z is CN. In another embodiment, the SARM compound is represented by the structure of formula III wherein Y is CF$_3$. In another embodiment, the SARM compound is represented by the structure of formula III wherein Q is NCS. In another embodiment, the SARM compound is represented by the structure of formula III wherein Q is NHCOCH$_3$. In another embodiment, the SARM compound is represented by the structure of formula III wherein Q is F.

In one embodiment, the SARM compound is represented by the structure of formula IV. In another embodiment, the SARM compound is represented by the structure of formula IV wherein G is O. In another embodiment, the SARM compound is represented by the structure of formula IV wherein X is O. In another embodiment, the SARM compound is represented by the structure of formula IV wherein T is OH. In another embodiment, the SARM compound is represented by the structure of formula IV wherein R$_1$ is CH$_3$. In another embodiment, the SARM compound is represented by the structure of formula IV wherein Z is NO$_2$. In another embodiment, the SARM compound is represented by the structure of formula IV wherein Z is CN. In another embodiment, the SARM compound is represented by the structure of formula IV wherein Y is CF$_3$. In another embodiment, the SARM compound is represented by the structure of formula IV wherein Q$_1$ is NCS. In another embodiment, the SARM compound is represented by the structure of formula IV wherein Q$_1$ is NHCOCH$_3$. In another embodiment, the SARM compound is represented by the structure of formula IV wherein Q$_1$ is F.

In one embodiment, the SARM compound is represented by the structure of formula V. In another embodiment, the SARM compound is represented by the structure of formula V wherein G is O. In another embodiment, the SARM compound is represented by the structure of formula V wherein X is O. In another embodiment, the SARM compound is represented by the structure of formula V wherein T is OH. In another embodiment, the SARM compound is represented by the structure of formula V wherein R$_1$ is CH$_3$. In another embodiment, the SARM compound is represented by the structure of formula V wherein Z is NO$_2$. In another embodiment, the SARM compound is represented by the structure of formula V wherein Z is CN. In another embodiment, the SARM compound is represented by the structure of formula V wherein Y is CF$_3$. In another embodiment, the SARM compound is represented by the structure of formula V wherein Q is NCS. In another embodiment, the SARM compound is represented by the structure of formula V wherein Q is NHCOCH$_3$. In another embodiment, the SARM compound is represented by the structure of formula V wherein Q is F.

In one embodiment, the SARM compound is represented by the structure of formula VI. In another embodiment, the SARM compound is represented by the structure of formula VI wherein X is O. In another embodiment, the SARM compound is represented by the structure of formula VI wherein Z is NO$_2$. In another embodiment, the SARM compound is represented by the structure of formula VI wherein Z is CN. In another embodiment, the SARM compound is represented by the structure of formula VI wherein Y is CF$_3$. In another embodiment, the SARM compound is represented by the structure of formula VI wherein Q is NCS. In another embodiment, the SARM compound is represented by the structure of formula VI wherein Q is NHCOCH$_3$. In another embodiment, the SARM compound is represented by the structure of formula VI wherein Q is F.

In one embodiment, the SARM compound of any of formulas III–VI is an androgen receptor ligand. In another embodiment, the SARM compound is an androgen receptor antagonist. In another embodiment, the SARM compound binds irreversibly to an androgen receptor. In another embodiment, the SARM compound is an alkylating agent. In another embodiment, the SARM compound is an androgen receptor antagonist which binds irreversibly to an androgen receptor.

In one embodiment, the radionuclide (RI) in formula II is a metallic radionuclide. In another embodiment, the radionuclide (RI) is a non-metallic radionuclide. In another embodiment, the radionuclide is $^{99}$Tc, $^{131}$I, $^{125}$I, $^{123}$I, $^{117}$Sn, $^{111}$In, $^{97}$Ru, $^{203}$Pb, $^{67}$Ga, $^{68}$Ga, $^{89}$Zr, $^{90}$Y, $^{177}$Lu, $^{149}$Pm, $^{153}$Sm, $^{166}$Ho, $^{131}$I, $^{32}$P, $^{211}$At, $^{47}$Sc, $^{109}$Pd, $^{105}$Rh, $^{186}$Re, $^{188}$Re, $^{60}$Cu, $^{62}$Cu, $^{64}$Cu, or $^{67}$Cu.

In one embodiment, the linker (Li) in formula II is a hydrocarbon chain, a carbohydrate, a cyclodextrin, an amino acid, a peptide, a polyalkylene glycol, or any combination thereof.

In one embodiment, the chelator (Ch) is formula II is a diaminedithiol, a monoamine-monoamide-dithiol, a triamide-monothiol, a monoamine-diamide-monothiol, a diaminedioxime, a cyclic or acyclic polyaminocarboxylate, or a hydrazine.

Furthermore, in one embodiment, the present invention provides a composition comprising the radiolabeled compound of formula I or II, and a pharmaceutically acceptable carrier. In another embodiment, the present invention provides a pharmaceutical composition comprising the radiolabeled compound of formula I or II, and a pharmaceutically acceptable carrier. In another embodiment, the present invention provides a pharmaceutical composition for use in medical therapy comprising the radiolabeled compound of formula I or II and a pharmaceutically acceptable carrier. In another embodiment, the present invention provides a pharmaceutical composition for use in medical diagnosis comprising the radiolabeled compound of formula I or II, and a pharmaceutically acceptable carrier.

Furthermore, in one embodiment, the present invention provides a method for imaging of cancer in a subject, comprising the steps of contacting an androgen receptor of the subject with a radiolabeled compound according of formula I or II, under conditions effective to bind the radiolabeled compound to the androgen receptor, and detecting the presence of the radiolabeled compound bound to the androgen receptor. In one embodiment, the cancer is prostate cancer. In another embodiment, the method comprises contacting the compound of formula I or II to the androgen receptor in vivo. In another embodiment, the method comprises contacting the compound of formula I or II to the androgen receptor in vitro. In one embodiment, the SARM compound binds irreversibly to the androgen receptor. In another embodiment, the SARM compound alkylates the androgen receptor.

Furthermore, in another embodiment, the present invention provides a method of imaging an androgen receptor-containing tissue in a subject comprising contacting an androgen receptor of the subject with a radiolabeled compound of formula I or II, under conditions effective to bind the radiolabeled compound to the androgen receptor, and detecting the presence of the radiolabeled compound bound to the androgen receptor. In one embodiment, the tissue is a prostate tissue. In another embodiment, the method comprises contacting the compound of formula I or II to the androgen receptor in vivo. In another embodiment, the method comprises contacting the compound of formula I or II to the androgen receptor in vitro. In another embodiment, the tissue is a prostate tissue. In one embodiment, the SARM compound binds irreversibly to the androgen receptor. In another embodiment, the SARM compound alkylates the androgen receptor.

Furthermore, in another embodiment, the present invention provides a method of in-vivo imaging in a subject, comprising the steps of administering to the subject a pharmaceutical composition comprising a radiolabeled compound of formula I or II, and detecting the presence of the radiolabeled compound in the patient. In one embodiment, the SARM compound binds irreversibly to the androgen receptor. In another embodiment, the SARM compound alkylates the androgen receptor.

Furthermore, in another embodiment, the present invention provides a method of treating a subject suffering from prostate cancer, the method comprising the steps of administering to the subject a pharmaceutical composition comprising the radiolabeled compound of formula I or II, in an amount effective to treat prostate cancer in the subject. In another embodiment, the method further comprises the step of administering to the subject a chemotherapeutic agent, a radiosensitizer agent, or a combination thereof. In one embodiment, the SARM compound binds irreversibly to the androgen receptor. In another embodiment, the SARM compound alkylates the androgen receptor.

Furthermore, in another embodiment, the present invention provides a method of delaying the progression of prostate cancer in a subject suffering from prostate cancer, comprising the step of administering to the subject a pharmaceutical composition comprising the radiolabeled compound of formula I or II, in an amount effective to delay the progression of prostate cancer in the subject. In another embodiment, the method further comprises the step of administering to the subject a chemotherapeutic agent, a radiosensitizer agent, or a combination thereof. In one embodiment, the SARM compound binds irreversibly to the androgen receptor. In another embodiment, the SARM compounds alkylate the androgen receptor.

Furthermore, in another embodiment, the present invention provides a method of preventing the recurrence of prostate cancer in a subject suffering from prostate cancer, comprising the step of administering to the subject a pharmaceutical composition comprising the radiolabeled compound of formula I or II, in an amount effective to prevent the recurrence of prostate cancer in the subject. In another embodiment, the method further comprises the step of administering to the subject a chemotherapeutic agent, a radiosensitizer agent, or a combination thereof. In one embodiment, the SARM compound binds irreversibly to the androgen receptor. In another embodiment, the SARM compounds alkylate the androgen receptor.

Furthermore, in another embodiment, the present invention provides a method of treating the recurrence of prostate cancer in a subject suffering from prostate cancer, comprising the step of administering to the subject a pharmaceutical composition comprising the radiolabeled compound of formula I or II, in an amount effective to treat the recurrence of prostate cancer in the subject. In another embodiment, the method further comprises the step of administering to the subject a chemotherapeutic agent, a radiosensitizer agent, or a combination thereof. In one embodiment, the SARM compound binds irreversibly to the androgen receptor. In another embodiment, the SARM compounds alkylates the androgen receptor.

The present invention further provides a method of producing a radiolabeled selective androgen receptor modulator (SARM) compound of formula I, comprising: providing a precursor compound represented by the structure of formula VII:

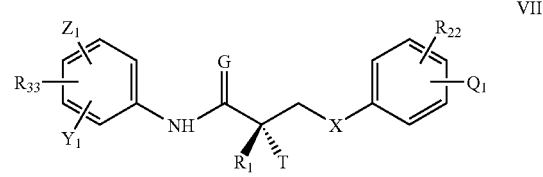

wherein X is a bond, O, S, $SO_2$, $CH_2$, NH, NR, Se, PR, or NO;

G is O or S;

T is OH, OR, —$NHCOCH_3$, or NHCOR;

R is alkyl, haloalkyl, dihaloalkyl, trihaloalkyl, $CH_2F$, $CHF_2$, $CF_3$, $CF_2CF_3$, aryl, phenyl, halogen, alkenyl or OH;

$R_1$ is $CH_3$, $CH_2F$, $CHF_2$, $CF_3$, $CH_2CH_3$, or $CF_2CF_3$;

$Z_1$ is a $NO_2$, CN, COR, COOH, or CONHR;

$Y_1$ is $CF_3$, F, Br, Cl, I, CN, or $SnR_3$;

$R_{33}$ is F, Cl, Br, I, OH, CN, $NO_2$, $NHCOCH_3$, $NHCOCF_3$, NHCOR, alkyl, arylalkyl, OR, $NH_2$, NHR, $NR_2$, SR; or $Z_1$, $Y_1$ and $R_{33}$ are independently of each other an isothiocyanate, an azide, a diazocarbonyl, a substituted oxirane, a β-chloroethylamine, a diazonium salt, a triazene group, a tertiary alkyl group, an oxy group, an alkoxy group, a stannoaLkyl group, a stannoaryl group, an unsubstituted or substituted boronic acid, an alkyl silane group, a pentaflourosilicate group, an alkylgermano group, a halomercury group, a trifluoroacetylthallate group, or a thallium difluoride group;

$Q_1$ is $CF_3$, CN, $CR_3$, $SnR_3$, $NR_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OR, COR, OCOR, $OSO_2R$, $SO_2R$, SR, SCN, NCS, OCN, NCO; or Q together with the benzene ring to which it is attached is a fused ring system represented by structure A, B or C:

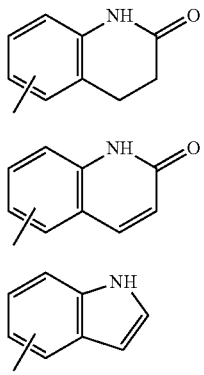

$R_{22}$ is nonradioactive F, Cl, Br, I, OH, CN, $NO_2$, $NHCOCH_3$, $NHCOCF_3$, NHCOR, alkyl, arylalkyl, OR, $NH_2$, NHR, $NR_2$, SR; or $Q_1$ and $R_{22}$ are independently of each other a diazonium salt, a triazene group, a tertiary alkyl amino group, a nitro group, an oxy or an alkoxy group, an amino or an alkylamino group, a stannoalkyl group ($SnAlk_3$), a stannoaryl group ($SnAr_3$), an unsubstituted or a substituted boronic acid, an alkyl silane group ($SiR_3$), a pentafluorosilicate ($SiF_5$) group, an alkylgermano group ($GeAlk_2$), a halomercury group (HgHal), a trifluoroacetyl thallate group, or a thallium difluoride group;

providing a radioactive compound; and reacting the precursor compound and the radioactive compound under conditions effective to produce a radiolabeled selective androgen receptor modulator (SARM) compound represented by the structure of formula I.

In one embodiment, the present invention provides a precursor compound of formula VII, useful in the preparation of the radiolabeled compounds of the present invention.

In one embodiment, $Y_1$ in compound VII is a stannoalkyl. In another embodiment, $Y_1$ in compound VII is $Sn(CH_3)_3$. In another embodiment, Y in compound VII is a radioactive halogen. In another embodiment, Y in compound VII is $^{125}I$.

The compounds of the present invention have an AR binding affinity several-fold greater than other nonsteroidal AR ligands and, accordingly, will bind and be retained in the AR in primary and metastatic tumor cells. In addition, the compounds of the present invention will, in one embodiment, irreversibly bind the androgen receptor, and in another embodiment, alkylate the androgen receptor. As such, they are useful in diagnosis, imaging, prevention and/or treatment of prostate cancer and other tissues containing androgen receptors.

DETAILED DESCRIPTION OF THE INVENTION

In one embodiment, this invention provides a class of radiolabeled androgen receptor targeting agents (ARTA). The agents define a new subclass of radiolabeled compounds, which are selective androgen receptor modulators (SARM) useful for prostate cancer imaging and in treating or preventing prostate cancer. The present invention further provides methods for a) imaging of cancer in a subject, b) imaging an androgen receptor-containing tissue in a subject, c) in-vivo imaging in a subject, d) treating a subject suffering from prostate cancer, e) delaying the progression of prostate cancer in a subject suffering from prostate cancer, f) preventing the recurrence of prostate cancer in a subject suffering from prostate cancer, and g) treating the recurrence of prostate cancer in a subject suffering from prostate cancer, which comprise using the radiolabeled compounds of the present invention.

In one embodiment, the present invention provides a radiolabeled selective androgen receptor modulator (SARM) compound represented by the structure of formula I:

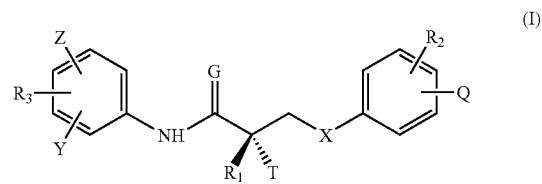

wherein X is a radioactive or nonradioactive O, S, $SO_2$, $CH_2$, NH, NR, Se, PR, or NO, or X is a bond;

G is a radioactive or nonradioactive O or S;

T is a radioactive or nonradioactive OH, OR, —NHCOCH$_3$, or NHCOR;

Z is a radioactive or a nonradioactive $NO_2$, CN, COR, COOH, or CONHR;

Y is a radioactive or a nonradioactive $CF_3$, F, Br, Cl, I, CN, or $SnR_3$;

Q is a radioactive or a nonradioactive alkyl, halogen, $CF_3$, CN, $CR_3$, $SnR_3$, $NR_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OR, COR, OCOR, $OSO_2R$, $SO_2R$, SR, SCN, NCS, OCN, NCO; or Q together with the benzene ring to which it is attached is a fused ring system represented by structure A, B or C:

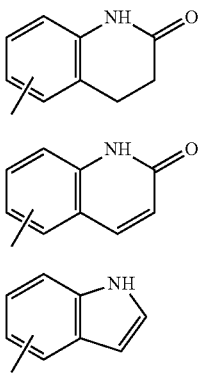

R is a radioactive or a nonradioactive alkyl, haloalkyl, dihaloalkyl, trihaloalkyl, $CH_2F$, $CHF_2$, $CF_3$, $CF_2CF_3$, aryl, phenyl, halogen, alkenyl or OH; and $R_1$ is a radioactive or nonradioactive $CH_3$, $CH_2F$, $CHF_2$, $CF_3$, $CH_2CH_3$, or $CF_2CF_3$;

$R_2$ is a radioactive or a nonradioactive F, Cl, Br, I, OH, CN, $NO_2$, $NHCOCH_3$, $NHCOCF_3$, NHCOR, alkyl, arylalkyl, OR, $NH_2$, NHR, $NR_2$, SR; and $R_3$ is a radioactive or a nonradioactive F, Cl, Br, I, CN, $NO_2$, COR, COOH, CONHR, $CF_3$, $SnR_3$;

wherein at least one of X, T, Z, Y, Q, R, $R_1$, $R_2$ or $R_3$ is radioactive.

In one embodiment, this invention provides an analog of the radiolabeled compound of formula I. In another embodiment, this invention provides a derivative of the radiolabeled compound of formula I. In another embodiment, this invention provides an isomer of the radiolabeled compound of formula I. In another embodiment, this invention provides a metabolite of the radiolabeled compound of formula I. In another embodiment, this invention provides a pharmaceutically acceptable salt of the radiolabeled compound of formula I. In another embodiment, this invention provides a pharmaceutical product of the radiolabeled compound of formula I. In another embodiment, this invention provides a hydrate of the radiolabeled compound of formula I. In another embodiment, this invention provides an N-oxide of the radiolabeled compound of formula I. In another embodiment, this invention provides a combination of any of an analog, derivative, metabolite, isomer, pharmaceutically acceptable salt, pharmaceutical product, hydrate or N-oxide of the radiolabeled compound of formula I.

In one embodiment, the present invention provides a radiolabeled compound of formula I wherein G is O. In one embodiment, the present invention provides a radiolabeled compound of formula I wherein X is O. In one embodiment, the present invention provides a radiolabeled compound of formula I wherein T is OH. In one embodiment, the present invention provides a radiolabeled compound of formula I wherein $R_1$ is $CH_3$. In another embodiment, Z the present invention provides a radiolabeled compound of formula I wherein is $NO_2$. In another embodiment, the present invention provides a radiolabeled compound of formula I wherein Z is CN. In another embodiment, the present invention provides a radiolabeled compound of formula I wherein Z is a radioactive halogen. In another embodiment, the present invention provides a radiolabeled compound of formula I wherein Z is a $^{125}I$. In another embodiment, the present invention provides a radiolabeled compound of formula I wherein Y is $CF_3$. In another embodiment, the present invention provides a radiolabeled compound of formula I wherein Y is a radioactive halogen. In another embodiment, the present invention provides a radiolabeled compound of formula I wherein Y is a $^{125}I$. In another embodiment, the present invention provides a radiolabeled compound of formula I wherein Q is $NHCOCH_3$. In another embodiment, the present invention provides a radiolabeled compound of formula I wherein Q is F. In another embodiment, the present invention provides a radiolabeled compound of formula I wherein Q is NCS. In another embodiment, the present invention provides a radiolabeled compound of formula I wherein Q is a radioactive halogen. In another embodiment, the present invention provides a radiolabeled compound of formula I wherein Q is a $^{125}I$. In another embodiment, the present invention provides a radiolabeled compound of formula I wherein $R_2$ is a radioactive halogen. In another embodiment, the present invention provides a radiolabeled compound of formula I wherein $R_2$ is a $^{125}I$. In another embodiment, the present invention provides a radiolabeled compound of formula I wherein $R_3$ is a radioactive halogen. In another embodiment, the present invention provides a radiolabeled compound of formula I wherein $R_3$ is a $^{125}I$.

In one embodiment, the present invention provides a radiolabeled compound of formula I wherein G is O, X is O, T is OH, $R_1$ is $CH_3$, Z is $NO_2$, Y is $CF_3$, and Q is $NHCOCH_3$. In another embodiment, the present invention provides a radiolabeled compound of formula I wherein G is O, X is O, T is OH, $R_1$ is $CH_3$, Z is $NO_2$, Y is a radioactive halogen, and Q is $NHCOCH_3$. In another embodiment, the present invention provides a radiolabeled compound of formula I wherein G is O, X is O, T is OH, $R_1$ is $CH_3$, Z is $NO_2$, Y is $^{125}I$, and Q is $NHCOCH_3$. In another embodiment, the present invention provides a radiolabeled compound of formula I wherein G is O, X is O, T is OH, $R_1$ is $CH_3$, Z is $NO_2$, Y is $CF_3$, and Q is F. In another embodiment, the present invention provides a radiolabeled compound of formula I wherein G is O, X is O, T is OH, $R_1$ is $CH_3$, Z is $NO_2$, Y is a radioactive halogen, and Q is F. In another embodiment, the present invention provides a radiolabeled compound of formula I wherein G is O, X is O, T is OH, $R_1$ is $CH_3$, Z is $NO_2$, Y is $^{125}I$, and Q is F. In another embodiment, the present invention provides a radiolabeled compound of formula I wherein G is O, X is O, T is OH, $R_1$ is $CH_3$, Z is $NO_2$, Y is $CF_3$, and Q is a radioactive halogen. In another embodiment, the present invention provides a radiolabeled compound of formula I wherein G is O, X is O, T is OH, $R_1$ is $CH_3$, Z is $NO_2$, Y is $CF_3$, and Q is $^{125}I$ The radiolabeled SARM compounds disclosed herein contain a radioisotope. The radioisotope can be chosen from a wide range of radioisotopes, including $^{123}I$, $^{125}I$, $^{131}I$, $^{18}F$, $^{19}F$, $^{77}Br$, $^{82}Br$ $^{14}C$, $^{3}H$, $^{14}C$, $^{35}S$ and the like. In one embodiment, the radioisotope is a radioactive halogen. In another embodiment, the radioisotope is $^{123}I$. In another embodiment, the radioisotope is $^{125}I$. In another embodiment, the radioisotope is $^{131}I$. In another embodiment, the radioisotope is $^{18}F$. In another embodiment, the radioisotope is $^{19}F$. In another embodiment, the radioisotope is $^{77}Br$. In another embodiment, the radioisotope is $^{78}Br$. In another embodiment, the radioisotope is $^{14}C$. In another embodiment, the radioisotope is $^{3}H$. In another embodiment, the radioisotope is $^{35}S$. Other radioisotopes useful for imaging are known to a person skilled in the art and can be incorporated into the radiolabeled SARM compounds of the present invention.

Table 1 shows nonlimiting examples of radiolabeled SARM compounds of formula I, in accordance with several embodiments of the present invention.

TABLE 1

| Radioisotope | Compound |
|---|---|
| $^{125}I$ | F₃C–(4-NO₂, 3-CF₃-phenyl)–NH–C(=O)–C(CH₃)(OH)–CH₂–O–(4-NHCOCH₃-phenyl), with $^{125}I$ on the nitro/trifluoromethyl phenyl ring |
| $^{3}H$ | Same scaffold, with $^{3}H$ on the nitro/trifluoromethyl phenyl ring |
| $^{125}I$ | Same scaffold, with $^{125}I$ on the acetamido phenyl ring |
| $^{3}H$ | Same scaffold, with $^{3}H$ on the acetamido phenyl ring |
| $^{125}I$ | Same scaffold, with $^{125}I$ replacing CF₃ on the nitro phenyl ring |
| $^{18}F$ | Same scaffold, with $^{18}F$ replacing CF₃ on the nitro phenyl ring |
| $^{125}I$ | Same scaffold, with $^{125}I$ replacing NHCOCH₃ on the second phenyl ring |
| $^{125}I$ | Amine-linked analog: (4-NO₂, 3-CF₃-phenyl)–NH–CH₂–C(CH₃)(OH)–CH₂–O–(4-F-phenyl), with $^{125}I$ on the nitro/trifluoromethyl phenyl ring |

TABLE 1-continued

| Radioisotope | Compound |
|---|---|
| $^3H$ | (structure: 3-CF₃, 4-NO₂, 3H-labeled phenyl-NH-C(=O)-C(CH₃)(OH)-CH₂-O-(4-F-phenyl)) |
| $^{125}I$ | (structure: 3-CF₃, 4-NO₂-phenyl-NH-C(=O)-C(CH₃)(OH)-CH₂-O-(4-F-phenyl with ¹²⁵I)) |
| $^3H$ | (structure: 3-CF₃, 4-NO₂-phenyl-NH-C(=O)-C(CH₃)(OH)-CH₂-O-(4-F-phenyl with ³H)) |
| $^{125}I$ | (structure: 3-¹²⁵I, 4-NO₂-phenyl-NH-C(=O)-C(CH₃)(OH)-CH₂-O-(4-F-phenyl)) |
| $^{18}F$ | (structure: 3-¹⁸F, 4-NO₂-phenyl-NH-C(=O)-C(CH₃)(OH)-CH₂-O-(4-F-phenyl)) |
| $^{18}F$ | (structure: 3-CF₃, 4-NO₂-phenyl-NH-C(=O)-C(CH₃)(OH)-CH₂-O-(4-¹⁸F-phenyl)) |
| $^{123}I$ | (structure: 3-CF₃, 4-NO₂, ¹²⁵I-phenyl-NH-C(=O)-C(CH₃)(OH)-CH₂-O-(4-NHCOCH₃-phenyl)) |
| $^{123}I$ | (structure: 3-CF₃, 4-NO₂-phenyl-NH-C(=O)-C(CH₃)(OH)-CH₂-O-(phenyl with ¹²⁵I and NHCOCH₃)) |
| $^{123}I$ | (structure: 3-¹²⁵I, 4-NO₂-phenyl-NH-C(=O)-C(CH₃)(OH)-CH₂-O-(4-NHCOCH₃-phenyl)) |

TABLE 1-continued

| Radioisotope | Compound |
|---|---|
| $^{123}I$ | 3-(trifluoromethyl)-4-nitroaniline linked via NH-C(=O)-C(CH$_3$)(OH)-CH$_2$-O- to 4-($^{125}$I)-phenyl |
| $^{123}I$ | 3-(trifluoromethyl)-4-nitro-($^{125}$I)-aniline linked via NH-CH$_2$-C(CH$_3$)(OH)-CH$_2$-O- to 4-fluorophenyl |
| $^{123}I$ | 3-(trifluoromethyl)-4-nitroaniline linked via NH-C(=O)-C(CH$_3$)(OH)-CH$_2$-O- to ($^{125}$I)-4-fluorophenyl |
| $^{123}I$ | 3-(trifluoromethyl)-4-nitroaniline linked via NH-C(=O)-C(CH$_3$)(OH)-CH$_2$-O- to 4-($^{123}$I)-phenyl |
| $^{125}I$ | 3-(trifluoromethyl)-4-nitro-($^{125}$I)-aniline linked via NH-C(=O)-C(CH$_3$)(OH)-CH$_2$-O- to 4-NC-phenyl |
| $^{123}I$ | 3-(trifluoromethyl)-4-nitro-($^{125}$I)-aniline linked via NH-C(=O)-C(CH$_3$)(OH)-CH$_2$-O- to 4-NC-phenyl |
| $^{131}I$ | 3-(trifluoromethyl)-4-nitro-($^{131}$I)-aniline linked via NH-C(=O)-C(CH$_3$)(OH)-CH$_2$-O- to 4-NC-phenyl |
| $^{3}H$ | 3-(trifluoromethyl)-4-nitro-($^{3}$H)-aniline linked via NH-C(=O)-C(CH$_3$)(OH)-CH$_2$-O- to 4-NC-phenyl |
| $^{125}I$ | 3-(trifluoromethyl)-4-nitroaniline linked via NH-C(=O)-C(CH$_3$)(OH)-CH$_2$-O- to ($^{125}$I)-4-NC-phenyl |

TABLE 1-continued
| Radioisotope | Compound |
|---|---|
| $^{123}$I | 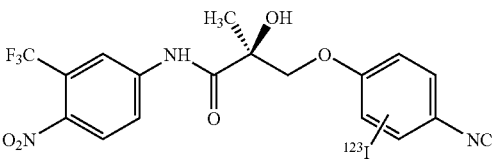 |
| $^{131}$I | 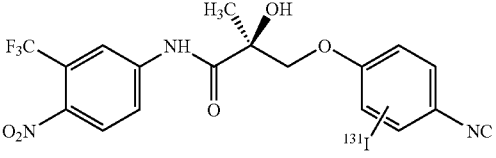 |
| $^{3}$H | 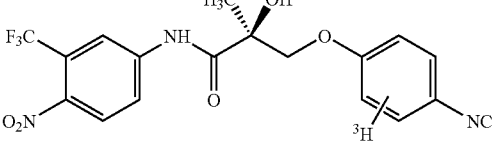 |
| $^{125}$I | 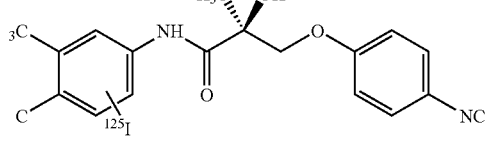 |
| $^{123}$I | 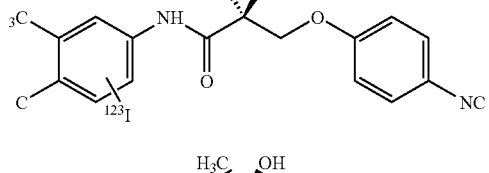 |
| $^{131}$I | 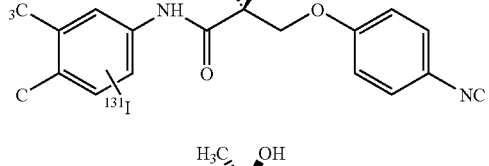 |
| $^{3}$H | 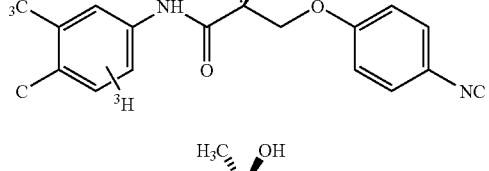 |
| $^{125}$I | 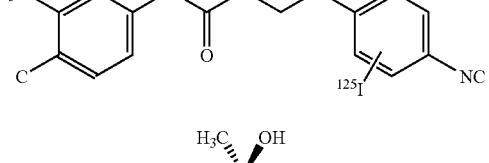 |
| $^{123}$I | 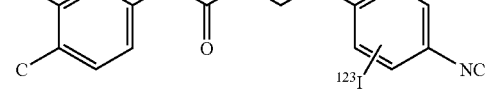 |

TABLE 1-continued

| Radioisotope | Compound |
|---|---|
| $^{131}I$ | 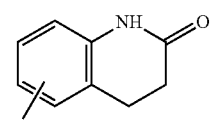 |
| $^3H$ | 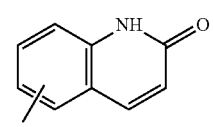 |

In another embodiment, the present invention provides a radiolabeled selective androgen receptor modulator (SARM) compound represented by the structure of formula II:

$$RI\text{-}(Ch)_n\text{-}(Li)_m\text{-}(SARM) \qquad II$$

wherein
  RI is a radioisotope;
  Ch is a metal chelator;
  Li is a linker moiety;
  m is 0 or 1;
  n is 0 or 1; and
  SARM is a selective androgen receptor modulator compound represented by the structure of any of formulas III–VI:

Formula III:

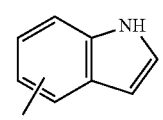

wherein
  G is O or S; X is a bond, O, S, $SO_2$, $CH_2$, NH, NR, Se, PR, or NO;
  T is OH, OR, —$NHCOCH_3$, or NHCOR
  Z is $NO_2$, CN, COOH, COR, NHCOR or CONHR;
  Y is $CF_3$, F, I, Br, Cl, CN, $CR_3$ or $SnR_3$;
  Q is alkyl, halogen, $CF_3$, CN, $CR_3$, $SnR_3$, $NR_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OR, COR, OCOR, $OSO_2R$, $SO_2R$, SR, SCN, NCS, OCN, NCO; or Q together with the benzene ring to which it is attached is a fused ring system represented by structure A, B or C:

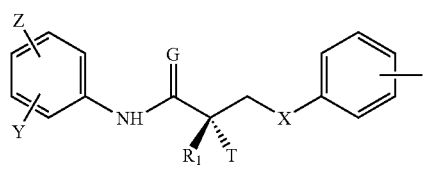

R is alkyl, haloalkyl, dihaloalkyl, trihaloalkyl, $CH_2F$, $CHF_2$, $CF_3$, $CF_2CF_3$, aryl, phenyl, halogen, alkenyl or OH; and
$R_1$ is $CH_3$, $CH_2F$, $CHF_2$, $CF_3$, $CH_2CH_3$, or $CF_2CF_3$;
or its analog, isomer, metabolite, derivative, pharmaceutically acceptable salt, pharmaceutical product, N-oxide, hydrate or any combination thereof;

Formula IV:

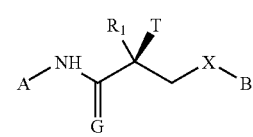

wherein X is a bond, O, $CH_2$, NH, Se, PR, NO or NR;
  G is O or S;
  $R_1$ is $CH_3$, $CH_2F$, $CHF_2$, $CF_3$, $CH_2CH_3$, or $CF_2CF_3$;
  T is OH, OR, —$NHCOCH_3$, or NHCOR;
  R is alkyl, haloalkyl, dihaloalkyl, trihaloalkyl, $CH_2F$, $CHF_2$, $CF_3$, $CF_2CF_3$, aryl, phenyl, halogen, alkenyl or OH;

A is a ring selected from:

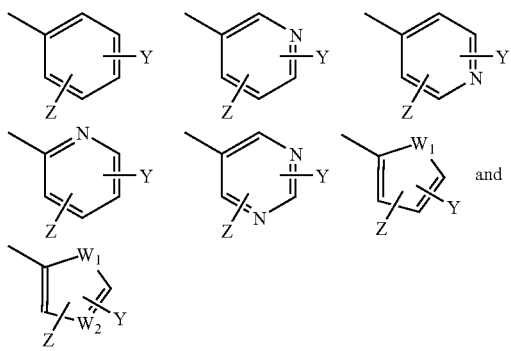

B is a ring selected from:

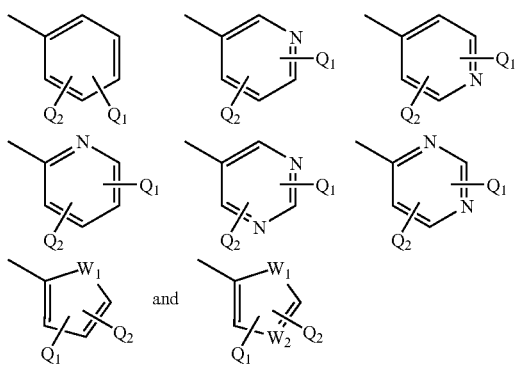

wherein A and B cannot simultaneously be a benzene ring;

Z is NO$_2$, CN, COOH, COR, NHCOR or CONHR;

Y is CF$_3$, F, I, Br, Cl, CN, CR$_3$ or SnR$_3$;

Q$_1$ and Q$_2$ are independently of each other a hydrogen, alkyl, halogen, CF$_3$, CN, CR$_3$, SnR$_3$, NR$_2$, NHCOCH$_3$, NHCOCF$_3$, NHCOR, NHCONHR, NHCOOR, OCONHR, CONHR, NHCSCH$_3$, NHCSCF$_3$, NHCSR, NHSO$_2$CH$_3$, NHSO$_2$R, OR, COR, OCOR, OSO$_2$R, SO$_2$R, SR, SCN, NCS, OCN, NCO,

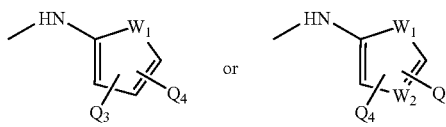

Q$_3$ and Q$_4$ are independently of each other a hydrogen, alkyl, halogen, CF$_3$, CN, CR$_3$, SnR$_3$, NR$_2$, NHCOCH$_3$, NHCOCF$_3$, NHCOR, NHCONHR, NHCOOR, OCONHR, CONHR, NHCSCH$_3$, NHCSCF$_3$, NHCSR, NHSO$_2$CH$_3$, NHSO$_2$R, OR, COR, OCOR, OSO$_2$R, SO$_2$R SR, SCN, NCS, OCN, or NCO;

W$_1$ is O, NH, NR, NO or S; and

W$_2$ is N or NO;

or its analog, isomer, metabolite, derivative, pharmaceutically acceptable salt, pharmaceutical product, N-oxide, hydrate or any combination thereof;

Formula V:

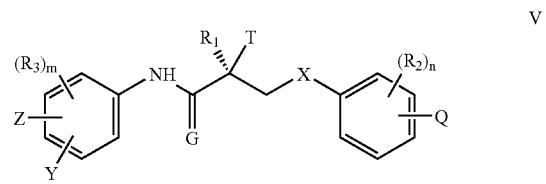

wherein X is a bond, O, S, SO$_2$, CH$_2$, NH, NR, Se, PR, or NO

G is O or S;

T is OH, OR, —NHCOCH$_3$, or NHCOR;

R is alkyl, haloaLkyl, dihaloalkyl, trihaloalkyl, CH$_2$F, CHF$_2$, CF$_3$, CF$_2$CF$_3$, aryl, phenyl, halogen, alkenyl or OH;

R$_1$ is CH$_3$, CH$_2$F, CHF$_2$, CF$_3$, CH$_2$CH$_3$, or CF$_2$CF$_3$;

R$_2$ is F, Cl, Br, I, CH$_3$, CF$_3$, OH, CN, NO$_2$, NHCOCH$_3$, NHCOCF$_3$, NHCOR, alkyl, arylalkyl, OR, NH$_2$, NHR, NR$_2$, SR;

R$_3$ is F, Cl, Br, I, CN, NO$_2$, COR, COOH, CONHR, CF$_3$, SnR$_3$, or R$_3$ together with the benzene ring to which it is attached forms a fused ring system represented by the structure:

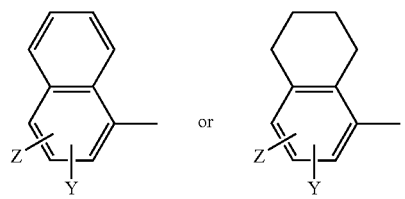

Z is NO$_2$, CN, COR, COOH, or CONHR;

Y is CF$_3$, F, Br, Cl, I, CN, or SnR$_3$;

Q is H, alkyl, halogen, CF$_3$, CN, CR$_3$, SnR$_3$, NR$_2$, NHCOCH$_3$, NHCOCF$_3$, NHCOR, NHCONHR, NHCOOR, OCONHR, CONHR, NHCSCH$_3$, NHCSCF$_3$, NHCSR, NHSO$_2$CH$_3$, NHSO$_2$R, OH, OR, COR, OCOR, OSO$_2$R, SO$_2$R, SR, SCN, NCS, OCN, NCO; or Q together with the benzene ring to which it is attached is a fused ring system represented by structure A, B or C:

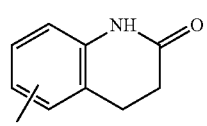

A

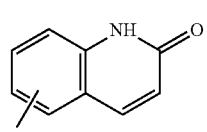

B

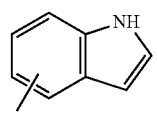

C n is an integer of 1–4; and m is an integer of 1–3;

or its analog, isomer, metabolite, derivative, pharmaceutically acceptable salt, pharmaceutical product, N-oxide, hydrate or any combination thereof; or Formula VI:

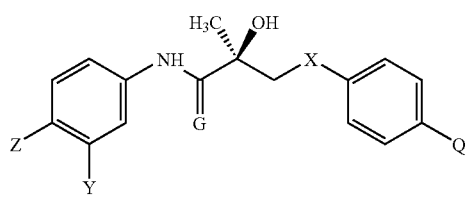

wherein X is a bond, O, S, $SO_2$, $CH_2$, NH, NR, Se, PR, or NO;

Z is $NO_2$, CN, COR, COOH, or CONHR,

Y is $CF_3$, F, Br, Cl, I, CN, or $SnR_3$;

Q is $NR_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OR, COR, OCOR, $OSO_2R$, $SO_2R$ SR, SCN, NCS, OCN, NCO; or Q together with the benzene ring to which it is attached is a fused ring system represented by structure A, B or C:

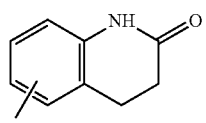

A

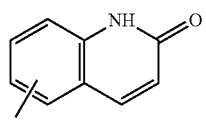

B

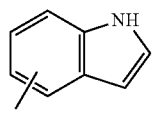

C and

R is alkyl, haloalkyl, dihaloalkyl, trihaloalkyl, $CH_2F$, $CHF_2$, $CF_3$, $CF_2CF_3$, aryl, phenyl, halogen, alkenyl or OH;

or its analog, isomer, metabolite, derivative, pharmaceutically acceptable salt, pharmaceutical product, N-oxide, hydrate or any combination thereof.

In another embodiment, the present invention provides a radiolabeled compound of formula I, which contains an analog, isomer, metabolite, derivative, pharmaceutically acceptable salt, pharmaceutical product, N-oxide, hydrate or any combination thereof of the SARM compound of any of formulas III–VI.

As contemplated herein, the radiolabeled compound represented by the structure of formula II comprises four moieties: A) SARM—a selective androgen receptor modulator moiety represented by the structure of any of formulas III–VI; B) RI—a radionuclide; C) Li—an optional linker moiety; and D) Ch—an optional chelator moiety.

A. Selective Androgen Receptor Modulator (SARM):

The SARM compound of any of formulas III–VI of the present invention belongs to a class of androgen receptor targeting agents (ARTA). The agents define a new subclass of compounds, which are selective androgen receptor modulators (SARM), which are for a) male contraception; b) treatment of a variety of hormone-related conditions, for example conditions associated with Androgen Decline in Aging Male (ADAM), such as fatigue, depression, decreased libido, sexual dysfunction, erectile dysfunction, hypogonadism, osteoporosis, hair loss, anemia, obesity, sarcopenia, osteopenia, osteoporosis, benign prostate hyperplasia, alterations in mood and cognition and prostate cancer; c) treatment of conditions associated with Androgen Decline in Female (ADIF), such as sexual dysfunction, decreased sexual libido, hypogonadism, sarcopenia, osteopenia, osteoporosis, alterations in cognition and mood, depression, anemia, hair loss, obesity, endometriosis, breast cancer, uterine cancer and ovarian cancer; d) treatment and/or prevention of chronic muscular wasting; e) decreasing the incidence of, halting or causing a regression of prostate cancer; f) imaging prostate cancer; g) oral androgen relacement and/or other clinical therpauetic and/or diagnostic areas.

In one embodiment, the SARM compound is represented by the structure of formula III.

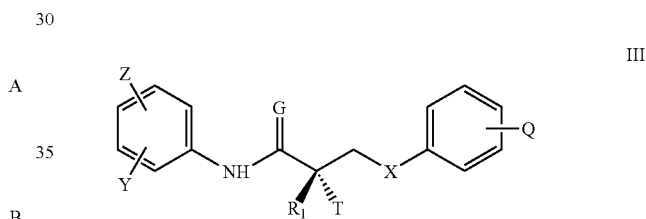

III wherein G is O or S;

X is a bond, O, S, $SO_2$, $CH_2$, NH, NR, Se, PR, or NO;

T is OH, OR, —$NHCOCH_3$, or NHCOR

Z is $NO_2$, CN, COOH, COR, NHCOR or CONHR;

Y is $CF_3$, F, I, Br, Cl, CN, $CR_3$ or $SnR_3$;

Q is alkyl, halogen, $CF_3$, CN, $CR_3$, $SnR_3$, $NR_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OR, COR, OCOR, $OSO_2R$, $SO_2R$, SR, SCN, NCS, OCN, NCO; or Q together with the benzene ring to which it is attached is a fused ring system represented by structure A, B or C:

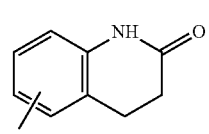

A

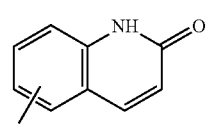

B

-continued

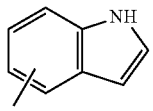
C

R is alkyl, haloalkyl, dihaloalkyl, trihaloalkyl, CH$_2$F, CHF$_2$, CF$_3$, CF$_2$CF$_3$, aryl, phenyl, halogen, alkenyl or OH; and R$_1$ is CH$_3$, CH$_2$F, CHF$_2$, CF$_3$, CH$_2$CH$_3$, or CF$_2$CF$_3$;

or its analog, isomer, metabolite, derivative, pharmaceutically acceptable salt, pharmaceutical product, N-oxide, hydrate or any combination thereof.

In one embodiment, the SARM compound is represented by the structure of formula III wherein G is O. In another embodiment, the SARM compound is represented by the structure of formula III wherein X is O. In another embodiment, the SARM compound is represented by the structure of formula III wherein T is OH. In another embodiment, the SARM compound is represented by the structure of formula III wherein R$_1$ is CH$_3$. In another embodiment, the SARM compound is represented by the structure of formula III wherein Z is NO$_2$. In another embodiment, the SARM compound is represented by the structure of formula III wherein Z is CN. In another embodiment, the SARM compound is represented by the structure of formula III wherein Y is CF$_3$. In another embodiment, the SARM compound is represented by the structure of formula III wherein Q is NCS. In another embodiment, the SARM compound is represented by the structure of formula III wherein Q is NHCOCH$_3$. In another embodiment, the SARM compound is represented by the structure of formula III wherein Q is F. In another embodiment, the SARM compound is represented by the structure of formula III wherein Q is in the para position. In another embodiment, the SARM compound is represented by the structure of formula III wherein Z is in the para position. In another embodiment, the SARM compound is represented by the structure of formula III wherein Y is in the meta position.

In one embodiment, the SARM compound is represented by the structure of formula IV:

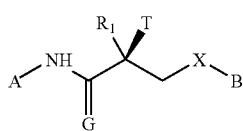
IV wherein X is a bond, O, CH$_2$, NH, Se, PR, NO or NR;
G is O or S;
R$_1$ is CH$_3$, CH$_2$F, CHF$_2$, CF$_3$, CH$_2$CH$_3$, or CF$_2$CF$_3$;
T is OH, OR, —NHCOCH$_3$, or NHCOR;
R is aLkyl, haloalkyl, dihaloalkyl, trihaloaLkyl, CH$_2$F, CHF$_2$, CF$_3$, CF$_2$CF$_3$, aryl, phenyl, halogen, alkenyl or OH;
A is a ring selected from:

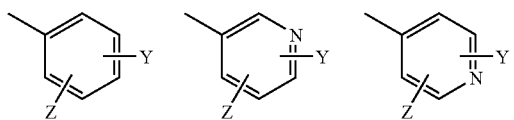

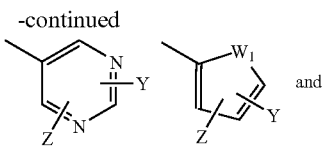

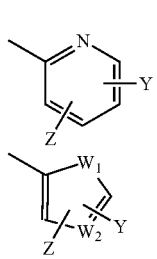

B is a ring selected from:

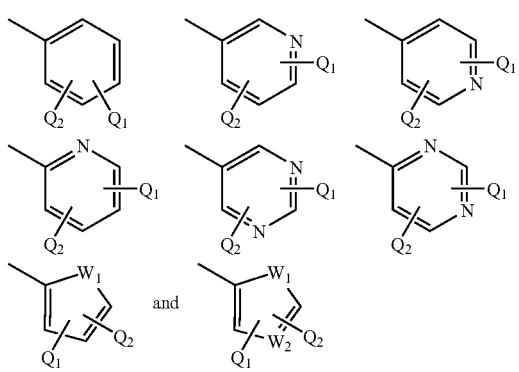

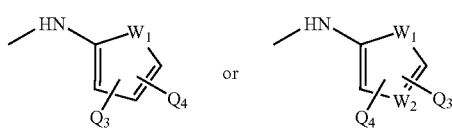

wherein A and B cannot simultaneously be a benzene ring;
Z is NO$_2$, CN, COOH, COR, NHCOR or CONHR;
Y is CF$_3$, F, I, Br, Cl, CN, CR$_3$ or SnR$_3$;
Q$_1$ and Q$_2$ are independently of each other a hydrogen, alkyl, halogen, CF$_3$, CN, CR$_3$, SnR$_3$, NR$_2$, NHCOCH$_3$, NHCOCF$_3$, NHCOR, NHCONHR, NHCOOR, OCONHR, CONHR, NHCSCH$_3$, NHCSCF$_3$, NHCSR, NHSO$_2$CH$_3$, NHSO$_2$R, OR, COR, OCOR, OSO$_2$R, SO$_2$R, SR, SCN, NCS, OCN, NCO, Q$_3$ and Q$_4$ are independently of each other a hydrogen, alkyl, halogen, CF$_3$, CN, CR$_3$, SnR$_3$, NR$_2$, NHCOCH$_3$, NHCOCF$_3$, NHCOR, NHCONHR, NHCOOR, OCONHR, CONHR, NHCSCH$_3$, NHCSCF$_3$, NHCSR, NHSO$_2$CH$_3$, NHSO$_2$R, OR, COR, OCOR, OSO$_2$R, SO$_2$R SR, SCN, NCS, OCN, or NCO;
W$_1$ is O, NH, NR, NO or S; and
W$_2$ is N or NO;

or its analog, isomer, metabolite, derivative, pharmaceutically acceptable salt, pharmaceutical product, N-oxide, hydrate or any combination thereof.

In another embodiment, the SARM compound is represented by the structure of formula IV wherein G is O. In another embodiment, the SARM compound is represented by the structure of formula IV wherein X is O. In another embodiment, the SARM compound is represented by the structure of formula IV wherein T is OH. In another embodiment, the SARM compound is represented by the structure of formula IV wherein R$_1$ is CH$_3$. In another embodiment, the SARM compound is represented by the structure of formula IV wherein Z is $NO_2$. In another embodiment, the SARM compound is represented by the structure of formula IV wherein Z is CN. In another embodiment, the SARM compound is represented by the structure of formula IV wherein Y is $CF_3$. In another embodiment, the SARM compound is represented by the structure of formula IV wherein $Q_1$ is NCS. In another embodiment, the SARM compound is represented by the structure of formula IV wherein $Q_1$ is $NHCOCH_3$. In another embodiment, the SARM compound is represented by the structure of formula IV wherein $Q_1$ is F.

In one embodiment, the SARM compound is represented by the structure of formula V:

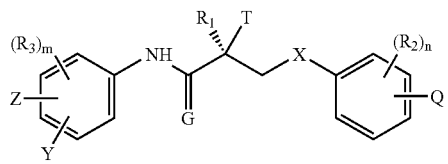

V wherein X is a bond, O, S, $SO_2$, $CH_2$, NH, NR, Se, PR, or NO

G is O or S;

T is OH, OR, —$NHCOCH_3$, or NHCOR;

R is alkyl, haloalkyl, dihaloalkyl, trihaloalkyl, $CH_2F$, $CHF_2$, $CF_3$, $CF_2CF_3$, aryl, phenyl, halogen, alkenyl or OH;

$R_1$ is $CH_3$, $CH_2F$, $CHF_2$, $CF_3$, $CH_2CH_3$, or $CF_2CF_3$;

$R_2$ is F, Cl, Br, I, $CH_3$, $CF_3$, OH, CN, $NO_2$, $NHCOCH_3$, $NHCOCF_3$, NHCOR, alkyl, arylalkyl, OR, $NH_2$, NHR, $NR_2$, SR;

$R_3$ is F, Cl, Br, I, CN, $NO_2$, COR, COOH, CONHR, $CF_3$, $SnR_3$, or $R_3$ together with the benzene ring to which it is attached forms a fused ring system represented by the structure:

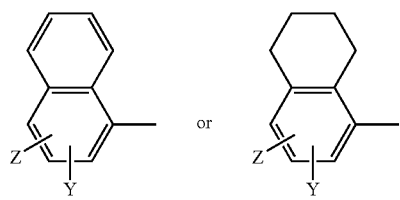

Z is $NO_2$, CN, COR, COOH, or CONHR;

Y is $CF_3$, F, Br, Cl, I, CN, or $SnR_3$;

Q is H, alkyl, halogen, $CF_3$, CN, $CR_3$, $SnR_3$, $NR_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OH, OR, COR, OCOR, $OSO_2R$, $SO_2R$, SR, SCN, NCS, OCN, NCO; or Q together with the benzene ring to which it is attached is a fused ring system represented by structure A, B or C:

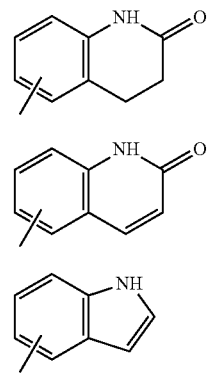

n is an integer of 1–4; and m is an integer of 1–3;

or its analog, isomer, metabolite, derivative, pharmaceutically acceptable salt, pharmaceutical product, N-oxide, hydrate or any combination thereof.

In another embodiment, the SARM compound is represented by the structure of formula V wherein G is O. In another embodiment, the SARM compound is represented by the structure of formula V wherein X is O. In another embodiment, the SARM compound is represented by the structure of formula V wherein T is OH. In another embodiment, the SARM compound is represented by the structure of formula V wherein $R_1$ is $CH_3$. In another embodiment, the SARM compound is represented by the structure of formula V wherein Z is $NO_2$. In another embodiment, the SARM compound is represented by the structure of formula V wherein Z is CN. In another embodiment, the SARM compound is represented by the structure of formula V wherein Y is $CF_3$. In another embodiment, the SARM compound is represented by the structure of formula V wherein Q is NCS. In another embodiment, the SARM compound is represented by the structure of formula V wherein Q is $NHCOCH_3$. In another embodiment, the SARM compound is represented by the structure of formula V wherein Q is F. In another embodiment, the SARM compound is represented by the structure of formula V wherein Q is in the para position. In another embodiment, the SARM compound is represented by the structure of formula V wherein Z is in the para position. In another embodiment, the SARM compound is represented by the structure of formula V wherein Y is in the meta position.

In one embodiment, the SARM compound is represented by the structure of formula VI.

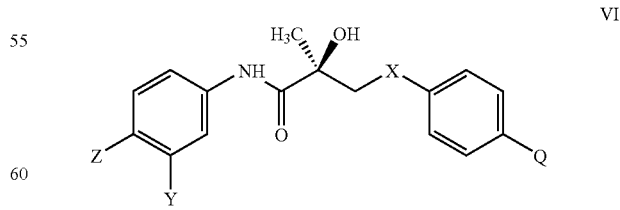

VI wherein X is a bond, O, S, $SO_2$, $CH_2$, NH, NR, Se, PR, or NO;

Z is $NO_2$, CN, COR, COOH, or CONHR;

Y is $CF_3$, F, Br, Cl, I, CN, or $SnR_3$;

Q is NR$_2$, NHCOCH$_3$, NHCOCF$_3$, NHCOR, NHCONHR, NHCOOR, OCONHR, CONHR, NHCSCH$_3$, NHCSCF$_3$, NHCSR, NHSO$_2$CH$_3$, NHSO$_2$R, OR, COR, OCOR, OSO$_2$R, SO$_2$R SR, SCN, NCS, OCN, NCO; or Q together with the benzene ring to which it is attached is a fused ring system represented by structure A, B or C:

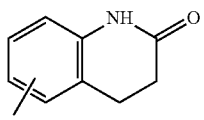

A

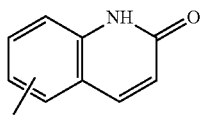

B

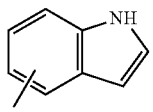

C and

R is alkyl, haloalkyl, dihaloalkyl, trihaloalkyl, CH$_2$F, CHF$_2$, CF$_3$, CF$_2$CF$_3$, aryl, phenyl, halogen, alkenyl or OH;

or its analog, isomer, metabolite, derivative, pharmaceutically acceptable salt, pharmaceutical product, N-oxide, hydrate or any combination thereof.

In another embodiment, the SARM compound is represented by the structure of formula VI wherein X is O. In another embodiment, the SARM compound is represented by the structure of formula VI wherein Z is NO$_2$. In another embodiment, the SARM compound is represented by the structure of formula VI wherein Z is CN. In another embodiment, the SARM compound is represented by the structure of formula VI wherein Y is CF$_3$. In another embodiment, the SARM compound is represented by the structure of formula VI wherein Q is NCS. In another embodiment, the SARM compound is represented by the structure of formula VI wherein Q is NHCOCH$_3$. In another embodiment, the SARM compound is represented by the structure of formula VI wherein Q is F.

The following definitions are used herein to define the SARM compounds provided herein.

The substituent R is defined herein as an alkyl, haloalkyl, dihaloalkyl, trihaloalkyl, CH$_2$F, CHF$_2$, CF$_3$, CF$_2$CF$_3$; aryl, phenyl, halogen, alkenyl, or hydroxyl (OH).

An "alkyl" group refers to a saturated aliphatic hydrocarbon, including straight-chain, branched-chain and cyclic alkyl groups. In one embodiment, the alkyl group has 1–12 carbons. In another embodiment, the alkyl group has 1–7 carbons. In another embodiment, the alkyl group has 1–6 carbons. In another embodiment, the alkyl group has 1–4 carbons. The alkyl group may be unsubstituted or substituted by one or more groups selected from halogen, hydroxy, alkoxy carbonyl, amido, alkylamido, dialkylamido, nitro, amino, alkylamino, dialkylamino, carboxyl, thio and thioalkyl.

A "haloalkyl" group refers to an alkyl group as defined above, which is substituted by one or more halogen atoms, e.g. by F, Cl, Br or I.

An "aryl" group refers to an aromatic group having at least one carbocyclic aromatic group or heterocyclic aromatic group, which may be unsubstituted or substituted by one or more groups selected from halogen, haloalkyl, hydroxy, alkoxy carbonyl, amido, alkylamido, dialkylamido, nitro, amino, alkylamino, dialkylamino, carboxy or thio or thioalkyl. Nonlimiting examples of aryl rings are phenyl, naphthyl, pyranyl, pyrrolyl, pyrazinyl, pyrimidinyl, pyrazolyl, pyridinyl, furanyl, thiophenyl, thiazolyl, imidazolyl, isoxazolyl, and the like.

A "hydroxyl" group refers to an OH group. An "alkenyl" group refers to a group having at least one carbon to carbon double bond. A halo group refers to F, Cl, Br or I.

An "arylalkyl" group refers to an alkyl bound to an aryl, wherein alkyl and aryl are as defined above. An example of an aralkyl group is a benzyl group.

Furthermore, as contemplated herein, the present invention encompasses a radiolabeled compound of formula II which contains an analog, derivative, isomer, metabolite, pharmaceutically acceptable salt, hydrate, N-oxide, or combinations thereof of the SARM moiety of any of formulas III–VI. In one embodiment, this invention provides a radiolabeled compound of formula II which contains an analog of the SARM moiety of any of formulas III–VI. In another embodiment, this invention provides a radiolabeled compound of formula II which contains a derivative of the SARM moiety of any of formulas III–IV. In another embodiment, this invention provides a radiolabeled compound of formula II which contains an isomer of the SARM moiety of any of formulas III–IV. In another embodiment, this invention provides a radiolabeled compound of formula II which contains a metabolite of the SARM moiety of any of formulas III–VI. In another embodiment, this invention provides a radiolabeled compound of formula II which contains a pharmaceutically acceptable salt of the SARM moiety of any of formulas III–VI. In another embodiment, this invention provides a radiolabeled compound of formula II which contains a pharmaceutical product of the SARM moiety of any of formulas III–VI. In another embodiment, this invention provides a radiolabeled compound of formula II which contains a hydrate of the SARM moiety of any of formulas III–VI. In another embodiment, this invention provides a radiolabeled compound of formula II which contains an N-oxide of the SARM moiety of any of formulas III–VI. In another embodiment, this invention provides a radiolabeled compound of formula I which contains a combination of any of an analog, derivative, metabolite, isomer, pharmaceutically acceptable salt, hydrate or N-oxide of the SARM moiety of any of formulas III–VI.

As defined herein, the term "isomer" includes, but is not limited to, optical isomers and analogs, structural isomers and analogs, conformational isomers and analogs, and the like.

In one embodiment, this invention encompasses the use of various optical isomers of the compound. It will be appreciated by those skilled in the art that the SARMs of the present invention contain at least one chiral center. Accordingly, the compounds used in the methods of the present invention may exist in, and be isolated in, optically-active or racemic forms. Some compounds may also exhibit polymorphism. It is to be understood that the present invention encompasses any racemic, optically-active, polymorphic, or stereroisomeric form, or mixtures thereof, which form possesses properties useful in the treatment of androgen-related conditions described herein. In one embodiment, the SARMs are the pure (R)-isomers. In another embodiment, the SARMs are the pure (S)-isomers. In another embodiment, the SARMs are a mixture of the (R) and the (S) isomers. In another embodiment, the SARMs are a racemic mixture comprising an equal amount of the (R) and the (S) isomers. It is well known in the art how to prepare optically-active forms (for example, by resolution of the racemic form by recrystallization techniques, by synthesis from optically-active starting materials, by chiral synthesis, or by chromatographic separation using a chiral stationary phase).

The invention includes pharmaceutically acceptable salts of amino-substituted compounds with organic and inorganic acids, for example, citric acid and hydrochloric acid. The invention also includes N-oxides of the amino substituents of the compounds described herein. Pharmaceutically acceptable salts can also be prepared from the phenolic compounds by treatment with inorganic bases, for example, sodium hydroxide. Also, esters of the phenolic compounds can be made with aliphatic and aromatic carboxylic acids, for example, acetic acid and benzoic acid esters.

This invention further includes derivatives of the SARM compounds. The term "derivatives" includes but is not limited to ether derivatives, acid derivatives, amide derivatives, ester derivatives and the like. In addition, this invention further includes hydrates of the SARM compounds. The term "hydrate" includes but is not limited to hemihydrate, monohydrate, dihydrate, trihydrate and the like.

This invention further includes metabolites of the SARM compounds. The term "metabolite" means any substance produced from another substance by metabolism or a metabolic process.

This invention further includes pharmaceutical products of the SARM compounds. The term "pharmaceutical product" means a composition suitable for pharmaceutical use (pharmaceutical composition), as defined herein.

B. Radionuclide (RI)

Radionuclides are radioactive isotopes that are included in radiopharmaccutical therapeutic agents and/or diagnostic agents. The radionculide ($R_1$) serves as the radiation source. The radiopharmaceutical agents are routinely used in nuclear medicine for the diagnosis and/or therapy of various diseases. The in vivo diagnostic information is obtained by, for example, intravenous injection of the radiopharmaccutical and the subsequent determination of the biodistribution using a gamma camera. The biodistribution of the radiopharmaceutical, which depends on the physical and chemical properties of the radiopharmaceutical, can be used to obtain information about the presence, progression, and/or the state of the disease and/or in the alternative to treat or prevent a disease.

As contemplated herein, the term "radionuclide" includes metallic and non-metallic radionuclides. The radionuclide is chosen based on the medical application of the radiolabeled pharmaceutical agents (i.e. therapeutic applications or diagnostic applications of AR-associated conditions). When the radionuclide is a metallic radionuclide, a chelator is typically employed to bind the metallic radionuclide to the rest of the molecule. When the radionuclide is a non-metallic radionuclide, the non-metallic radionuclide is typically linked directly, or via a linker, to the rest of the molecule.

As used herein, a "metallic radionuclide" is any suitable metallic radionuclide (metallic radioisotope) useful in a therapeutic or diagnostic procedure in vivo or in vitro. The metallic radionuclide can be a metallic radioisotope that emits alpha particles, beta particles, gamma rays, positrons, and the like.

The radiolabeled compounds of formula I of the present invention that include a gamma ray emitting isotope or positron emitting isotope are useful as Androgen Receptor (AR) imaging agents. The radiolabeled compounds of formula I of the present invention that include a beta particle, or alpha particle emitting isotope are useful as therapeutic radiopharmaceuticals for AR-associated diseases.

Suitable metallic radionuclides include, but are not limited to: Antimony-124, Antimony-125, Arsenic-74, Barium-103, Barium-140, Beryllium-7, Bismuth-206, Bismuth-207, Bismuth212, Cadmium-109, Cadmium-115m, Calcium-45, Cerium-139, Cerium-141, Cerium-144, Cesium-137, Chromium-51, Cobalt-55, Cobalt-56, Cobalt-57, Cobalt-58, Cobalt-60, Cobalt-64, Copper-60, Copper-62, Copper-64, Copper-67, Erbium-169, Europium-152, Gallium-64, Gallium-67, Gallium-68, Gadolinium153, Gadolinium-157 Gold-195, Gold-199, Hafnium-175, Hafnium-175-181, Holmium-166, Indium-110, Indium-111, Iridium-192, Iron-55, Iron-59, Krypton85, Lead-203, Lead-210, Lutetium-177, Manganese-54, Mercury-197, Mercury203, Molybdenum-99, Neodymium-147, Neptunium-237, Nickel-63, Niobium95, Osmium-185+191, Palladium-103, Palladium-109, Platinum-195m, Praseodymium-143, Promethium-147, Promethium-149, Protactinium-233, Radium-226, Rhenium-186, Rhenium-188, Rubidium-86, Ruthenium-97, Ruthenium-103, Ruthenium-105, Ruthenium-106, Samarium-153, Scandium-44, Scandium-46, Scandium-47, Selenium-75, Silver-110m, Silver-111, Sodium-22, Strontium-85, Strontium-89, Strontium-90, Sulfur-35, Tantalum-182, Technetium-99m, Tellurium-125, Tellurium-132, Thallium-204, Thorium-228, Thorium-232, Thallium-170, Tin-113, Tin-114, Tin-117m, Titanium-44, Tungsten-185, Vanadium-48, Vanadium-49, Ytterbium-169, Yttrium-86, Yttrium-88, Yttrium-90, Yttrium-91, Zinc-65, Zirconium-89, and Zirconium-95.

As used herein, a "non-metallic radionuclide" is any suitable nonmetallic radionuclide (non-metallic radioisotope) useful in a therapeutic or diagnostic procedure in vivo or in vitro. The non-metallic radioisotope can emit alpha particles, beta particles, gamma rays, positrons, and the like. The radiolabeled compounds of formula I of the present invention that include a gamma ray emitting isotope or positron emitting isotope are useful as AR imaging agents. The radiolabeled compounds of formula I of the present invention that include a beta particle, or alpha particle emitting isotope are useful as therapeutic radiopharmaceuticals for AR-associated diseases.

The non-metallic radioisotope can be covalently attached either directly to the SARM compound of the present invention, or through a linker (Li).

Suitable non-metallic radionuclides include, but are not limited to: Iodine-131, Iodine-125, Iodine-123, Phosphorus-32, Astatine-211, Fluorine-18, Carbon-11, Oxygen-15, Bromine-76, and Nitrogen-13.

The selection of radionuclide depends on the intended medical use (e.g., diagnostic or therapeutic) of the radiopharmaceutical agent.

Radionuclides, such as $^{99m}Tc$ $^{131}I$, 123L $^{117m}Sn$, $^{111}In$, $^{97}Ru$, $^{203}Pb$, $^{67}Ga$, $^{68}Ga$, $^{89}Zr$, and $^{64}Cu$, are suitable for diagnostic imaging. The majority of radiopharmaceuticals used in nuclear medicine are $^{99m}Tc$-labeled compounds. The reason for such a preeminent position of $^{99}mTc$ in clinical use is its extremely favorable physical and nuclear characteristics. The 6 h half-life is long enough to allow a radiochemist to carry out radiopharmaceutical synthesis and for nuclear medicine practitioners to collect useful images. At the same time, it is short enough to permit the administration of millicurie amounts of $^{99m}Tc$ radioactivity without significant radiation dose to the patient. The monochromatic 140 KeV photons are readily collimated to give images of superior spatial resolution. Furthermore, $^{99m}$Tc is readily available from commercial $^{99}$Mo-$^{99m}$Tc generators at low cost.

Radionuclides, such as $^{90}$Y, $^{177}$Lu, $^{149}$Pm, $^{153}$sm, $^{166}$Ho, $^{131}$I, $^{32}$P, $^{211}$At, $^{47}$Sc, $^{109}$Pd, $^{105}$Rh, $^{186/188}$Re, and $^{67}$Cu, are potentially useful for radiotherapy. Among these therapeutic radionuclides, lanthanide radioisotopes are of particular interest. There are several lanthanide isotopes to choose, including low energy beta-emitter Lu, medium energy beta-emitters, $^{149}$Pm and $^{153}$Sm, and high-energy beta-emitters, $^{166}$Ho and $^{90}$Y. Yttrium and lanthanide metals share similar coordination chemistry. The chelator technology and their coordination chemistry are well developed and well understood.

Rhenium has two isotopes ($^{186}$Re and $^{188}$Re), which might be useful in tumor therapy. $^{186}$Re has a half-life of 3.68 d with p-emission (Emax=1.07 MeV, 91% abundance) and a gamma-photon (E=137 keV, 9% abundance), which should allow imaging during therapy. $^{188}$Re has a half-life of 16.98 h with an intense α-emission (Emax=2.12 MeV, 85% abundance) and 155 keV gamma photons (15% abundance). The related chemistry, medical applications, and antibody labeling with $^{186/188}$Re by direct and indirect methods have recently been reviewed. Griffith, G. L., Goldenberg, D. M., Jones, A. L., Hansen, H., *J. Bioconjugate Chem*. (1992), 3, 91–99; and Fritzberg, A. R., Berninger, R. W., Badley, S. W., Wester, D. W.; *Pharmaceutical Res*. (1988), 5, 325–334. Due to the periodic relationship, rhenium chemistry is very similar to technetium chemistry. As such, the methods used for labeling with $^{99m}$Tc should apply to that with 186/188Re.

Identifying the most appropriate isotope for radiotherapy requires weighing a variety of factors. These include tumor uptake and retention, blood clearance, rate of radiation delivery, half-life and specific activity of the radionuclide, and the feasibility of large-scale production of the radionuclide in an economical fashion. The key point for a therapeutic radiopharmaceutical is to deliver the requisite amount of radiation dose to the tumor cells and to achieve a cytotoxic or tumoricidal effect while not causing unmanageable side-effects.

The physical half-life of the therapeutic radionuclide should match the biological half-life of the radiopharmaceutical at the tumor site. If the half-life of the radionuclide is too short, much of the decay will have occurred before the radiopharmaceutical has reached maximum target/background ratio. On the other hand, too long a half-life would cause unnecessary radiation dose to normal tissues. Ideally, the radionuclide should have a long enough half-life to attain a minimum dose rate and to irradiate all the cells during the most radiation sensitive phases of the cell cycle. In addition, the half-life of a radionuclide has to be long enough to allow adequate time for manufacturing, release, and transportation.

Other practical considerations in selecting a radionuclide for a given application in tumor therapy are availability and quality. The purity has to be sufficient and reproducible, as trace amounts of impurities can affect the radiolabeling and radiochemical purity of the radiopharmaceutical.

The target receptor sites in tumors are typically limited in number. This requires that the chosen radionuclide have high specific activity. The specific activity depends primarily on the production method. Trace metal contaminants must be minimized as they often compete with the radionuclide for the chelator and their metal complexes compete for receptor binding with the radiolabeled chelated agent For tumor therapy, both α and β-emitters have been investigated. Alpha particles are particularly good cytotoxic agents because they dissipate a large amount of energy within one or two cell diameters. Most α-emitters are heavy elements that decay to hazardous by-products and their penetration range is limited to only 50 μm in tissue. The short-ranged particle emitters are more attractive if the radiopharmaceutical is internalized into tumor cells. The β-particle emitters have relatively long penetration range (2–12 mm in the tissue) depending the energy level. The long-range penetration is particularly important for solid tumors that have heterogeneous blood flow and/or receptor expression. The β-particle emitters yield a more homogeneous dose distribution even when they are heterogeneously distributed within the target tissue.

Depending on the tumor size and location, the choice of the β-emitter may be different. For example, medium or low energy β-emitters such as $^{153}$Sm and $^{177}$Lu are better for smaller metastases while high-energy β-emitters such as $^{90}$Y are used for larger tumors.

C. Linker (Li)

As contemplated herein, the radiolabeled compounds of formula I of the present invention contain an optional linker (Li) which links the radionuclide (RI) to the SARM compound of any of formulas II–V. When RI is a metallic radionuclide, a metal chelator (Ch) is typically present, and in this particular embodiment, the linker (Li) links the complexed (chelated) radionuclide (RI) to the SARM compound of any of formulas II–V. When RI is a non-metallic radionuclide, the metal chelator (Ch) is typically absent, and in this particular embodiment, the linker (Li) links the radionuclide (RI) to the SARM compound of any of formulas II–V.

In one embodiment, the radiolabeled compound of formula I does not contain a linker (formula I, m=0). In accordance with this particular embodiment, the radiolabeled compound of formula I contains a radionuclide (RI), which is linked directly to the SARM of any of formula II–V. When RI is a metallic radionuclide, a metal chelator (Ch) is typically present, and the complexed (chelated) radionuclide (Ch-RI) is directly linked to the SARM of any of formulas II–V (formula I, m=0, n=1). Alternatively, when RI is a non-metallic radionuclide, the metal chelator (Ch) is typically absent and the radionuclide (RI) is directly linked to the SARM of any of formulas II–V (formula I, m=0, n=1).

In another embodiment, the radiolabeled compound of formula I does contain a linker (Li) (formula I, m=1). In accordance with this particular embodiment, the radiolabeled compound of formula I contains a radionuclide (RI), which is linked to the SARM of any of formulas II–V via linker (Li). When RI is a metallic radionuclide, a metal chelator (Ch) is typically present, and the complexed (chelated) radionuclide (Ch-RI) is linked to the SARM of any of formulas II–V via linker (Li) (formula I, m=1, n=1). Alternatively, when RI is a non-metallic radionuclide, the metal chelator (Ch) is typically absent and the radionuclide (RI) is linked to the SARM of any of formulas II–V via a linker (Li) (formula I, m=1, n=1).

The linking group (Li) can serve several roles. First, the linking group (Li) can provide a spacing group between the radionuclide (RI) and the SARM of any of formulas II–V. In one embodiment, when the radionuclide (RI) is a non-metallic radionuclide and the metal chelator (Ch) is typically absent, the linking group (Li) can provide a spacing group between the radionuclide (RI) and the SARM of any of formulas II–V. In another embodiment, when the radionuclide (RI) is a non-metallic radionuclide and the metal chelator (Ch) is typically present, the linking group (Li) can provide a spacing group between the complexed radionuclide (Ch-RI) metal chelator (Ch), and the SARM of any of formulas II–V. The spacing group can minimize the possibility that the radionuclide (RI) (e.g., non-metallic radionuclide or metallic radionuclide) will interfere with the interaction of the SARM compound with its biological target (i.e. the androgen receptor).

The necessity of incorporating a linking group (Li) in the radiolabeled compound of formula I is dependent on the identity of the SARM, the radionuclide (RI), and the metal chelator (Ch), if present. For example, if the radionuclide (RI) and the optional metal chelator (Ch) cannot be attached to the SARM without substantially diminishing the SARM's affinity for the androgen receptor, then a suitable linking group can be used.

A linking group (Li) can also provide a means of independently attaching multiple SARMs to one metal chelator, wherein the metal chelator chelates one or more radionuclides.

A number of different moieties can be used as the linking group (Li). In one embodiment, the linker (Li) is a carbohydrate. In another embodiment, the linker (Li) is a cyclodextrin. In another embodiment, the linker (Li) is a polyalkylene glycol. In another embodiment, the linker (Li) is an amino acid. In another embodiment, the linker (Li) is a peptide (or other polyamino acid) chain. In another embodiment, the linker (Li) is a poly (ethylene glycol) (PEG) chain.

The length of the linker may vary, and depends on the specific compound. Suitable lengths for the linker moiety is 1–50 angstroms, for example 5 angstroms, 10 angstroms, 15 angstroms 20 angstroms, 25 angstroms, 30 angstroms, 35 angstroms, 40 angstroms, 45 angstroms, 50 angstroms, and the like.

The linker, if present, can typically be a simple hydrocarbon chain, a carbohydrate, a cyclodextrin, a long poly alkylene glycol chain (for example a polyethylene glycol (PEG) chain), an amino acid, or a peptide (for example a poly anionic or cationic peptide sequence). Sometimes, a metabolizeable linker is used to increase the blood clearance and to reduce the background activity, thereby improving the target-to-background ratio.

D. Metal Chelator (Ch)

As used herein, the "metal chelator" (Ch) is employed to bind the metallic radionuclide to the SARM radiolabeled compound of formula I. When the radioisotope (RI) is a metallic radionuclide, the metal chelator (Ch) is typically present (formula I n=1). When the radioisotope (RI) is a non-metallic radionuclide, the metal chelator (Ch) is typically absent (formula I n=0).

Suitable metal chelator are disclosed, e.g., in Volkert, W. A. and Hoffman, T., *J. Chem. Rev.* (1999), 99, 2269–2292; Meeg, M. J. and Jurisson, S., *Acc. Chem. Res.* (1999), 32, 1053–1060; Kiu, S. And Edwards, D. S., *Chem. Rev*, (1999), 99, 2235–2268; Anderson, C. J. and Welch, M., *J. Chem. Rev.* (1999), 99, 2219–2234.

The metal chelator (Ch) is chosen based on the medical application of the radiolabeled compound (i.e. diagnostic or therapeutic application), and is selected to form stable complexes with the metallic radionuclide (RI). Metal chelators for diagnostic radiopharmaceuticals are selected to form stable complexes with the metallic radionuclides that have imageable gamma ray or positron emissions. Metal chelators for therapeutic radiopharmaceuticals are selected to form stable complexes with the metallic radioisotopes that have alpha particle or beta particle emissions.

For example, metal chelators for technetium, copper and gallium isotopes are typically diaminedithiols, monoamine-monoamidedithiols, triamide-monothiols, monoanmine-diamide-monothiols, diaminedioximes, or hydrazines. These metal chelators are generally tetradentate with donor atoms typically being nitrogen, oxygen or sulfur. These metal chelators will preferably have amine nitrogen and thiol sulfur donor atoms and hydrazine bonding units.

The thiol sulfur atoms and the hydrazines may bear a protecting group which can be displaced either prior to using the reagent to synthesize the radiolabeled compounds of the present invention. Alternatively, the protecting group may be removed in situ during the synthesis of the radiolabeled compounds of the present invention.

Non-limiting examples of thiol protecting groups include those listed in Greene and Wuts, Protective Groups in Organic Synthesis, John Wiley & Sons, New York, 3rd Ed., 1999. Any thiol protecting group known in the art can be used. Examples of thiol protecting groups include, but are not limited to acetamidomethyl, benzamidomethyl, 1-ethoxyethyl, benzoyl, triphenylmethyl, and the like.

Non-limiting examples of hydrazine protecting groups are hydrazones which can be aldehyde or ketone hydrazones substituted with one or more alkyl, aryl and/or heterocycle. In one embodiment, the hydrazine, when bound to the metallic radionuclide (RI), is termed a hydrazido or diazenido group and serves as the point of attachment of the radionuclide (RI) to the remainder of the radiolabeled compound of formula I.

Metal chelators for yttrium, bismuth, and the lanthanide isotopes typically include cyclic and acyclic polyaminocarboxylates such as DTPA, DOTA, D03A, 2-benzyl-DOTA, alpha-(2-phenethyl) 1,4,7,10tetraazacyclododecane-1-acetic-4,7,10-tris (methylacetic) acid, 2-benzylcyclohexyldiethylenetriaminepentaacetic acid, 2-benzyl-6-methyl-DTPA, and 6,6"-bis[N,N,N",N"-tetra(carboxymethyl)aminomethyl)-4'-(3-amino-4methoxyphenyl)-2,2':6',2"-terpyridine. Procedures for synthesizing these metal chelators can be found, e g., in Brechbiel, M. and Gansow, O., *J. Chem. Soc. Perkin Trans*. (1992), 1, 1175; Brechbiel, M. and Gansow, O., *Bioconjugate Chem*. (1991), 2, 187; Deshpande, S., et. al., *J. Nucl. Med*. (1990), 31, 473; Kruper, J., U.S. Pat. No. 5,064,956, and Toner, J., U.S. Pat. No. 4,859,777.

Metal chelators for rhenium, copper, palladium, platinum, iridium, rhodium, silver and gold isotopes typically include diaminedithiols, monoamine-monoamidedithiols, triamide-monothiols, monoamine-diamidemonothiols, diaminedioximes, and hydrazines.

Biological Activity of SARM Compounds

The biological activity of the SARM compounds of the invention is best understood through a discussion of receptors and signal transduction pathways. Cells in higher animals normally communicate by means of hundreds of kinds of extracellular signaling molecules, including proteins, small peptides, amino acids, nucleotides, steroids, retinoids, fatty acid derivatives, and even dissolved gases such as nitric oxide and carbon monoxide. These signaling molecules relay a "signal" to another cell (a "target cell"), generally affecting a cellular function. As used herein, receptors for extracellular signaling molecules are collectively referred to as "cell signaling receptors".

Many cell signaling receptors are transmembrane proteins on a cell surface; when they bind an extracellular signaling molecule (i.e., a ligand), they become activated so as to generate a cascade of intracellular signals that alter the behavior of the cell. In contrast, in some cases, the receptors are inside the cell and the signaling ligand has to enter the cell to activate them; these signaling molecules therefore must be sufficiently small and hydrophobic to diffuse across the plasma membrane of the cell. As used herein, these receptors are collectively referred to as "intracellular cell signaling receptors".

Steroid hormones are one example of small hydrophobic molecules that diffuse directly across the plasma membrane of target cells and bind to intracellular cell signaling receptors. These receptors are structurally related and constitute the intracellular receptor superfamily (or steroid-hormone receptor superfamily). Steroid hormone receptors include progesterone receptors, estrogen receptors, androgen receptors, glueocorticoid receptors, and mineralocorticoid receptors. The present invention is particularly directed to androgen receptors.

In addition to ligand binding to the receptors, the receptors can be blocked to prevent ligand binding. When a substance binds to a receptor, the three-dimensional structure of the substance fits into a space created by the three-dimensional structure of the receptor in a ball and socket configuration. The better the ball fits into the socket, the more tightly it is held. This phenomenon is called affinity. If the affinity of a substance is greater than the original hormone, it will compete with the hormone and bind the binding site more frequently. Once bound, signals may be sent through the receptor into the cells, causing the cell to respond in some fashion. This is called activation. On activation, the activated receptor then directly regulates the transcription of specific genes. But the substance and the receptor may have certain attributes, other than affinity, in order to activate the cell. Chemical bonds between atoms of the substance and the atoms of the receptors may form. In some cases, this leads to a change in the configuration of the receptor, which is enough to begin the activation process (called signal transduction). As a result, substances can be made which bind receptors and activate them (called receptor agonists) or inactivate them (called receptor antagonists).

In one embodiment, the SARM compound of formula II is an androgen receptor ligand (i.e. binds the AR). In one embodiment, the SARM compound of formula II is an androgen receptor antagonist (i.e. binds the AR and inactivates it).

Assays to determine whether the compounds of the present invention are AR agonists or antagonists are well known to a person skilled in the art. For example, AR agonistic activity can be determined by monitoring the ability of the SARM compounds to maintain and/or stimulate the growth of AR containing tissue such as prostate and seminal vesicles, as measured by weight. AR antagonistic activity can be determined by monitoring the ability of the SARM compounds inhibit the growth of AR containing tissue.

An androgen receptor is an androgen receptor of any species, for example a mammal. In one embodiment, the androgen receptor is an androgen receptor of a human.

In one embodiment, the SARM compounds bind irreversibly to an androgen receptor. In another embodiment, the SARM compounds bind irreversibly to an androgen receptor of a mammal. In another embodiment, the SARM compounds bind irreversibly to an androgen receptor of a human. Thus, in one embodiment, the compounds of the present invention may contain a functional group (e.g. affinity label) that allows alkylation of the androgen receptor (i.e. covalent bond formation). Thus, in this case, the compounds are alkylating agents which bind irreversibly to the receptor and, accordingly, cannot be displaced by a steroid, such as the endogenous ligands DHT and testosterone. An "alkylating agent" is defined herein as an agent which alkylates (forms a covalent bond) with a cellular component, such as DNA, RNA or enzyme. It is a highly reactive chemical that introduces alkyl radicals into biologically active molecules and thereby prevents their proper functioning. The alkylating moiety is an electrophilic group that interacts with nucleophilic moieties in cellular components. For example, in one embodiment, an alkylating group is an isocyanate moiety, an electrophilic group which forms covalent bonds with nucleophilic groups (N, O, S etc) in cellular components. In another embodiment, an alkylating group is an isothiocyanate moiety, another electrophilic group which forms covalent bonds with nucleophilic groups (N, O, S etc.) in cellular components. In another embodiment, an alkylating group is a haloalkyl ($CH_2X$ wherein X is halogen), an electrophilic group which forms covalent bonds with nucleophilic groups in cellular components. In another embodiment, an alkylating group is a haloalkyl-amido ($NHCOCH_2X$ wherein X is halogen), an electrophilic group which forms covalent bonds with nucleophilic groups in cellular components.

Because the radiolabeled SARM compounds of the present invention bind to the AR and prostate cancer cells contain significantly higher levels of AR than surrounding non-cancerous cells, it is possible to obtain an image of prostate cancer cells to which the radiolabeled SARM compounds have bound. Detection of the radiolabeled SARM compounds, which have bound to the AR, is performed using, for example, single-photon emission computed tomography, positron emission tomography, or other equivalent detection systems to obtain an image of the prostate cancer. The detection occurs through the measurement of radioactive emissions by the compounds of the present invention.

Methods of Using the Compounds of the Present Invention

The high response rate to first line hormonal therapy and the presence of AR in both primary and metastatic prostate tumor cells support the idea that AR is an important mediator of prostate cancer development and growth. Accordingly, by binding the compound of the present invention to the AR of a patient, the accurate imaging of prostate tumors can be achieved.

The compounds of the present invention are useful as a diagnostic tool in imaging and detection of AR-mediated conditions and diseases, for example prostate cancer. Since the radiolabeled SARM compounds of the present invention bind to the AR (for example irreversible binding), and prostate cancer cells contain significantly higher levels of AR than surrounding non-cancerous cells, it is possible to obtain an image of prostate cancer cells to which the radiolabeled SARM compounds have bound. Detection of the radiolabeled SARM compounds, which have bound to the AR, is performed using, for example, single-photon emission computed tomography, positron emission tomography, or other equivalent detection systems to obtain an image of the prostate cancer. The detection occurs through the measurement of radioactive emissions by the compounds of the present invention.

Alternatively, the compounds of the present invention may be used as therapeutic agents to treat a variety of AR-mediated conditions and diseases, for example prostate cancer. Because the radiolabeled SARM compounds of the present invention bind to the AR and prostate cancer cells contain significantly higher levels of AR than surrounding non-cancerous cells, it is possible to selectively affect the cancer cells, while minimizing the effect on non-cancer cells.

The present invention, therefore, is directed to a method of imaging for prostate cancer in a patient. The method of imaging includes contacting an androgen receptor with the radiolabeled selective androgen receptor modulator compound under conditions effective to bind the radiolabeled selective androgen receptor modulator compound to the androgen receptor, and detecting the presence of any radiolabeled SARM compound bound to the androgen receptor. Thus, an image of the prostate tumor cells with the radiolabeled compound bound to the tumor cells is obtained. In one embodiment, the cancer is prostate cancer. In another embodiment, the method comprises contacting the radiolabeled compound to the androgen receptor in vivo. In another embodiment, the method comprises contacting the radiolabeled compound to the androgen receptor in vitro. In another embodiment, the radiolabeled compound binds irreversibly to an androgen receptor. In another embodiment, the radiolabeled compound alkylates the androgen receptor.

Furthermore, in another embodiment, the present invention provides a method of imaging an androgen receptor-containing tissue in a subject comprising contacting an androgen receptor of the subject with a radiolabeled compound of formula I or II, under conditions effective to bind the radiolabeled compound to the androgen receptor, and detecting the presence of the radiolabeled compound bound to the androgen receptor. In one embodiment, the tissue is a prostate tissue. In another embodiment, the method comprises contacting the radiolabeled compound to the androgen receptor in vivo. In another embodiment, the method comprises contacting the radiolabeled compound to the androgen receptor in vitro. In another embodiment, the tissue is a prostate tissue. In another embodiment, the radiolabeled compound binds irreversibly to an androgen receptor. In another embodiment, the radiolabeled compound alkylates the androgen receptor.

Furthermore, in another embodiment, the present invention provides a method of in-vivo imaging in a subject, comprising the steps of administering to the subject a pharmaceutical composition comprising a radiolabeled compound of formula I or II, and detecting the presence of the radiolabeled compound in the patient. In another embodiment, the radiolabeled compound binds irreversibly to an androgen receptor. In another embodiment, the radiolabeled compound alkylates the androgen receptor.

Furthermore, in another embodiment, the present invention provides a method of treating a subject suffering from prostate cancer, the method comprising the steps of administering to the subject a pharmaceutical composition comprising the radiolabeled compound of formula I or II, in an amount effective to treat prostate cancer in the subject. In another embodiment, the method further comprises the step of administering to the subject a chemotherapeutic agent, a radiosensitizer agent, or a combination thereof. In another embodiment, the radiolabeled compound binds irreversibly to an androgen receptor. In another embodiment, the radiolabeled compound alkylates the androgen receptor.

Furthermore, in another embodiment, the present invention provides a method of delaying the progression of prostate cancer in a subject suffering from prostate cancer, comprising the step of administering to the subject a pharmaceutical composition comprising the radiolabeled compound of formula I or II, in an amount effective to delay the progression of prostate cancer in the subject. In another embodiment, the method further comprises the step of adminiistering to the subject a chemotherapeutic agent, a radiosensitizer agent, or a combination thereof. In another embodiment, the radiolabeled compound binds irreversibly to an androgen receptor. In another embodiment, the radiolabeled compound alkylates the androgen receptor.

Furthermore, in another embodiment, the present invention provides a method of preventing the recurrence of prostate cancer in a subject suffering from prostate cancer, comprising the step of administering to the subject a pharmaceutical composition comprising the radiolabeled compound of formula I or II, in an amount effective to prevent the recurrence of prostate cancer in the subject. In another embodiment, the method further comprises the step of administering to the subject a chemotherapeutic agent, a radiosensitizer agent, or a combination thereof. In another embodiment, the radiolabeled compound binds irreversibly to an androgen receptor. In another embodiment, the radiolabeled compound alkylates the androgen receptor.

Furthermore, in another embodiment, the present invention provides a method of treating the recurrence of prostate cancer in a subject suffering from prostate cancer, comprising the step of administering to the subject a pharmaceutical composition comprising the radiolabeled compound of formula I or II, in an amount effective to treat the recurrence of prostate cancer in the subject. In another embodiment, the method further comprises the step of administering to the subject a chemotherapeutic agent, a radiosensitizer agent, or a combination thereof. In another embodiment, the radiolabeled compound binds irreversibly to an androgen receptor. In another embodiment, the radiolabeled compound alkylates the androgen receptor.

As defined herein, "contacting" means that the radiolabeled compound of the present invention is introduced into a sample containing the enzyme in a test tube, flask, tissue culture, chip, array, plate, microplate, capillary, or the like, and incubated at a temperature and time sufficient to permit binding of the SARM to the enzyme. Methods for contacting the samples with the SARM or other specific binding components are known to those skilled in the art and may be selected depending on the type of assay protocol to be run. Incubation methods are also standard and are known to those skilled in the art.

In another embodiment, the term "contacting" means that the radiolabeled compound of the present invention is introduced into a subject receiving treatment, and the SARM compound is allowed to come in contact with the androgen receptor in vivo.

It will be appreciated that the actual amount of the compound to be administered according to the present invention will vary according to the particular compound, the particular composition formulated, and the mode of administration. Many factors that may modify the action of the SARM compound can be taken into account by those skilled in the art; e.g., body weight, diet, time of administration, route of administration, rate of excretion, condition of the subject, drug combinations, and reaction sensitivities and severities. Administration can be carried out continuously or periodically within the maximum tolerated dose. Optimal administration rates for a given set of conditions can be ascertained by those skilled in the art using conventional dosage administration tests.

Pharmaceutical Compositions

Furthermore, in one embodiment, the present invention provides a composition comprising the radiolabeled compound of formula I or II, and a pharmaceutically acceptable carrier. In another embodiment, the present invention provides a pharmaceutical composition comprising the radiolabeled compound of formula I or II, and a pharmaceutically acceptable carrier. In another embodiment, the present invention provides a pharmaceutical composition for use in medical therapy comprising the radiolabeled compound of formula I or II, and a pharmaceutically acceptable carrier. In another embodiment, the present invention provides a pharmaceutical composition for use in medical diagnosis comprising the radiolabeled compound of formula I or II, and a pharmaceutically acceptable carrier.

The compounds herein may be made up in any suitable form appropriate for the desired use; e.g., oral, parenteral (for example, subcutaneously, intravenously, intramuscularly, intraperitoneally, by intranasal instillation, or by application to mucous membranes, such as that of the nose, throat, and bronchial tubes, or by instillation into hollow organ walls or newly vascularized blood vessels) or topical administration. Suitable dosage forms for oral use include tablets, dispersible powders, granules, capsules, suspensions, syrups, and elixirs. The compounds may be administered alone or with suitable pharmaceutical diluents or carriers. Inert diluents and carriers for tablets include, for example, calcium carbonate, sodium carbonate, lactose, and talc. Tablets may also contain granulating and disintegrating agents such as starch and alginic acid, binding agents such as starch, gelatin, and acacia, and lubricating agents such as magnesium stearate, stearic acid, and talc. Tablets may be uncoated or may be coated by known techniques to delay disintegration and absorption. Inert diluents and carriers which may be used in capsules include, for example, calcium carbonate, calcium phosphate, and kaolin. Suspensions, syrups, and elixirs may contain conventional excipients, for example, methyl cellulose, tragacanth, sodium alginate; wetting agents, such as lecithin and polyoxyethylene stearate; and preservatives, e.g., ethyl-p-hydroxybenzoate.

Dosage forms suitable for parenteral administration include solutions, suspensions, dispersions, emulsions, and the like. They may also be manufactured in the form of sterile solid compositions which can be dissolved or suspended in sterile injectable medium immediately before use. They may contain suspending or dispersing agents known in the art.

As used herein, "pharmaceutical composition" means therapeutically and/or diagnostically effective amounts of the radiolabeled compound of the present invention together with suitable diluents, preservatives, solubilizers, emulsifiers, adjuvant and/or carriers. A "therapeutically effective amount" as used herein refers to that amount which provides a therapeutic effect for a given condition and administration regimen. A "diagnostically effective amount" as used herein refers to that amount that enables the diagnosis by for example imaging of a given condition or disease.

Such compositions are liquids or Lyophilized or otherwise dried formulations and include diluents of various buffer content (e.g., Tris-HCl., acetate, phosphate), pH and ionic strength, additives such as albumin or gelatin to prevent absorption to surfaces, detergents (e.g., Tween 20, Tween 80, Pluronic F68, bile acid salts), solubilizing agents (e.g., glycerol, polyethylene glycerol), anti-oxidants (e.g., ascorbic acid, sodium metabisulfite), preservatives (e.g., Thimerosal, benzyl alcohol, parabens), bulling substances or tonicity modifiers (e.g., lactose, mannitol), covalent attachment of polymers such as polyethylene glycol to the protein, complexation with metal ions, or incorporation of the material into or onto particulate preparations of polymeric compounds such as polylactic acid, polglycolic acid, hydrogels, etc, or onto liposomes, microemulsions, micelles, unilamellar or multilamellar vesicles, erythrocyte ghosts, or spheroplasts.) Such compositions will influence the physical state, solubility, stability, rate of in vivo release, and rate of in vivo clearance. Controlled or sustained release compositions include formulation in lipophilic depots (e.g., fatty acids, waxes, oils).

Also comprehended by the invention are particulate compositions coated with polymers (e.g., poloxamers or poloxamines). Other embodiments of the compositions of the invention incorporate particulate forms protective coatings, protease inhibitors or permeation enhancers for various routes of administration, including parenteral, pulmonary, nasal and oral. In one embodiment the pharmaceutical composition is administered parenterally, paracancerally, transmucosally, transdermally, intramuscularly, intravenously, intradermally, subcutaneously, intraperitonealy, intraventricularly, intracranially and intratumorally.

Further, as used herein "pharmaceutically acceptable carriers" are well known to those skilled in the art and include, but are not limited to, 0.01–0.1M and preferably 0.05M phosphate buffer or 0.8% saline. Additionally, such pharmaceutically acceptable carriers may be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media.

Parenteral vehicles include sodium chloride solution, Ringer's dextrose, dextrose and sodium chloride, lactated Ringer's and fixed oils. Intravenous vehicles include fluid and nutrient replenishers, electrolyte replenishers such as those based on Ringer's dextrose, and the like. Preservatives and other additives may also be present, such as, for example, antimicrobials, antioxidants, collating agents, inert gases and the like.

Controlled or sustained release compositions include formulation in lipophilic depots (e.g. fatty acids, waxes, oils). Also comprehended by the invention are particulate compositions coated with polymers (e.g. poloxamers or poloxamines) and the compound coupled to antibodies directed against tissue-specific receptors, ligands or antigens or coupled to ligands of tissue-specific receptors.

Other embodiments of the compositions of the invention incorporate particulate forms, protective coatings, protease inhibitors or permeation enhancers for various routes of administration, including parenteral, pulmonary, nasal and oral.

Compounds modified by the covalent attachment of water-soluble polymers such as polyethylene glycol, copolymers of polyethylene glycol and polypropylene glycol, carboxymethyl cellulose, dextran, polyvinyl alcohol, polyvinylpyrrolidone or polyproline are known to exhibit substantially longer half-lives in blood following intravenous injection than do the corresponding unmodified compounds (Abuchowski et al., 1981; Newmark et al., 1982; and Katre et al., 1987). Such modifications may also increase the compound's solubility in aqueous solution, eliminate aggregation, enhance the physical and chemical stability of the compound, and greatly reduce the immunogenicity and reactivity of the compound. As a result, the desired in vivo biological activity may be achieved by the administration of such polymer-compound abducts less frequently or in lower doses than with the unmodified compound.

In yet another embodiment, the pharmaceutical composition can be delivered in a controlled release system. For example, the agent may be administered using intravenous infusion, an implantable osmotic pump, a transdermal patch, liposomes, or other modes of administration. In one embodiment, a pump may be used (see Langer, supra; Sefton, CRC Crit. Ref. Biomed. Eng. 14:201 (1987); Buchwald et al., *Surgery* 88:507 (1980); Saudek et al., *N. Engl. J. Med.* 321:574 (1989). In another embodiment, polymeric materials can be used. In yet another embodiment, a controlled release system can be placed in proximity to the therapeutic target, i.e., the brain, thus requiring only a fraction of the systemic dose (see, e.g., Goodson, in Medical Applications of Controlled Release, supra, vol. 2, pp. 115–138 (1984). Other controlled release systems are discussed in the review by Langer (*Science* 249:1527–1533 (1990).

The pharmaceutical preparation can comprise the radiolabeled compound alone, or can further include a pharmaceutically acceptable carrier, and can be in solid or liquid form such as tablets, powders, capsules, pellets, solutions, suspensions, elixirs, emulsions, gels, creams, or suppositories, including rectal and urethral suppositories. Pharmaceutically acceptable carriers include gums, starches, sugars, cellulosic materials, and mixtures thereof. The pharmaceutical preparation containing the radiolabeled compound can be administered to a subject by, for example, subcutaneous implantation of a pellet; in a further embodiment, the pellet provides for controlled release of the radiolabeled compound over a period of time. The preparation can also be administered by intravenous, intraarterial, or intramuscular injection of a liquid preparation, oral administration of a liquid or solid preparation, or by topical application. Administration can also be accomplished by use of a rectal suppository or a urethral suppository.

The pharmaceutical preparations of the invention can be prepared by known dissolving, mixing, granulating, or tablet-forming processes. For oral administration, the compounds are mixed with additives customary for this purpose, such as vehicles, stabilizers, or inert diluents, and converted by customary methods into suitable forms for administration, such as tablets, coated tablets, hard or soft gelatin capsules, aqueous, alcoholic or oily solutions. Examples of suitable inert vehicles are conventional tablet bases such as lactose, sucrose, or cornstarch in combination with binders such as acacia, cornstarch, gelatin, with disintegrating agents such as cornstarch, potato starch, alginic acid, or with a lubricant such as stearic acid or magnesium stearate.

Examples of suitable oily vehicles or solvents are vegetable or animal oils such as sunflower oil or fish-liver oil. Preparations can be effected both as dry and as wet granules. For parenteral administration (subcutaneous, intravenous, intraarterial, or intramuscular injection), the radiolabeled compounds are converted into a solution, suspension, or emulsion, if desired with the substances customary and suitable for this purpose, for example, solubilizers or other auxiliaries. Examples are sterile liquids such as water and oils, with or without the addition of a surfactant and other pharmaceutically acceptable adjuvants. Illustrative oils are those of petroleum, animal, vegetable, or synthetic origin, for example, peanut oil, soybean oil, or mineral oil. In general, water, saline, aqueous dextrose and related sugar solutions, and glycols such as propylene glycols or polyethylene glycol are preferred liquid carriers, particularly for injectable solutions.

The preparation of pharmaceutical compositions which contain an active component is well understood in the art. Typically, such compositions are prepared as aerosols of the polypeptide delivered to the nasopharynx or as injectables, either as liquid solutions or suspensions; however, solid forms suitable for solution in, or suspension in, liquid prior to injection can also be prepared. The preparation can also be emulsified. The active therapeutic ingredient is often mixed with excipients which are pharmaceutically acceptable and compatible with the active ingredient. Suitable excipients are, for example, water, saline, dextrose, glycerol, ethanol, or the like or any combination thereof.

In addition, the composition can contain minor amounts of auxiliary substances such as wetting or emulsifying agents, pH buffering agents which enhance the effectiveness of the active ingredient.

An active component can be formulated into the composition as neutralized pharmaceutically acceptable salt forms. Pharmaceutically acceptable salts include the acid addition salts (formed with the free amino groups of the polypeptide or antibody molecule), which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

For topical administration to body surfaces using, for example, creams, gels, drops, and the like, the radiolabeled compounds of the present invention are prepared and applied as solutions, suspensions, or emulsions in a physiologically acceptable diluent with or without a pharmaceutical carrier.

In another embodiment, the active compound can be delivered in a vesicle, in particular a liposome (see Langer, *Science* 249:1527–1533 (1990); Treat et al., in Liposomes in the Therapy of Infectious Disease and Cancer, Lopez-Berestein and Fidler (eds.), Liss, New York, pp. 353–365 (1989); Lopez-Berestein, ibid., pp. 317–327; see generally ibid).

For use in medicine, the salts of the SARM will be pharmaceutically acceptable salts. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, methanesulphonic acid, fumaric acid, maleic acid, succinic acid, acetic acid, benzoic: acid, oxalic acid, citric acid, tartaric acid, carbonic acid or phosphoric acid.

In one embodiment, the therapeutic methods of the present inventions comprise administering the SARM compounds as the sole active ingredient. However, also encompassed within the scope of the present invention are methods for treating prostate cancer, for delaying the progression of prostate cancer, and for preventing and/or treating the recurrence of prostate cancer, which comprise administering the SARM compounds in combination with one or more therapeutic agents. These agents include, but are not limited to: LHRH analogs, reversible antiandrogens, antiestrogens, anticancer drugs, 5-alpha reductase inhibitors, aromatase inhibitors, progestins, agents acting through other nuclear hormone receptors, selective estrogen receptor modulators (SERM), progesterone, estrogen, PDE5 inhibitors, apomorphine, bisphosphonate, and one or more additional SARMS, for example another SARM with AR agonistic activity.

Thus, in one embodiment, the present invention provides compositions and pharmaceutical compositions comprising a selective androgen receptor modulator compound, in combination with an LHRH analog. In another embodiment, the present invention provides compositions and pharmaceutical compositions comprising a selective androgen receptor modulator compound, in combination with a reversible antiandrogen. In another embodiment, the present invention provides compositions and pharmaceutical compositions comprising a selective androgen receptor modulator compound, in combination with an antiestrogen. In another embodiment, the present invention provides compositions and pharmaceutical compositions comprising a selective androgen receptor modulator compound, in combination with an anticancer drug. In another embodiment, the present invention provides compositions and pharmaceutical compositions comprising a selective androgen receptor modulator compound, in combination with a 5-alpha reductase inhibitor. In another embodiment, the present invention provides compositions and pharmaceutical compositions comprising a selective androgen receptor modulator compound, in combination with an aromatase inhibitor. In another embodiment, the present invention provides compositions and pharmaceutical compositions comprising a selective androgen receptor modulator compound, in combination with a progestin. In another embodiment, the present invention provides compositions and pharmaceutical compositions comprising a selective androgen receptor modulator compound, in combination with an agent acting through other nuclear hormone receptors. In another embodiment, the present invention provides compositions and pharmaceutical compositions comprising a selective androgen receptor modulator compound, in combination with a selective estrogen receptor modulators (SERM). In another embodiment, the present invention provides compositions and pharmaceutical compositions comprising a selective androgen receptor modulator compound, in combination with progesterone. In another embodiment, the present invention provides compositions and pharmaceutical compositions comprising a selective androgen receptor modulator compound, in combination with estrogen. In another embodiment, the present invention provides compositions and pharmaceutical compositions comprising a selective androgen receptor modulator compound, in combination with PDE5 inhibitors. In another embodiment, the present invention provides compositions and pharmaceutical compositions comprising a selective androgen receptor modulator compound, in combination with apomorphine. In another embodiment, the present invention provides compositions and pharmaceutical compositions comprising a selective androgen receptor modulator compound, in combination with a bisphosphonate. In another embodiment, the present invention provides compositions and pharmaceutical compositions comprising a selective androgen receptor modulator compound, in combination with one or more additional SARMS.

Synthetic Methods

In another embodiment, the present invention provides methods of producing the radiolabeled SARM compounds of Formula I. Examples of suitable chemical processes for manufacturing SARM compounds are disclosed in U.S. Pat. No. 6,071,957, and in copending U.S. patent application Ser. Nos. 09/935,044 and 09/935,045, filed Aug. 24, 2000, assigned to the assignees of the present invention, which are hereby incorporated by reference herein.

To synthesize the radiolabeled SARM compounds, for example radiohalogenated SARM compounds, a variety of precursors can be used. The precursors are reacted with suitable compounds under conditions effective to produce the radiolabeled SARM compounds of the present invention. Generally, such suitable compounds contain a radioactive component (e.g., $^3H$, $^{18}F$, $^{125}I$, $^{123}I$, or other radiohalogens), which may be bound to the precursor in the step immediately preceding formation of the compounds of the present invention, and may include radioactive halide salts, hydrohalide acids, or elemental halides containing any isotope suitable for imaging.

For example, the precursors used for radiohalogenation can be precursors for aromatic nucleophilic substitution (i.e., aryl diazonium salts, aryl triazenes, tertiary aromatic alkyl amines, nitroaryl precursors, aryl halides); precursors for aromatic electrophilic substitution (i.e., aryl stannanes (Ar—SnR$_3$, aryl boranes Ar—BR$_2$, aryl silanes (ArSiR$_3$), organopetnafluorosilicates (ArSiF$_5$K$_2$), aryl germanes ArGeR$_2$, aryl mercuriates (ArHgCl), aryl thallates Ar-TI(OCOCF$_3$)$_2$, ArH (direct halogenation ortho- or para- to NH$_2$, or OH) precursors for aliphatic nucleophilic substitution (i.e., triflates, mesylates and tosylates, trifluoroacetates, epoxides, cyclic sulfates, alcohols, alkyl halides); or precursors for aliphatic electrophilic substitution (i.e., Alk-BMe$_3$).

In one embodiment, the present invention provides a precursor compound of formula VII, useful in the preparation of the radiolabeled compounds of the present invention.

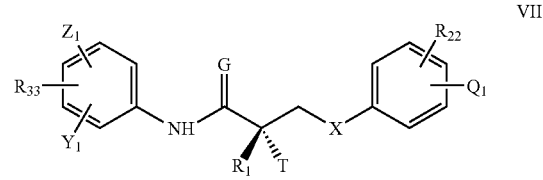

VII wherein X is a bond, O, S, SO$_2$, CH$_2$, NH, NR, Se, PR, or NO;

G is O or S;

T is OH, OR, —NHCOCH$_3$, or NHCOR;

R is alkyl, haloalkyl, dihaloalkyl, trihaloalkyl, CH$_2$F, CHF$_2$, CF$_3$, CF$_2$CF$_3$, aryl, phenyl, halogen, alkenyl or OH;

R$_1$ is CH$_3$, CH$_2$F, CHF$_2$, CF$_3$, CH$_2$CH$_3$, or CF$_2$CF$_3$;

Z$_1$ is a NO$_2$, CN, COR, COOH, or CONHR;

Y$_1$ is CF$_3$, F, Br, Cl, I, CN, or SnR$_3$;

R$_{33}$ is F, Cl, Br, I, OH, CN, NO$_2$, NHCOCH$_3$, NHCOCF$_3$, NHCOR, alkyl, arylaLkyl, OR, NH$_2$, NHR, NR$_2$, SR; or Z$_1$, Y$_1$ and R$_{33}$ are independently of each other an isothiocyanate, an azide, a diazocarbonyl, a substituted oxirane, a β-chloroethylamine, a diazonium salt, a triazene group, a tertiary alkyl group, an oxy group, an alkoxy group, a stannoalkyl group, a stannoaryl group, an unsubstituted or substituted boronic acid, an alkyl silane group, a pentaflourosilicate group, an alkylgermano group, a halomercury group, a trifluoroacetylthallate group, or a thallium difluoride group;

Q$_1$ is CF$_3$, CN, CR$_3$, SnR$_3$, NR$_2$, NHCOCH$_3$, NHCOCF$_3$, NHCOR, NHCONHR, NHCOOR, OCONHR, CONHR, NHCSCH$_3$, NHCSCF$_3$, NHCSR, NHSO$_2$CH$_3$, NHSO$_2$R, OR, COR, OCOR, OSO$_2$R, SO$_2$R, SR, SCN, NCS, OCN, NCO; or Q together with the benzene ring to which it is attached is a fused ring system represented by structure A, B or C:

A

B

C $R_{22}$ is nonradioactive F, Cl, Br, I, OH, CN, $NO_2$, $NHCOCH_3$, $NHCOCF_3$, NHCOR, alkyl, arylalkyl, OR, $NH_2$, NHR, $NR_2$, SR; or $Q_1$ and $R_{22}$ are independently of each other a diazonium salt, a triazene group, a tertiary alkyl amino group, a nitro group, an oxy or an aLkoxy group, an amino or an alkylamino group, a stannoalkyl group ($SnAlk_3$), a stannoaryl group ($SnAR_3$), an unsubstituted or a substituted boronic acid, an alkyl silane group ($SiR_3$), a pentafluorosilicate ($SiF_5$) group, an alkylgermano group ($GeAlk_2$), a halomercury group (HgHal), a trifluoroacetyl thallate group, or a thallium difluoride group;

In one embodiment, $Y_1$ in compound VII is a stannoalkyl. In another embodiment, $Y_1$ in compound VII is $Sn(CH_3)_3$. In another embodiment, Y in compound VII is a radioactive halogen. In another embodiment, Y in compound VII is $^{125}I$.

Thus, in one embodiment, the present invention provides The present invention further provides a method of producing a radiolabeled selective androgen receptor modulator (SARM) compound of formula I, comprising:

providing a precursor compound represented by the structure of formula VII:

VII wherein X is a bond, O, S, $SO_2$, $CH_2$, NH, NR, Se, PR, or NO;

G is O or S;

T is OH, OR, —$NHCOCH_3$, or NHCOR;

R is alkyl, haloalkyl, dihaloalkyl, trihaloalkyl, $CH_2F$, $CHF_2$, $CF_3$, $CF_2CF_3$, aryl, phenyl, halogen, alkenyl or OH;

$R_1$ is $CH_3$, $CH_2F$, $CHF_2$, $CF_3$, $CH_2CH_3$, or $CF_2CF_3$;

$Z_1$ is a $NO_2$, CN, COR, COOH, or CONHR;

$Y_1$ is $CF_3$, F, Br, Cl, I, CN, or $SnR_3$;

$R_{33}$ is F, Cl, Br, I, OH, CN, $NO_2$, $NHCOCH_3$, $NHCOCF_3$, NHCOR, alkyl, arylalkyl, OR, $NH_2$, NHR, $NR_2$, SR; or $Z_1$, $Y_1$ and $R_{33}$ are independently of each other an isothiocyanate, an azide, a diazocarbonyl, a substituted oxirane, a β-chloroethylamine, a diazonium salt, a triazene group, a tertiary alkyl group, an oxy group, an alkoxy group, a stannoalkyl group, a stannoaryl group, an unsubstituted or substituted boronic acid, an alkyl silane group, a pentaflourosilicate group, an alkylgermano group, a halomercury group, a trifluoroacetylthallate group, or a thallium difluoride group;

Q is a radioactive or a nonradpoactive alkyl, halogen, $CF_3$, CN, $CR_3$, $SnR_3$, $NR_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OR, COR, OCOR, $OSO_2R$, $SO_2R$, SR, SCN, NCS, OCN, NCO; or Q together with the benzene ring to which it is attached is a fused ring system represented by structure A, B or C:

A

B

C $R_{22}$ is nonradioactive F, Cl, Br, I, OH, CN, $NO_2$, $NHCOCH_3$, $NHCOCF_3$, NHCOR, alkyl, arylaLkyl, OR, $NH_2$, NHR, $NR_2$, SR; or $Q_1$ and $R_{22}$ are independently of each other a diazonium salt, a triazene group, a tertiary alkyl amino group, a nitro group, an oxy or an alkoxy group, an amino or an alkylamino group, a stannoalkyl group ($SnAlk_3$), a stannoaryl group ($SnAr_3$), an unsubstituted or a substituted boronic acid, an alkyl silane group ($SiR_3$), a pentafluorosilicate ($SiF_5$) group, an alkylgermano group ($GeAlk_2$), a halomercury group (HgHal), a trifluoroacetyl thallate group, or a thallium difluoride group;

providing a radioactive compound; and reacting the precursor compound and the radioactive compound under conditions effective to produce a radiolabeled selective androgen receptor modulator (SARM) compound represented by the structure of formula I.

Examples of some reactions for preparing the SARM compounds of the present invention are as follows:

A. Aryl Diazonium Salts in Preparation of Aromatic Radiohalogenated AR Ligands

As shown in Scheme 1 below, aromatic diazonium salts are useful precursors for radiohalogenation (Knoechel et al., "Development of a Non-Carrier Method For 18F-Labeling," J. Labeled Comp. Radiopharm., 38:325–36 (1996); Muller et al., "Synthesis of [$^{18}F$]NNC," Appl. Radiat. Isot., 46:323–28 (1995)). This so-called Sandmeyer reaction requires use of copper salts as a catalyst. The use of diazonium salts is described in Berridge et al., "Aromatic Fluorination With N.C.A. 18F-Fluoride: A Comparative Study," J. Labeled Compd. Radiopharm., 22:687–94 (1985).

Scheme 1

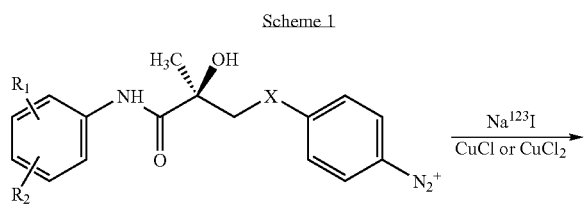

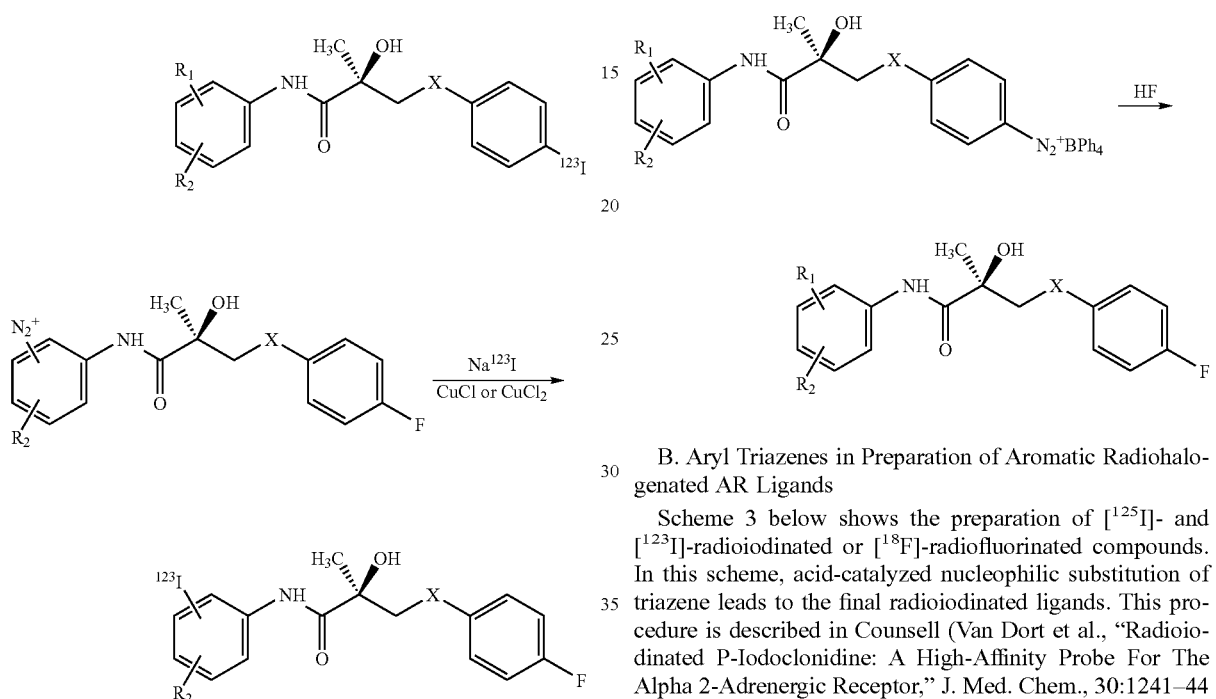

$R_1$ and $R_2$, used inter alia the examples provided below, are one or more of the susbstituents Y, Z or $R_1$ defined above.

According to Ng et al., "Aromatic Fluorinations Suitable For Fluorine-18 Labeling of Estrogens," J. Org. Chem., 46:2520–28 (1981), decomposition of tetraphenylborate diazonium salts gives fluorinated product. This reaction can be used for radiofluorination as illustrated in Scheme 2 below, where HF is a radiolabeled acid.

B. Aryl Triazenes in Preparation of Aromatic Radiohalogenated AR Ligands

Scheme 3 below shows the preparation of $[^{125}I]$- and $[^{123}I]$-radioiodinated or $[^{18}F]$-radiofluorinated compounds. In this scheme, acid-catalyzed nucleophilic substitution of triazene leads to the final radioiodinated ligands. This procedure is described in Counsell (Van Dort et al., "Radioiodinated P-Iodoclonidine: A High-Affinity Probe For The Alpha 2-Adrenergic Receptor," J. Med. Chem., 30:1241–44 (1987)), where $R_8$ is a phenyl substituent as set forth above, preferably a radiohalide.

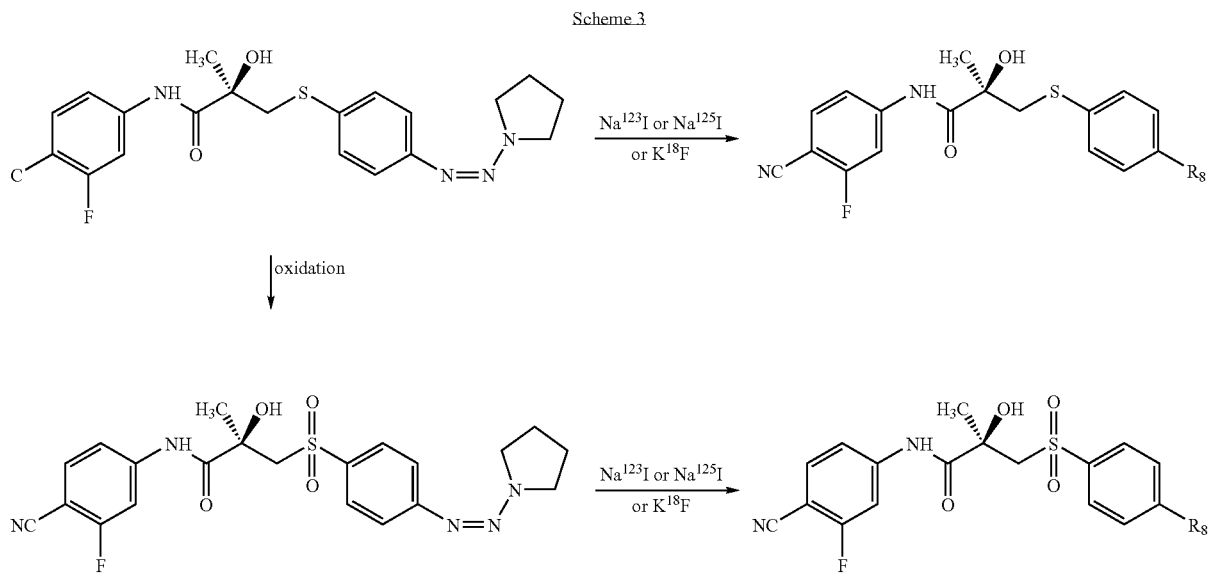

Piperidiene triazenes also can be used for radiohalogenation. Unfortunately, described yield of radiofluorination was very low (<4%) in the case of the reaction in DMSO at 180.degree. C. in the course of preparation of the analog of MPTP (Berridge et al., "Design and Synthesis of $^{18}$F-Labeled Neurotoxic Analogs of MPTP," J. Med. Chem., 36:1284–90 (1993)) and in model reactions (Berridge et al., "Aromatic Fluorination with n.c.a. $^{18}$F-fluoride: A Comparative Study," J. Labeled Campd. Radiopharm., 22:687–94 (1985); Kilbourn et al., "Carrier-added and No-carrier-added Syntheses of [$^{18}$F]spiroperidol and [$^{18}$F]haloperidol," Int. J. Appl. Radiat. Isot., 35:591–98 (1984)). Moderate yields (0–43%) of fluorinated products have been obtained by decomposition of piperidino triazenes in HF (Ng et al., "Aromatic Fluorinations Suitable for Fluorine-18 Labeling of Estrogens," J. Org. Chem., 46:2520–28 (1981)). The use of triazene derivatives for [$^{18}$F]radiofluorination, [$^{78}$Br], [$^{77}$Br] radiobromination, and [$^{125}$I] radioiodination is described in U.S. Pat. No. 4,431,627 to Eckelman et al. Fluorination using triazene as a precursor is described in Tewson et al., "Preparation of Fluorine-18 Aryl Fluorides: Piperidyl Triazenes as a Source of Diazonium Salts," J. Chem. Soc., Chem. Commun., 1149–50 (1979) and Berridge et al., "Aromatic Fluorination with n.c.a. $^{18}$F-fluoride: A Comparative Study," J. Labeled Campd. Radiopharm., 22:687–94 (1985).

C. Tertiary Aromatic Alkyl Amines in Preparation of Aromatic Radiohalogenated AR Ligands Aromatic tertiary alkyl amines can be displaced with halogen. This method was used in the preparation of radiofluorinated GABA$_A$-gated chlorine ion exchange blocker (DMSO, 135.degree. C., Kryptofix, NA. $^{125}$I,) (Snyder et al., "Synthesis of Carbon-11, Fluorine-18, and Iodine-125-," J. Med. Chem., 38:2663–71 (1995)), and can be used for radiofluorination of AR ligands according to Scheme 4 below.

Scheme 4

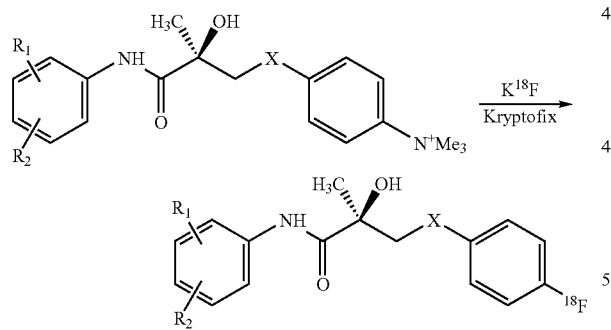

D. Nitroaryl Precursors Ar—NO$_2$ in Preparation of Aromatic Radiohalogenated AR Ligands Aromatic nitro compounds are used for substitution for fluorine. This method was described in Kilbourn et al., "Fluorine-18 Labeling of Proteins," J. Nucl Med., 28:462–70 (1987); Hwang et al., "A New Procedure for Labeling Alkylbenzenes with [$^{18}$F]fluoride," Int. J. Rad. Appl. Instrum.[A], 42:1043–47 (1991). Yields from good (53–85%) to poor (2–9%) have been obtained with use of B.$_4$ NH$^{18}$F ($^{18}$F) as a carrier of fluorine-18 (Kilbourn et al., "Carrier-added and No-carrier-added Syntheses of [$^{18}$F] spiroperidol and [$^{18}$F]haloperidol," Int. J. Appl. Radiat. Isot., 35:591–98 (1984)). Nucleophilic displacement of aromatic nitro group has been widely studied in Attina et al., "Labeled Aryl Fluorides from the Nucleophilic Displacement of Activated Nitro Group by $^{18}$F", J. Label. Comp. Radiopharm. 20:501–14 (1983). For radiofluorination, Scheme 5 below is appropriate.

Scheme 5

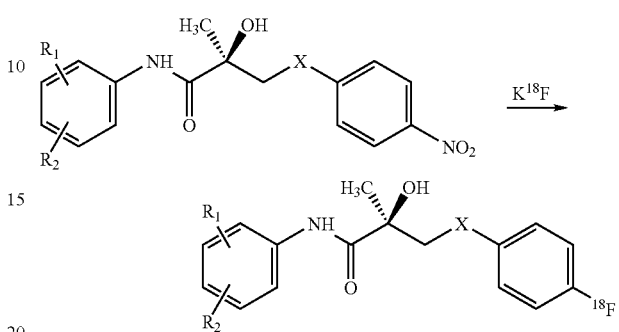

E. Aryl Halides in Preparation of Aromatic Radiohalogenated AR Ligands Halogen Exchange Reactions Aromatic halogens can be exchanged with the same but radioactive halogen atom (homoexchange), or another radioactive halogen (heteroexchange) atom at elevated temperatures.

The exchange of iodine atom on $^{125}$I has been described for 3,5-diiodothirosine in an aqueous solution at 99.degree. C. in Breslav et al., In American Peptide Symposium, 14th; Columbus, Ohio, (1995), and in the presence of ammonia sulphate (NH)$_4$ SO$_4$ and Na$^{125}$I at 145.degree. C. (Snyder et al., "Synthesis of Carbon-11, Fluorine-18, and Iodine-125," J. Med. Chem., 38:2663–71 (1995)). For radiohalogenation, Scheme 6 below is appropriate.

Scheme 6

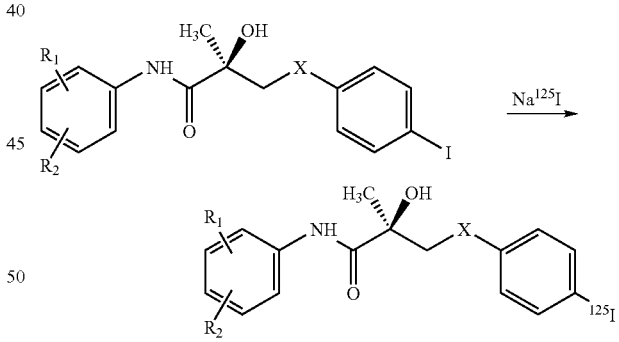

Exchange of iodine in preparation of radioiodinated lipids is described in Meyer et al., "Potential Tumor or Organ-Imaging Agents. Radioiodinated Phospholipid Ethers," J. Med. Chem., 32:2142–7 (1989); Counsell et al., "Tumor Visualization with a Radioiodinated Phospholipid Ether," J. Nucl. Med. 31:332–36 (1990); Seevers et al., "Potential Tumor," J. Med. Chem., 25:1500–03 (1982). The same reaction is described in DeGalan et al., "Iodine-125 Cholesteryl Iopanoate for Measuring Extent of Artherosclerosis in Rabbits," J. Nucl. Med., 29:503–8 (1988); Counsell et al., "Lipoprotein Incorporation Enhances Radioiodinated Cholesteryl Ester Uptake into Steroid Hormone-Secreting Tissues," J. Nucl. Med., 30:1088–94 (1989); Plotzke et al., "Selective Localization of Radioiodinated Alkylphosphocholine Derivatives in Tumors," Int. J. Rad. Appl. Instrum. [B], 19:765–73 (1992).

The exchange of an iodine atom for $^{18}$F has been described in Berridge et al., "Aromatic Fluorination with n.c.a. 18F-fluoride: A Comparative Study," J. Labeled Compd. Radiopharm., 22:687–94 (1985). Scheme 7 below is appropriate for radiofluorination.

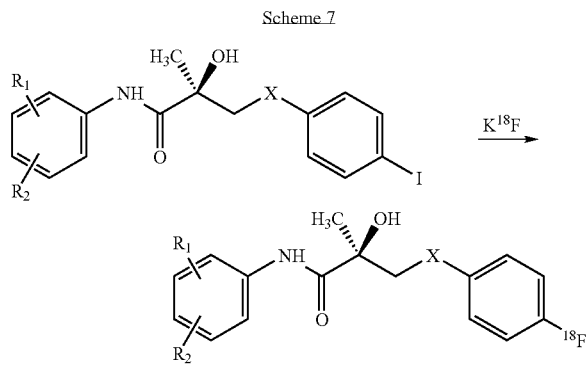

A single-step procedure for bromine-iodine exchange has been proposed in Ceuster et al., "New Single-Step Radioiodination," J. Org. Chem., 60:8324–26 (1995). A similar approach can lead to radioiodinated AR ligands of the present invention, as shown in Scheme 8 below.

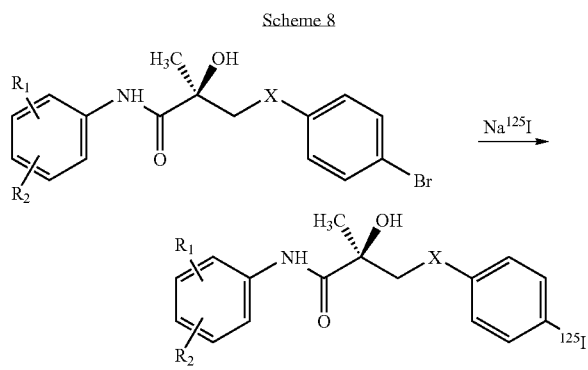

The exchange of aromatic bromide for $^{18}$F has been described in Berridge et al., "Aromatic Fluorination with n.c.a. $^{18}$F-fluoride: A Comparative Study," J. Labeled Compd. Radiopharm., 22:687–94 (1985). Scheme 9 below is appropriate for radiofluorination.

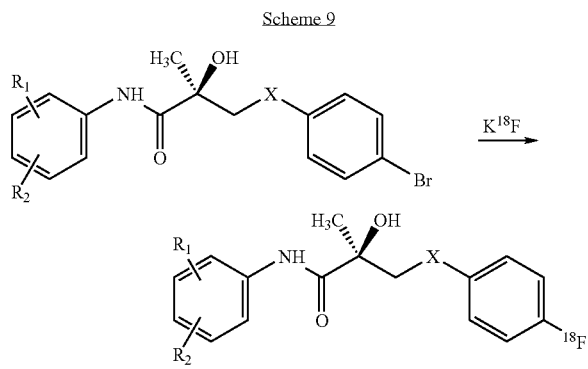

A chlorine-fluorine exchange as described in Kilbourn et al., "Carrier-added and No-carrier-added Syntheses of [$^{18}$F] spiroperidol and [$^{18}$F]haloperidol," Int. J. Appl. Radiat. Isot., 35:591–98 (1984) as shown below in Scheme 10 may be used for radiofluorination.

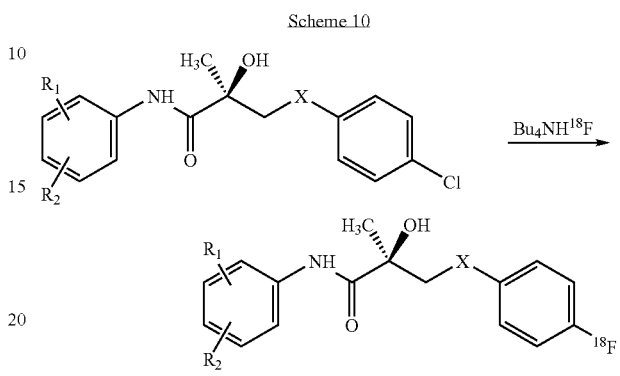

Fluorine-fluorine exchange as described by Kilbourn et al., "Carrier-added and No-carrier-added Syntheses of [$^{18}$F] spiroperidol and [$^{18}$F]haloperidol," Int. J. Appl. Radiat. Isot., 35:591–98 (1984) as shown below in Scheme 11 may be used to prepare radiofluorinated product. This reaction was also described in Attina et al., "Labeled Aryl Fluorides from the Nucleophilic Displacement of Activated Nitro Group by 18F—F—," J. Label. Comp. Radiopharm., 20:501–14 (1983).

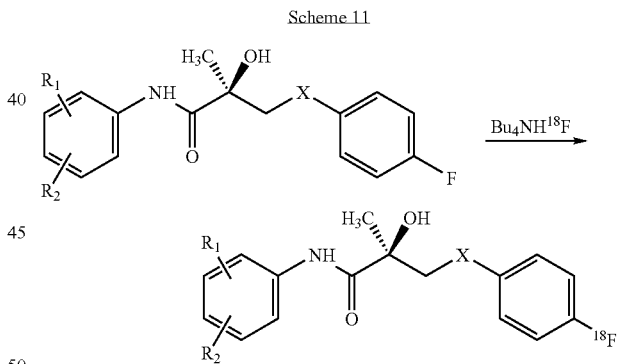

F. Aryl Stannanes in Preparation of Aromatic Radiohalogenated AR Ligands

Scheme 12 below shows the use of tributyltin precursor for the synthesis of radioiodinated AR ligands. (John et al., "Synthesis and Pharmacological," Cancer Res., 55:3022–27 (1995); ((Mais et al., "Novel Synthesis and Biochemical Properties," J. Med. Chem., 34:1511–14 (1991)) Gallant et al., In ACS Meeting. 209th; ACS: Anaheim, Calif. Apr. 2–6, 1995 pp. MEDI-171 (1995)); Hodson et al., "Regiospecific Synthesis," Perkin Trans. 1, 2965–68 (1995); Wardell et al., "Reactions of Aromatic Sulfenyl Compounds with Organotin Compounds," J. Organomet. Chem., 78:395–404 (1974)).

Scheme 12

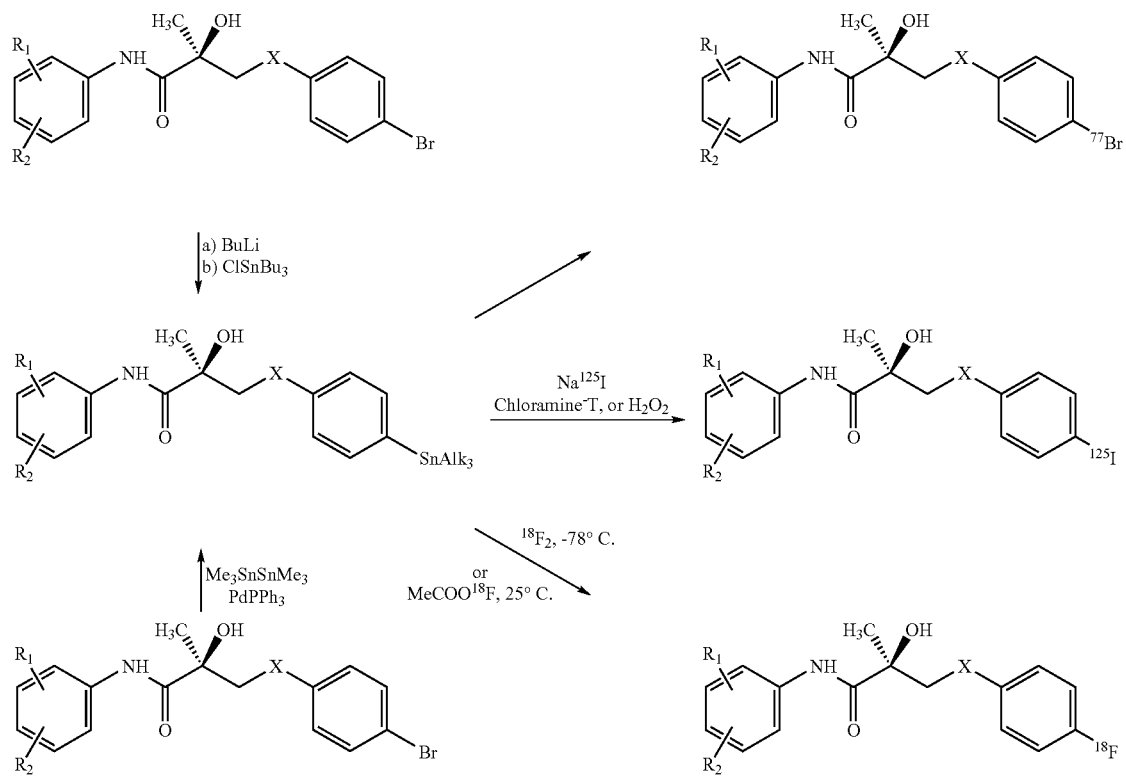

The advantages of these precursors in the incorporation of radiohalogens are their easy preparation and chemical stability. However, they are highly toxic (Kabalka, "The Synthesis of Radiolabeled Compounds Via Organometallic Intermediates," Tetrahedron, 45:6601–21 (1989)).

As shown below in Scheme 13, triphenyltin derivatives can be reacted with elemental fluorine for radiofluorination according to a procedure described in Berridge "Chemistry of Fluorine-18 Radiopharmaceuticals," Appl. Radiat. Isot., 37:685–93 (1986).

Scheme 13

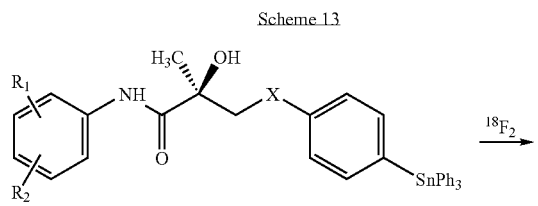

-continued

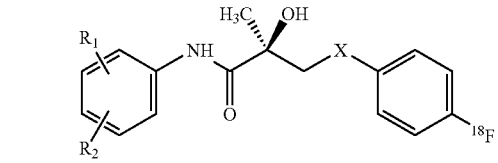

G. Aryl Boranes in Preparation of Aromatic Radiohalogenated AR Ligands

The iodination of an aromatic ring can be achieved via the direct reaction of arylboronic acid with radiolabeled sodium iodide in the presence of an oxidizing agent (Kabalka, "The Synthesis of Radiolabeled Compounds Via Organometallic Intermediates," Tetrahedron, 45:6601–21 (1989). Similar precursors can be used for [$^{18}$F]-radiobromination, [$^{77}$Br]-radiochlorination, and [$^{34m}$Cl]-radiochlorination, as shown below in Scheme 14.

Scheme 14

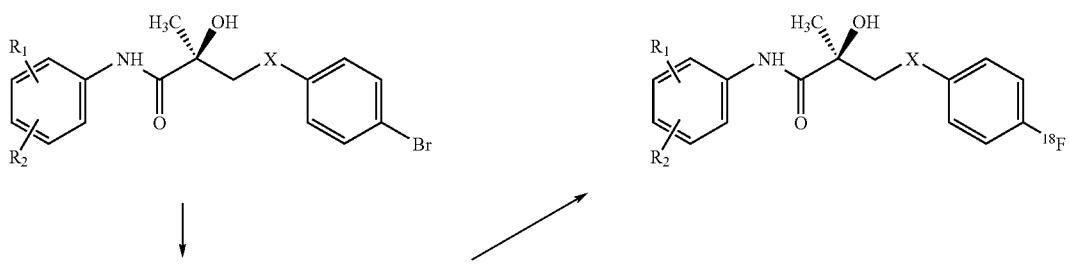

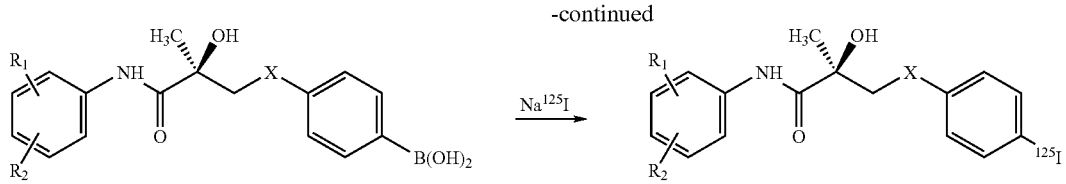

H. Aryl Silanes (Ar—SiR$_3$) and Organopentafluorosilicates (Ar—SiF$_5$K$_2$) in Preparation of Aromatic Radiohalogenated AR Ligands Arylsilanes shown below in Scheme 15 are valuable precursors for radiohalogenation under a variety of conditions and forms of halogen used (Kabalka, "The Synthesis of Radiolabeled Compounds Via Organometallic Intermediates," Tetrahedron, 45:6601–21 (1989)).

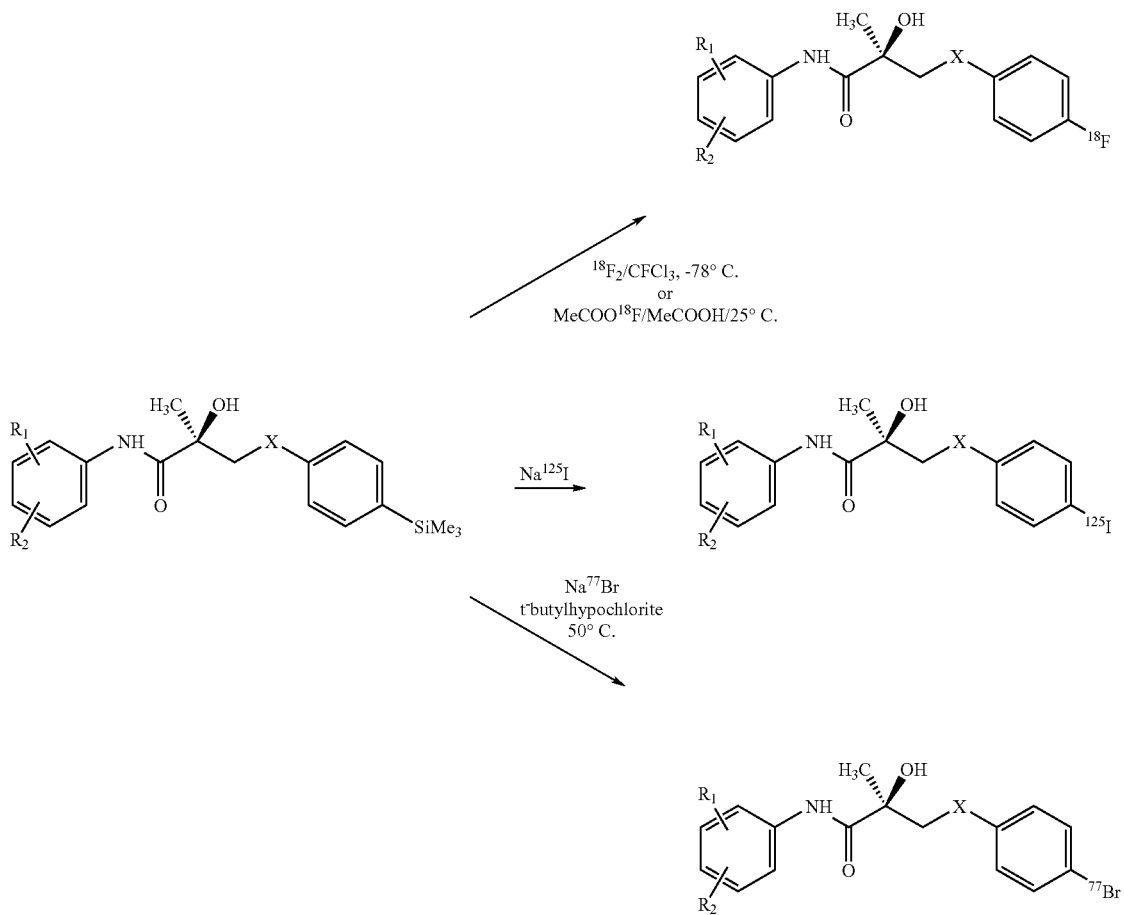

Organopentafluorosilicates are air and moisture stable precursors of radiohalogenated compounds (Kabalka, "The Synthesis of Radiolabeled Compounds Via Organometallic Intermediates," Tetrahedron, 45:6601–21 (1989)). They can be used for preparation of the AR radioligands, according to Scheme 16 below.

Scheme 16

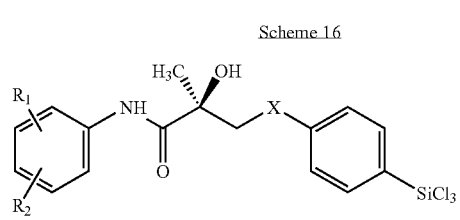

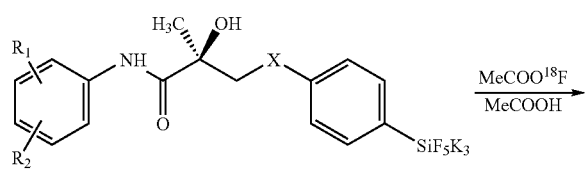

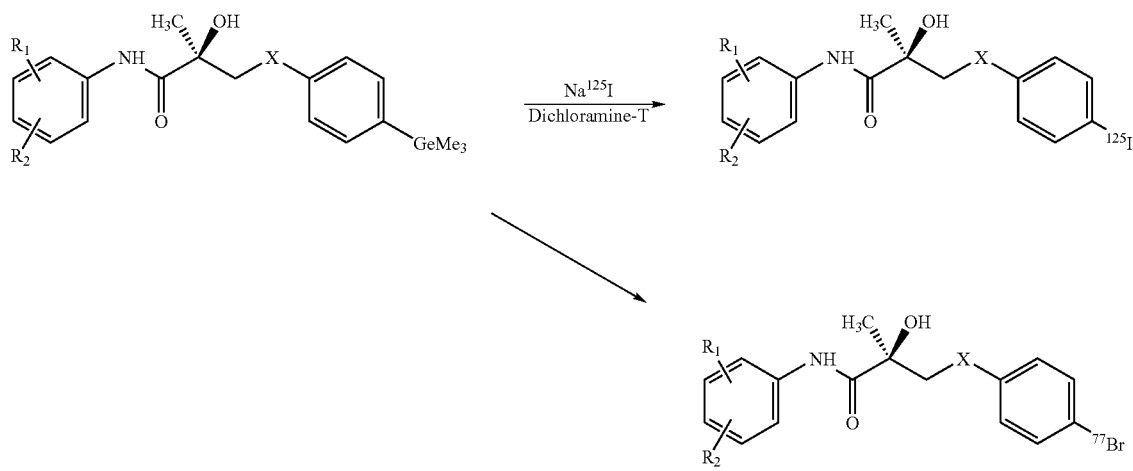

I. Aryl Germanes (Ar—GeR$_2$) in Preparation of Aromatic Radiohalogenated AR Liands Aryl germanes are chemically stable and low-toxic intermediates of aromatic radioiodination and radiobromination (Kabalka, "The Synthesis of Radiolabeled Compounds Via Organometallic Intermediates," Tetrahedron, 45:6601–21 (1989)). Their use for synthesis of radiohalogenated AR ligands is shown below in Scheme 17.

Scheme 17

J. Aryl Mercuriates in Preparation of Aromatic Radiohalogenated AR Ligands

A tributyltin precursor is used as shown below in Scheme 18 for the synthesis of radioiodinated AR ligands. The advantages of these precursors in the incorporation of radiohalogens are their easy preparation and chemical stability. However, they are highly toxic (Kabalka, "The Synthesis of Radiolabeled Compounds Via Organometallic Intermediates," Tetrahedron, 45:6601–21 (1989)).

Scheme 18

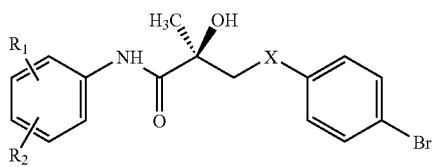

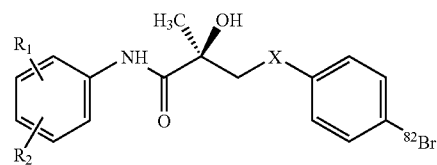

-continued

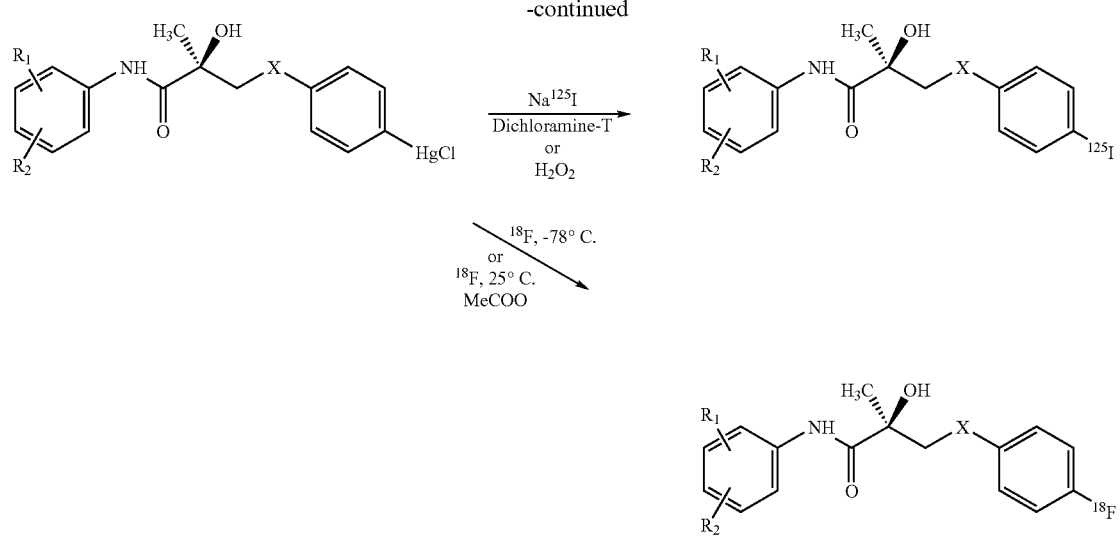

K. Aryl Thallates Ar—Tl(OCOCF₃)₂ in Preparation of Aromatic Radiohalogenated AR Ligands Aryl thallates can be prepared by predominantly para-substitution in an aromatic ring (Kabalka, "The Synthesis of Radiolabeled Compounds Via Organometallic Intermediates," Tetrahedron, 45:6601–21 (1989)). In the case of an aromatic ring containing strong electron withdrawing substituents, thallation can be achieved in the meta-position. As shown below in Scheme 19, the aryl thallates may be used to produce radiolabeled AR ligands.

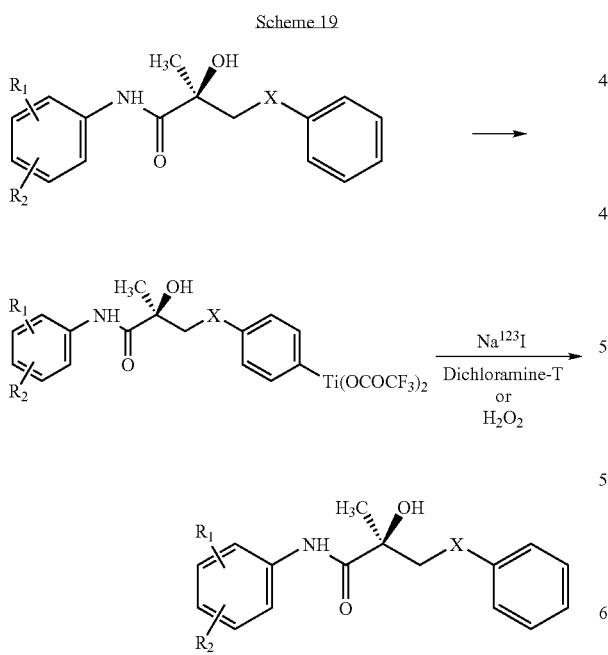

Arylthallium difluorides, shown below in Scheme 20 in the presence of boron trifluorides, can be decomposed to radiofluorides according to Taylor et al., J. Org. Chem., 42:362 (1977).

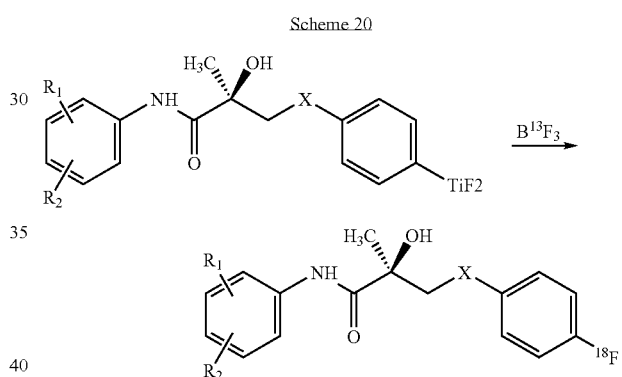

L. Direct Halogenation

Direct fluorination has been done in the case of 4-boronophenylalanine with $^{18}F_2$, or MeCOO$^8$F as a source of fluorine (Ishiwata et al., "Synthesis and Radiation Dosimetry of 4-Borono-2-[18]fluoro-D,L-phenylalanine: A Target Compound for PET and Boron Neutron Capture Therapy," Int. J. Rad. Appl. Instrum. [A], 42:325–28 (1991); Reddy et al., "4-Borono-2-," J. Labeled Comp. Radiopharm., 37:599 (1995)). Similarly, fluorination of an amino precursor can be carried out according to Scheme 21 below. Direct iodination with TlCl₃ is described in Resek, "Photoaffinity Labeling," J. Biol. Chem., 263:14410–16 (1988).

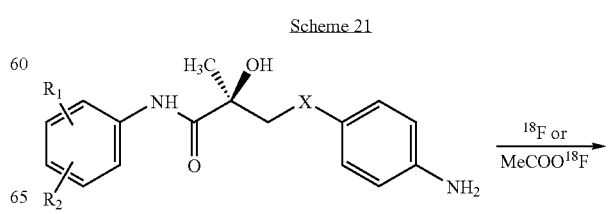

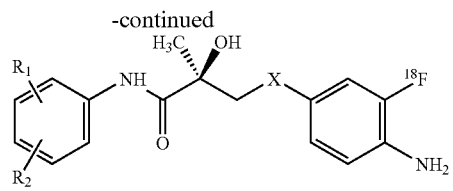

M. Triflates, Mesylates and Tosylates

Triflates and tosylates are used for nucleophilic displacement leading to a radiohalogenated product. Katzenellenbogen used triflates as precursors for [$^{18}$F]-fluorinated steroidal androgen receptor ligands in the synthesis of steroidal AR ligands (Liu et al., "Synthesis of High-Affinity Fluorine-Substituted Ligands for the Androgen Receptor: Potential Agents for Imaging Prostatic Cancer by Positron Emission Tomography," J. Med. Chem., 35:2113–29 (1992); Liu et al., "Fluorine-18-labeled Androgens: Radiochemical Synthesis and Tissue Distribution Studies on Six Fluorine-Substituted Androgens, Potential Imaging Agents for Prostatic Cancer," J. Nucl. Med., 33:724–34 (1992); Pomper et al., "11.beta.-Methoxy-, 11.beta.-Ethyl, and 17.alpha.-Ethynyl-substituted 16.alpha-Fluoroestradiols: Receptor-Based Imaging Agents with Enhanced Uptake Efficiency and Selectivity," J. Med. Chem., 33:3145–55 (1990)). Tetrabutylammonium [$^{18}$F] fluoride was the carrier for the radiohalogen. Thus, displacement of triflates with K$^{18}$F described in Zhang et al., "Synthesis and Evaluation of Two," J. Med. Chem., 39:5110–18 (1996) was performed according to [Kiesewetter, 1989 #4735]. Similarly, a precursor can also be easily prepared from iodide using commercially available silver triflate (e.g., silver trifluoromethanesulfonate, Aldrich Chemical Co., Milwaukee, Wis.). (See, also the procedure for mild etherification of alcohols with primary alkyl halides (Tetrahedr. Lett., 35:8111 (1994); Tetrahedr. Lett., 36:719 (1995))-Scheme 22 below.

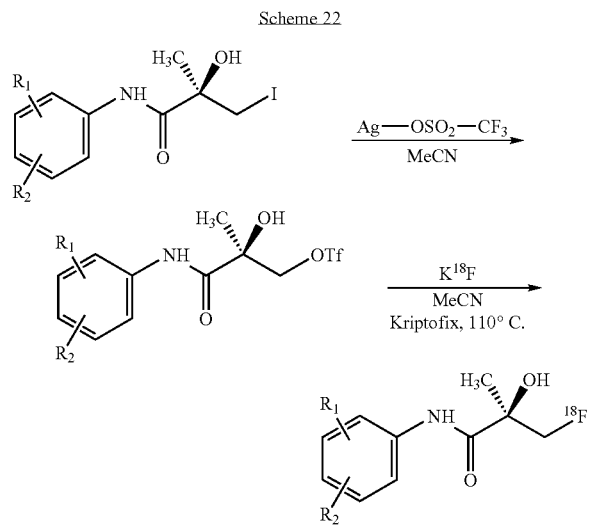

The use of mesylates as a precursor for fluorination is described in Kiesewetter et al., "Synthesis and Biological Properties of," J. Med. Chem., 38:1711–19 (1995). The authors used Me$_4$NHF$_2$ as a source of [$^{19}$F]-fluorine. Methylates can be easily prepared from iodide (shown below in Scheme 23) using commercially available silver mesylate (e.g., methanesulfonic acid silver salt, Acros, Coral Gables, Fla.).

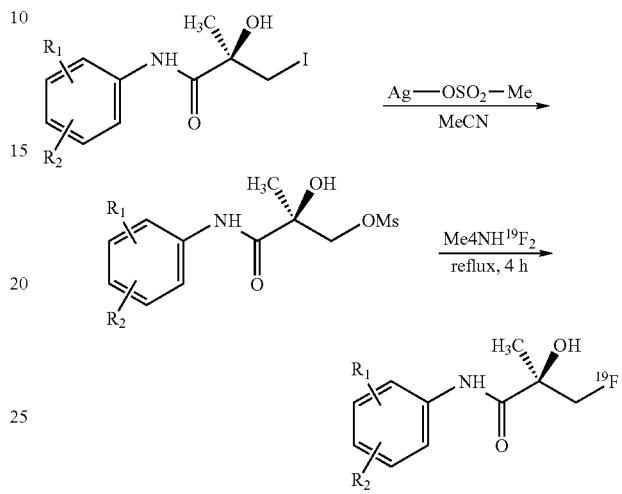

N. Trifluoroacetates

Aliphatic trifluoroacetates are used for fluorination of estradiols with Bu.sub.4 NF as a source of fluorine (Pomper et al., "11.beta.-Methoxy-, 11.beta.-Ethyl, and 17.alpha.-Ethynyl-substituted 16.alpha-Fluoroestradiols: Receptor-Based Imaging Agents with Enhanced Uptake Efficiency and Selectivity," J. Med. Chem., 33:3145–55 (1990)). As similar method can be applied to AR ligands (Scheme 24).

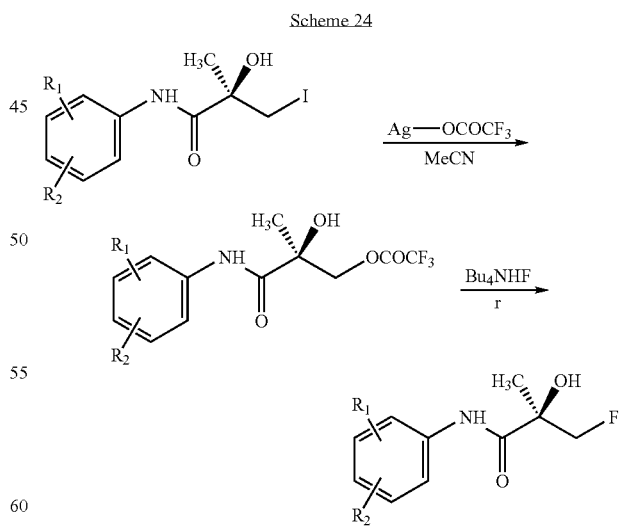

O. Epoxides

Opening of epoxides can be used for radiohalogenation as shown in Scheme 25 below, where R$_8$ is a phenyl substituent as set forth above, preferably a radiohalide.

Scheme 25

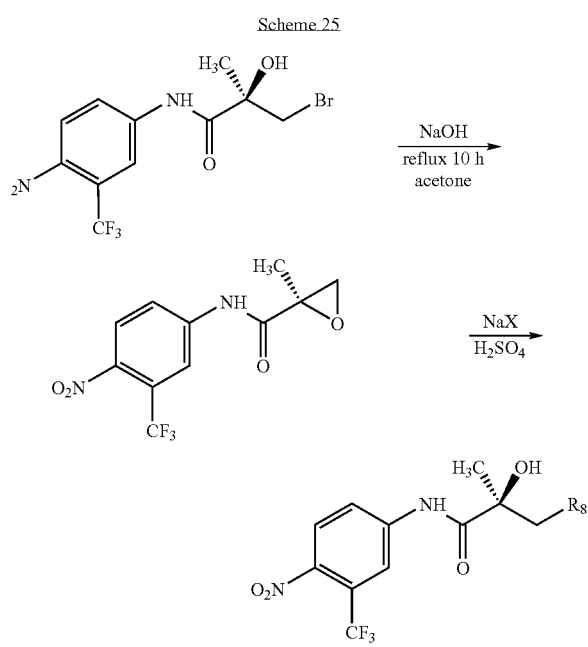

P. Cyclic Sulfates

Katzenellenbogen used cyclic sulfates as precursors for radiofluorination of steroidal androgen receptor ligands metribolone (R1881) (Liu et al., "Fluorine-18-Labeled Androgens: Radiochemical Synthesis and Tissue Distribution Studies on Six Fluorine-Substituted Androgens, Potential Imaging Agents for Prostatic Cancer," J. Nucl. Med., 33:724–34 (1992)), in the synthesis of steroidal AR ligands (Liu et al., "Synthesis of High-Affinity Fluorine-Substituted Ligands for the Androgen Receptor. Potential Agents for Imaging Prostatic Cancer by Positron Emission Tomography," J. Med. Chem., 35:2113–29 (1992)). Tetrabutylammonium [$^{18}$F]fluroide was the carrier for the radiohalogen. Synthesis of cyclic sulfates is described in Liu et al., "Synthesis of High-Affinity Fluorine-Substituted Ligands for the Androgen Receptor. Potential Agents for Imaging Prostatic Cancer by Positron Emission Tomography," J. Med. Chem., 35:2113–29 (1992). Cyclic sulfates are useful precursors for radiohalogenation to AR ligands (Scheme 26).

Scheme 26

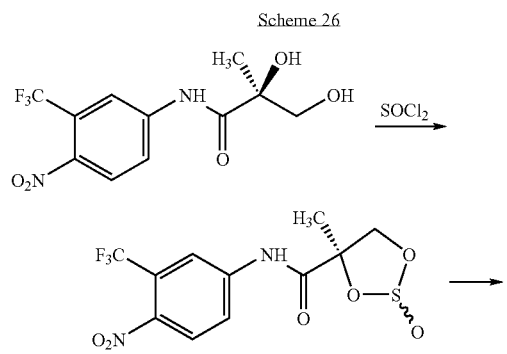

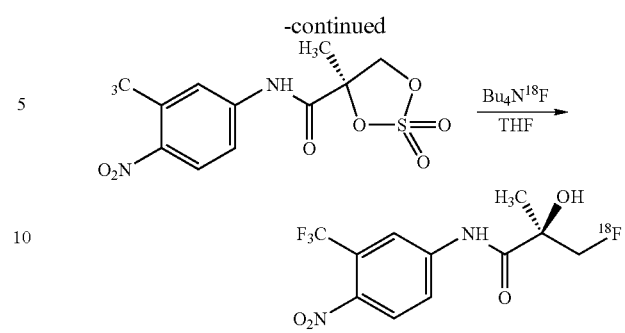

Q. Exchange of Alcohols for Halogens

An iodinated compound can be prepared following the procedure of Hoyte et al., ("Synthesis and Evaluation of 7 alpha-iodo-5 alpha-dihydrotestosterone as a Potential Radioligand for Androgen Receptor," J. Med. Chem., 37(8): 1224–30 (1994) as shown below in Scheme 27, where $R_8$ is a phenyl substituent as set forth above, preferably a radiohalide.

Scheme 27

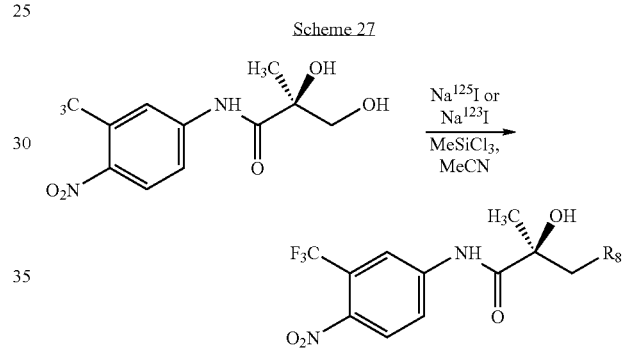

Radiolabeled compounds can be prepared using Scheme 28 shown below where $R_8$ is a phenyl substituent as set forth above, preferably a radiohalide. This method was described in Berridge et al., "Design and Synthesis of $^{18}$F-labeled Neurotoxic Analogs of MPTP," J. Med. Chem., 36:1284–90 (1993); Berridge, "Chemistry of Fluorine-18 Radiopharmaceuticals," Appl. Radiat. Isot., 37:685–93 (1986)); Liu et al., "Synthesis of High-Affinity Fluorine-Substituted Ligands for the Androgen Receptor. Potential Agents for Imaging Prostatic Cancer by positron emission tomography," J. Med. Chem., 35:2113–29 (1992).

Scheme 28

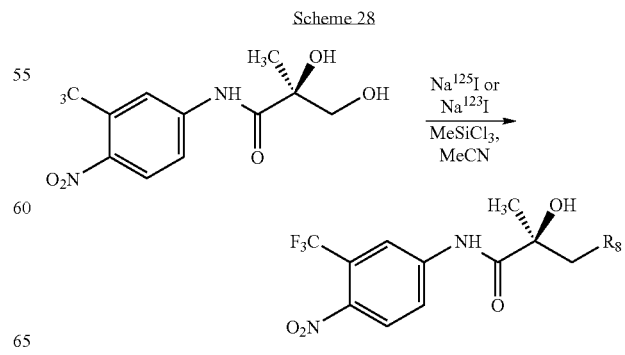

R. Exchange of Halogens

The radiolabeled compounds of the present invention can be produced using Scheme 29 shown below.

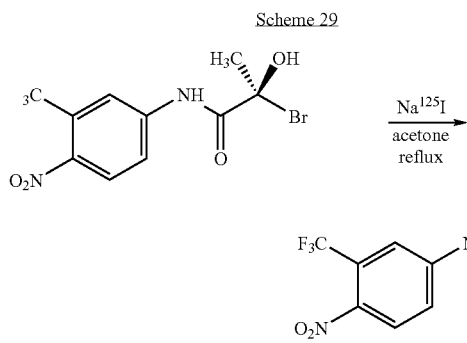

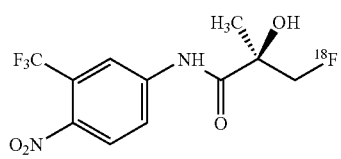

As shown below in Scheme 30, the radiolabeled compound can be produced from alkyl bromides (Kiesewetter et al., "Synthesis and Biological Properties of," J. Med. Chem., 38:1711–19 (1995); Berridge et al., "Design and Synthesis of $^{18}$F-Labeled Neurotoxic Analogs of MPTP," J. Med. Chem., 36:1284–90 (1993). It is possible to displace aliphatic bromide for fluoride with potassium [$^{19}$F]fluoride and Kriptofix (Berridge, "Chemistry of Fluorine-18 Radiopharmaceuticals," Appl. Radiat. Isot., 37:685–93 (1986); Goodman et al., "Synthesis of [$^{18}$F]-N-3-Fluoropropyl-2-," J. Labeled Comp. Radiopharm., 35:432–434 (1994)).

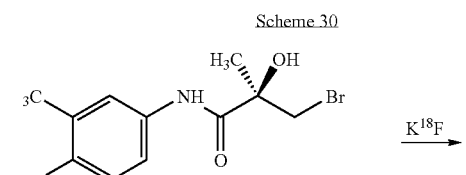

As shown below in Scheme 31, radiolabeled compounds of the present invention can be obtained using the procedure described in Berridge et al., "Design and Synthesis of 18F-Labeled Neurotoxic Analogs of MPTP," J. Med. Chem., 36:1284–90 (1993).

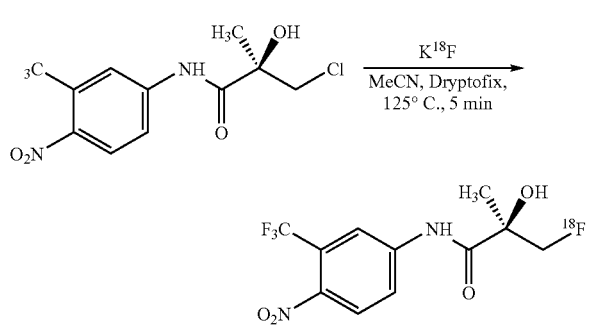

S. Aliphatic Organoboranes in Preparation of Radiohalogenated AR Ligands

As shown below in Scheme 32, the radiolabeled compounds of the present invention can be obtained as described in Kabalka, "The Synthesis of Radiolabeled Compounds Via Organometallic Intermediates," Tetrahedron, 45:6601–21 (1989).

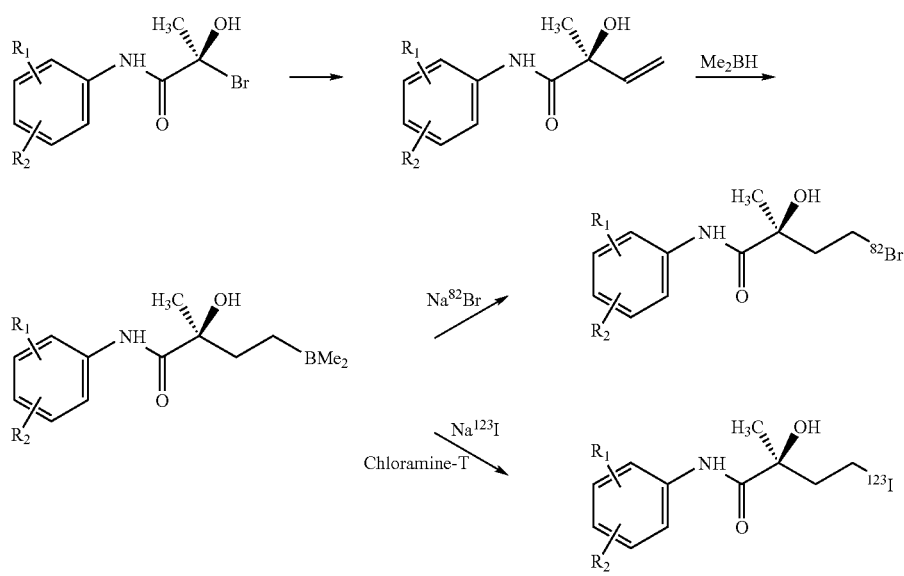

It will be appreciated by a person skilled in the art that the present invention is not limited by what has been particularly shown and described hereinabove. Rather, the scope of the invention is defined by the claims that follow:

What is claimed is:

1. A radiolabeled selective androgen receptor modulator compound (SARM) represented by the structure of formula I:

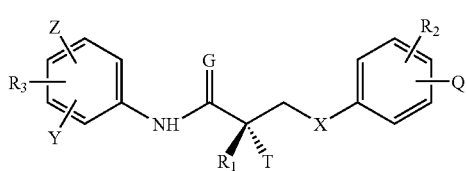

wherein
X is a radioactive or nonradioactive O
G is a radioactive O;
T is a radioactive or nonradioactive OH;
Z is a radioactive or a nonradioactive $NO_2$ or CN;
Y is a radioactive or a nonradioactive $CF_3$, F, Br, Cl, I, CN, or $Sn(R)_3$;
Q is a radioactive or a nonradioactive halogen, CN, $NHCOCH_3$;
R is a radioactive or a nonradioactive alkyl, haloalkyl, dihaloalkyl, trihaloalkyl, $CH_2F$, $CHF_2$, $CF_3$, $CF_2CF_3$, aryl, phenyl, halogen, alkenyl or OH; and
$R_1$ is a radioactive or nonradioactive $CH_3$;
$R_2$ is a radioactive or a nonradioactive F, Cl, Br, I, OH, CN, $NO_2$, $NHCOCH_3$, $NHCOCF_3$, NHCOR, alkyl, arylalkyl, OR, $NH_2$, NHR, $N(R)_2$, SR; and
$R_3$ is a radioactive or a nonradioactive F, Cl, Br, I, CN, $NO_2$, COR, COOH, CONHR, $CF_3$, $Sn(R)_3$;
wherein at least one of X, T, Z, Y, Q, R, $R_1$, $R_2$ or $R_3$ is radioactive and Y, or $R_2$ or $R_3$ is a radioactive halogen.

2. A radiolabeled selective androgen receptor modulator (SARM) compound represented by the structure of formula I:

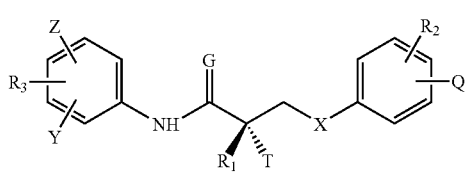

wherein
X is a radioactive or nonradioactive, O;
G is a radioactive or nonradioactive O;
T is a radioactive or nonradioactive OH;
Z is a radioactive or a nonradioactive $NO_2$ or CN;
Y is a radioactive or a nonradioactive $CF_3$, F, Br, Cl, I, CN, or $Sn(R)_3$;
Q is a radioactive or a nonradioactive halogen, CN, $NHCOCH_3$;
R is a radioactive or a nonradioactive alkyl, haloalkyl, dihaloalkyl, trihaloalkyl, $CH_2F$, $CHF_2$, $CF_3$, $CF_2CF_3$, aryl, phenyl, halogen, alkenyl or OH; and
$R_1$ is a radioactive or nonradioactive $CH_3$;
$R_2$ is a radioactive or a nonradioactive F, Cl, Br, I, OH, CN, $NO_2$, $NHCOCH_3$, $NHCOCF_3$, NHCOR, alkyl, arylalkyl, OR, $NH_2$, NHR, $N(R)_2$, SR; and
$R_3$ is a radioactive or a nonradioactive F, Cl, Br, I, CN, $NO_2$, COR, COOH, CONHR, $CF_3$, $Sn(R)_3$;
or its isomer, pharmaceutically acceptable salt, N-oxide, hydrate or any combination thereof,
wherein at least one of X, T, Z, Y, Q, R, $R_1$, $R_2$ or $R_3$ is radioactive and Y, or $R_2$ or $R_3$ is a radioactive halogen.

3. The radiolabeled selective androgen receptor modulator compound of claim 1, wherein Z is $NO_2$.

4. The radiolabeled selective androgen receptor modulator compound of claim 1, wherein Z is CN.

5. The radiolabeled selective androgen receptor modulator compound of claim 1, wherein Y is $CF_3$.

6. The radiolabeled selective androgen receptor modulator compound of claim 1, wherein Q is $NHCOCH_3$.

7. The radiolabeled selective androgen receptor modulator compound of claim 1, wherein Q is F.

8. The radiolabeled selective androgen receptor modulator compound of claim 1, wherein Q is NCS.

9. The radiolabeled selective androgen receptor modulator compound of claim 1, wherein $R_2$ is a radioactive halogen.

10. The radiolabeled selective androgen receptor modulator compound of claim 1, wherein $R_3$ is a radioactive halogen.

11. The radiolabeled selective androgen receptor modulator compound of claim 1, wherein said compound is an androgen receptor antagonist.

12. The radiolabeled selective androgen receptor modulator compound of claim 1, wherein said compound is an androgen receptor agonist.

13. The radiolabeled selective androgen receptor modulator compound of claim 1, wherein said compound binds irreversibly to an androgen receptor.

14. The radiolabeled selective androgen receptor modulator compound of claim 1, wherein said compound is an alkylating agent.

15. A composition comprising the radiolabeled compound of claim 1, and a pharmaceutically acceptable carrier.

* * * * *